US012774448B2

(12) United States Patent
Greppmair et al.

(10) Patent No.: US 12,774,448 B2
(45) Date of Patent: Oct. 27, 2026

(54) PROCESS FOR CULTURING MAMMALIAN CELLS

(71) Applicant: Hoffmann-La Roche Inc., Little Falls, NJ (US)

(72) Inventors: Katrin Greppmair, Penzberg (DE); Thomas Link, Penzberg (DE); Zhixin Shao, Penzberg (DE)

(73) Assignee: Hoffmann-La Roche Inc.

( * ) Notice: Subject to any disclaimer, the term of this patent is extended or adjusted under 35 U.S.C. 154(b) by 507 days.

(21) Appl. No.: 16/763,772

(22) PCT Filed: Nov. 29, 2018

(86) PCT No.: PCT/EP2018/083025
§ 371 (c)(1),
(2) Date: May 13, 2020

(87) PCT Pub. No.: WO2019/106097
PCT Pub. Date: Jun. 6, 2019

(65) Prior Publication Data
US 2020/0385673 A1 Dec. 10, 2020

(30) Foreign Application Priority Data
Nov. 30, 2017 (EP) .................................... 17204794

(51) Int. Cl.
*C12N 5/07* (2010.01)
*C12P 21/02* (2006.01)

(52) U.S. Cl.
CPC ................ *C12N 5/06* (2013.01); *C12P 21/02* (2013.01); *C12N 2500/60* (2013.01); *C12N 2523/00* (2013.01)

(58) Field of Classification Search
CPC ...... C12N 2500/60; C12N 5/06; C12M 41/26; C07K 16/00
See application file for complete search history.

(56) References Cited

U.S. PATENT DOCUMENTS

| | | | | |
|---|---|---|---|---|
| 8,426,202 B2 * | 4/2013 | Cayli | C12N 5/0018 435/70.1 |
| 8,470,552 B2 | 6/2013 | Croughan et al. | |
| 8,765,413 B2 | 7/2014 | Joosten et al. | |
| 2008/0227136 A1 * | 9/2008 | Pla | C12N 5/0037 435/405 |
| 2014/0051124 A1 | 2/2014 | Srivastava et al. | |

FOREIGN PATENT DOCUMENTS

| | | | | |
|---|---|---|---|---|
| CN | 101180396 A * | 5/2008 | C07K 14/38 |
| WO | 2006026445 A1 | 3/2006 | |
| WO | 2008033517 A2 | 3/2008 | |
| WO | 2011070024 A1 | 6/2011 | |
| WO | 2011117329 A1 | 9/2011 | |
| WO | 2013114164 A1 | 9/2011 | |
| WO | 2012140171 A1 | 10/2012 | |
| WO | 2015128795 A1 | 9/2015 | |
| WO | 2018/073365 A1 | 4/2018 | |
| WO | 2018/170099 A1 | 9/2018 | |

OTHER PUBLICATIONS

Brunner et al. The impact of pH inhomogeneities on CHO physiology and fed-batch process performance—two compartment scale-down modelling and intracellular pH excursion. Biotech J 2017 12:1600633 (Year: 2017).*
Miller et al. A kinetic analysis of hybridoma growth and metabolism in batch and continuous suspension culture: effectof nutrient concentration, dilution rate, and pH. Biotechnology and Bioengineering 1988, 32;8:947-955. (Year: 1988).*
Ivarsson et al. Evaluating the impact of cell culture process parameters on monoclonal antibody N-glycosylation. Journal of Biotechnology 2014, 188:89-96. (Year: 2014).*
Klein et al. The use of CrossMAb technology for the generation of bi- and multispecific antibodies. MABS 2016, 8;6:1010-1020. (Year: 2016).*
Sauer et al. A High-Yielding, Generic Fed-Batch Cell Culture Process for Production of Recombinant Antibodies. Biotechnology and Bioengineering 2000, 67;5:585-597. (Year: 2000).*
Zheng et al. Improved process robustness, product quality and biological efficacy of an anti-CD52 monoclonal antibody upon pH shift in Chinese hamster ovary cell perfusion culture. Process Bibchemistry 2018, 65:123-129. (Year: 2018).*
Bibila et al. In Pursuit of the Optimal Fed-Batch Process for Monoclonal Antibody Production. Biotechnology Progress 1995, 11:1-13. (Year: 1995).*
Hogiri et al, "Optimization of a pH-shift control strategy for producing monoclonal antibodies in Chinese hamster ovary cell cultures using a pH-dependent dynamic model," J Biosci Bioeng, Feb. 2018;125(2): pp. 245-250.
Zanghi et al., "Bicarbonate Concentration and Osmolality Are Key Determinants in the Inhibition of CHO Cell Polysialylation Under Elevated pCO2 or pH," Biotechnol. Bioeng. 65 (2), 182-191, 1999.
Zhang et al.,"Fed-batch culture of hybridoma cells in serum-free medium using an optimized feeding strategy," J Chem Technol Biotechnol 79:171-181, 2004.
Zhou et al., "High Viable Cell Concentration Fed-Batch Cultures of Hybridoma Cells Through On-Line Nutrient Feeding," Biotechnology and bioengineering 46(6):579-587, 1995.
Zhou et al., "Decreasing lactate level and increasing antibody production in Chinese Hamster Ovary cells (CHO) by reducing the expression of lactate dehydrogenase and pyruvate dehydrogenase kinases," J. Biotechnol. 153:27-34, 2011.

(Continued)

*Primary Examiner* — Christopher M Babic
*Assistant Examiner* — Jennifer S Spence

(57) ABSTRACT

Processes for culturing mammalian cells, and for producing recombinant products expressed by mammalian cells, involving a pH up-shift are provided. The processes are particularly suitable for industrial-scale cell culture, and for culture of cells that produce therapeutic products. The processes comprise a first culture stage, carried out at a first pH, and a second culture stage, carried out at a second pH that is higher than the first pH.

10 Claims, 32 Drawing Sheets

(56) References Cited

OTHER PUBLICATIONS

Zhu, "Mammalian cell protein expression for biopharmaceutical production," Biotechnol. Adv. 30 (5):1158-1170, 2012.
Zhu et al., "Effects of Elevated pCO2 and Osmolality on Growth of CHO Cells and Production of Antibody-Fusion Protein B1: A Case Study," Biotechnol Prog. 21:70-77, 2005.
Brunner et al., "The impact of pH inhomogeneities on CHO cell physiology and fed-batch process performance—two-compartment scale-down modelling and intracellular pH excursion," Biotechnol. J., 12 (7), 1600633 (2017).
Konakovsky et al., "Metabolic Control in Mammalian Fed-Batch Cell Cultures for Reduced Lactic Acid Accumulation and Improved Process Robustness," Bioeng., 3 (1), 5, 2016.
Xie et al., "Elucidating the effects of pH shift on IgGI monoclonal antibody acidic charge variant levels in Chinese banister ovary cell cultures," Appl. Microbiol. Biotechnol., 100 (24), 10343-10353 (2016).
Miller et al., "A Kinetic Analysis of Hybridoma Growth and Metabolism in Batch and Continuous Suspension Cultu.re: Effect of Nutrient Concentration, Dilution Rate, and pH," BHiotechnol., Bioeng., 32 (8), 947-965 (1988).
Trummer et al., "Process Parameter Shifting: Part I. Effect of DOT, pH, and Temperature on the Performance of Epo-Fc Expressing CHO Cells Cultivated in Controlled Batch Bioreactors," Biotechol. Bioeng., 94 (6), 1033-1044 (2006).
Tang et al.,"Performance analyses of a pH-shift and DOT-shift integrated fed-batch fermentation process for the production of ganoderic acid and Ganoderma polysaccharides by medicinal mushroom *Ganoderma lucidum,*" Bioresource Technol., 100 (5), 1852-1859 (2009).
Extended European Search Report dated Mar. 29, 2018 issued in Application No. 17204794.6.
International Search Report and Written Opinion dated Jan. 30, 2019 issued in Application No. PCT/EP2018/083025.
Aggarwal, S. What's fueling the biotech engine—2010 to 2011. Nat. Biotechnol. 29, 1083-1089 (2011).
Altamirano et al., "Decoupling Cell Growth and Product Formation in Chinese Hamster Ovary Cells Through Metabolic Control," Biotechnology and Bioengineering, 76(4):351-360, 2001.
Altamirano et al., "Considerations on the lactate consumption by CHO cells in the presence of galactose," 2006 J. Biotechnol. 125: 547-556.
Altamirano, et al., "Strategies for fed-batch cultivation of t-PA producing CHO cells: substitution of glucose and glutamine and rational design of culture medium," 2004 J. Biotechnology 110(2): 171-179.
Andersen and Goochee, "The effect of ammonia on the O-linked glycosylation of granulocyte colony-stimulating factor produced by chinese hamster ovary cells," 1995, Biotechnol Bioeng 47(1): 96-105.
Borys MC, Linzer DIH and Papoutsakis ET (1994), Ammonia affects the glycosylation patterns of recombinant mouse placental lactogenl by Chinese hamster ovary cells in a pH-dependent manner, Biotechnol Bioeng 43: 505-514.
Borys MC, Linzer DIH and Papoutsakis ET (1993), "Culture pH affects expression rates and glycosylation of recombinant mouse placental lactogen proteins by Chinese hamster ovary (CHO) cells," Bio/Technol 11: 720-724.
Chen and Flynn, "Analysis of N-glycans from recombinant immunoglobulin G by on-line reversed-phase high-performance liquid chromatography/mass spectrometry," Analytical biochemistry 370. 2: 147-161, 2007.
Chen et al., "Engineering of a mammalian cell line for reduction of lactate formation and high monoclonal antibody production," 2001 Biotechnol. Bioeng. 72: 55-61.
Cherlet and Marc, "Hybridoma cell behaviour in continuous culture under hyperosmotic stress," Cytotechnology 28: 71-84, 1999.
DeZengotita et al.,"Effects of CO2 and osmolality on hybridoma cells: growth, metabolism and monoclonal antibody production," Cytotechnology 28: 213-227, 1998.
DeZengotita et al., "Characterization of hybridoma cell responses to elevated pCO(2) and osmolality: intracellular pH, cell size, apoptosis, and metabolism," Biotechnol Bioeng. 77:369-380, 2002.
Fenn et al., "Crystal structure of an anti-Ang2 CrossFab demonstrates complete structural and functional integrity of the variable domain," PLoS ONE 8(4): e61953, 2013.
Fogolin et al. "Impact of temperature reduction and expression of yeast pyruvate carboxylase on hGM-CSF-producing CHO cells," J. Biotechnol. 109:179-191, 2004.
Gawlitzek et al.,"Ammonium alters N-glycan structures of recombinant TNFR-IgG: degradative versus biosynthetic mechanisms," Biotechnol Bioeng 68(6): 637-646, 2000.
Gomez et al., "Effect of temperature, pH, dissolved oxygen, and hydrolysate on the formation of triple light chain antibodies in cell culture," Biotechnology Progress 26(5):1438-1445, 2010.
Goudar et al., "Decreased pCO2 accumulation by eliminating bicarbonate addition to high cell-density cultures," Biotechnol. Bioeng. 96(6):1107-1117, 2007.
Hassell et al.,"Growth inhibition in animal cell culture—The effect of lactate and ammonia," Appl. Biochem. Biotechnol. 30:29-41, 1991.
Hayter et al.,"Chinese hamster ovary cell growth and interferon production kinetics in stirred batch culture," Appl Microbiol Biotechnol 34(5): 559-564, 1991.
Hume and MacDonald, "Therapeutic applications of macrophage colony-stimulating factor-1 (CSF-1) and antagonists of CSF-1 receptor (CSF-1R) signaling," Blood 119, 1810-1820, 2012.
Irani et al.,"Improvement of the primary metabolism of cell cultures by introducing a new cytoplasmic pyruvate carboxylase reaction," Biotechnol. Bioeng. 66, 238-246, 1999.
Kienast et al.,"Ang-2-VEGF-A CrossMab, a novel bispecific human IgG1 antibody blocking VEGF-A and Ang-2 functions simultaneously, mediates potent antitumor, antiangiogenic, and antimetastatic efficacy," Clinical Cancer Research 19(24): 6730-6740, 2013.
Kim, et al.,"CHO cells in biotechnology for production of recombinant proteins: current state and further potential," Appl. Microbiol. Biotechnol. 93 (3): 917-930, 2012.
Kim and Lee, "Functional expression of human pyruvate carboxylase for reduced lactic acid formation of Chinese hamster ovary cells (DG44)," Appl. Microbiol. Biotechnol. 76:659-665, 2007.
Kim and Lee,"Response of recombinant Chinese hamster ovary cells to hyperosmotic pressure: effect of Bcl-2 overexpression," J. Biotechnol. 95(3): 237-248, 2002.
Kim and Lee, "Down-regulation of lactate dehydrogenase-A by siRNAs for reduced lactic acid formation of Chinese hamster ovary cells producing thrombopoietin," Appl. Microbiol. Biotechnol. 74:152-159. 2007.
Kimura and Miller, "Glycosylation of CHO-Derived Recombinant tPA Produced under Elevated pCO2," Biotechnol Prog. 13:311-317, 1997.
Lao and Toth, "Effects of Ammonium and Lactate on Growth and Metabolism of a Recombinant Chinese Hamster Ovary Cell Culture," Biotechnol. Prog. 13: 688-691, 1997.
Leader et al.,"Protein therapeutics: a summary and pharmacological classification," Nature Reviews Drug Discovery 7: 21-39, 2008.
Li et al., "A Systematic Approach for Scale-Down Model Development and Characterization of Commercial Cell Culture Processes," Biotech Prog 22: 696-703, 2006.
Maranga and Goochee, "Metabolism of PER.C6TM cells cultivated under fed-batch conditions at low glucose and glutamine levels," Biotechnol Bioeng. 94:139-150, 2006.
Michaels, "Interfacial Properties of Cell Culture Media with Cell-Protecting Additives," Biotechnol Bioeng 47:420-430, 1995.
Michaels et al.,"Analysis of Cell-to-Bubble Attachment in Sparged Bioreactors in the Presence of Cell-Protecting Additives," Biotechnol Bioeng 47:407-419, 1995.
Mostafa and Gu,"Strategies for improved dCO2 removal in large-scale fed-batch cultures," Biotechnol Prog 19.1:45-51, 2003.

(56) References Cited

OTHER PUBLICATIONS

Oguchi et al.,"pH Condition in temperature shift cultivation enhances cell longevity and specific hMab productivity in CHO culture," Cytotechnology 52: 199-207, 2006.
Omasa et al.,"Cell Engineering and Cultivation of Chinese Hamster Ovary (CHO) Cells," Pharm. Biotechnol. 11 (3): 233-240, 2010.
Ozturk et al., "Effects of Ammonia and Lactate on Hybridoma Growth, Metabolism, and Antibody Production," Biotechnol. Bioeng., 39:418-431, 1992.
Paredes et al.,"Modification of glucose and glutamine metabolism in hybridoma cells through metabolic engineering," Cytotechnology 30: 85-93, 1999.
Ries et al.,"Targeting Tumor-Associated Macrophages with Anti-CSF-1R Antibody Reveals a Strategy for Cancer Therapy," Cancer Cell 25.6: 846-859, 2014.
Schaefer et al., "Immunoglobulin domain crossover as a generic approach for the production of bispecific IgG antibodies," Proc. Natl. Acad. Sci. U. S. A. 108:11187-11192, 2011.
Schmelzer and Miller, "Hyperosmotic Stress and Elevated pCO2 Alter Monoclonal Antibody Charge Distribution and Monosaccharide Content," Biotechnol Prog. 18:346-353, 2002.
Schmelzer et al., "Considerations for Osmolality Measurement Under Elevated pCO2: Comparison of Vapor Pressure and Freezing Point Osmometry," Biotechnol. Bioeng. 67 (2):189-196, 2000.
Trummer, et al., "Process Parameter Shifting: Part II. Biphasic Cultivation—A Tool for Enhancing the Volumetric Productivity of Batch Processes Using Epo-Fc Expressing CHO Cells," Biotechnology and Bioenginerring 96(6): 1045-1052, 2006.
Whitford, "Fed-Batch Mammalian Cell Culture in Bioproduction," Bioprocess International, 30-40, Apr. 2006.
Wlaschin and Hu, "Engineering cell metabolism for high-density cell culture via manipulation of sugar transport," J. Biotechnol. 131:168-176, 2007.
Xie and Wang,"Fed-Batch Cultivation of Animal Cells Using Different Medium Design Concepts and Feeding Strategies," Biotechnol Bioeng 43:1175-1189, 1993.
Yang and Butler,"Effects of Ammonia on CHO Cell Growth, Erythropoietin Production, and Glycosylation," Biotechnol. Bioeng. 68: 370-380, 2000.
Yeo et al., "Glutamine or glucose starvation in hybridoma cultures induces death receptor and mitochondrial apoptotic pathways," Biotechnol Lett. 28:1445-1452, 2006.
Yoon et al., "Biphasic culture strategy for enhancing volumetric erythropoietin productivity of Chinese hamster ovary cells," Biotechnol. Bioeng. 22: 345-356, 2006.
Yuk et al., "Effects of Copper on CHO Cells: Insights from Gene Expression Analyses," Biotechnology Progress30.2: 429-442, 2014.
The Communication of a notice of opposition, mailed on Dec. 19, 2024, in the related European Appl. No. 18811260.1.
Hogiri et al., "Optimization of a pH-shift control strategy for producing monoclonal antibodies in Chinese hamster ovary cell cultures using a pHdependent dynamic model," J. Biosci. Bioeng. (2018), 125: 245-250, published online Sep. 28, 2017. Supplemental material only.
Legmann R. et al., "A Predictive High-Throughput Scale-Down Model of Monoclonal Antibody Production in CHO Cells," Biotechnology and Bioengineering (2009), 104(6): 1107-1120.
Gagnon M. et al., "High-End pH-Controlled Delivery of Glucose Effectively Suppresses Lactate Accumulation in CHO Fed-Batch Cultures," Biotechnology and Bioengineering (2011), 108(6): 1328-1337.
Zagari F. et al., Lactate metabolism shift in CHO cell culture: the role of mitochondria! oxidative activity, New Biotechnology (2013), 30(2):238-245.

* cited by examiner

PROCESS FOR CULTURING MAMMALIAN CELLS

CROSS-REFERENCE TO RELATED APPLICATIONS

This application is a National Stage Application of PCT/EP2018/083025 filed Nov. 29, 2018, which claims priority from European Patent Application No. 17204794.6, filed on Nov. 30, 2017. The priority of said PCT and European Patent Application are claimed. Each of prior mentioned applications is hereby incorporated by reference herein in its entirety.

FIELD OF THE INVENTION

The present invention relates to mammalian cell culture. In particular the present invention relates to mammalian cell culture processes for the production of products, such as therapeutic products.

BACKGROUND

Recombinantly-expressed bio-therapeutics including monoclonal antibodies, antigens and other specialized protein modalities are increasingly used for the treatment of disease in fields such as oncology, immunosuppression, autoimmune disease, and inflammatory disorders (Leader et al., 2008; Aggarwal, 2011). As many of these therapeutics, or "bio-therapeutics" have recently been approved for treatment of cancer and autoimmune diseases at high doses, production of these bio-therapeutics at industrial scale is required in order to meet the increasing clinical demands.

Recombinant mammalian cells, especially Chinese hamster ovary (CHO) cells, are widely used in the pharmaceutical and biotechnology industries for manufacturing recombinant therapeutics. Progress has been made in improving mammalian cell culture processes in order to achieve a higher volumetric product yield with optimal product quality. (Omasa et al., 2010; Kim et al., 2012; Zhu, 2012). However, industrial scale production of therapeutics in mammalian cells remains challenging.

Many recombinant therapeutics production processes use fed-batch culture, which yields high cell density and high final product concentration. Under typical fed-batch cultivation conditions cells consume glucose and amino acids in excess to form biomass and product. This usually leads to large amounts of inhibitory metabolites, such as lactate and ammonium, being produced and accumulated in the culture medium. The presence of these inhibitory metabolites in high concentrations in the culture medium adversely affects cell growth and can result in low cell concentration and low product titer (Zhou et al., 1995; Ozturk et al., 1992; Lao and Toth, 1997). The accumulation of lactate and/or ammonium at excessive levels may also result in a higher culture medium osmolality, which can become a critical limiting factor for cell growth. Dissolved carbon dioxide at high concentrations can also negatively affect cell growth.

Accumulated lactate may acidify the cell culture and affect cell growth, cell productivity and final product quality. Even under controlled pH conditions accumulated lactate at high enough concentrations can be toxic to mammalian cells and may inhibit cell growth and protein production during the mid-to-late stage of the cell culture process. This is particularly true when the cell density is high.

In order to improve the overall productivity of mammalian cell cultures, efficient control of cell growth and metabolic activity is important. Significant efforts have been made to control the cellular glycolysis process/tricarboxylic acid (TCA) cycle and to reduce lactate accumulation in cultured cells. To this end, a number of strategies have been pursued, as follows:

1. Use of restricted amounts of glucose, or maintaining glucose at low levels during the cell culture process in order to improve glycolysis/TCA cycle efficiency and protein production (Xie and Wang, 1993; Altamirano et al., 2001; Zhang et al., 2004; Maranga and Goochee, 2006). However, Yeo et al. (2006) report that low glucose levels can easily lead to glucose depletion, apoptosis, and premature cell death.
2. Use of alternative sugars, such as fructose, galactose, and/or other glucose analogs in an attempt to reduce excessive lactate accumulation (Altamirano et al., 2000; Altamirano et al., 2004; Altamirano et al., 2006; Walschin and Hu, 2007). However, this strategy may also lead to lower cell growth rates or to reduced cellular productivity.
3. Metabolic engineering approaches to regulate glycolytic activity. Paredes et al. (1999) describe the genetic modification of a hybridoma cell line in order to reduce the amounts of ammonia and lactate produced by the cells. However, a major drawback of this approach is that the transformed cells are not stable.
4. Modulation of cellular lactate dehydrogenase activity by knocking-down lactate dehydrogenase (LDH) expression via homologous recombination or siRNA technology, or through use of an LDH competitive inhibitor such as oxamic acid. (Chen et al., 2001; Kim and Lee, 2007a; Zhou et al., 2011).
5. Over-expression of pyruvate carboxylase or use of a pyruvate dehydrogenase (PDH) activator to improve flux into the TCA cycle (Irani et al., 1999; Fogolin et al., 2004; Kim and Lee, 2007b). These approaches are often time-consuming and may result in unstable cell lines in CHO cell cultures.
6. Addition of divalent transitional metal salts (for example copper, zinc) to reduce lactate accumulation. Copper can be used in Chinese Hamster ovary (CHO) cells to shift from net lactate production to net lactate consumption, and achieve higher cell growth and productivity (Yuk et al., 2014). US20140051124 describes such methods of decreasing lactate production in cell culture using divalent transitional metallic salts.
7. Use of exogenous lactate: U.S. Pat. No. 8,470,552 describes a method for culturing animal cells in the presence of a sufficient concentration of exogenous lactate to reduce lactate production.
8. Control of culture conditions such as temperature and pH. Culture pH is one of the key physiological parameters known to have a significant influence on mammalian cell growth and target protein production (Borys et al., 1993; Yoon et al., 2005). Oguchi et al. (2006) describes the influence of reduced pH conditions on cell longevity, reporting also that pH has no influence on mRNA stability—a combination of lower pH and lower temperature is required to induce cell longevity and improve mRNA stability. Trummer et al. (2006) report controllable slowdown of cell metabolism at reduced temperatures and report that decreased pH values can significantly improve the volumetric productivity in CHO batch cell culture without affecting the quality of the secreted product.

U.S. Pat. No. 8,765,413 describes a similar approach in which a pH down-shift and a temperature down-shift are combined to slow down cellular metabolism, thereby reducing lactate formation and improving volumetric productivity in CHO cell culture. U.S. Pat. No. 8,765,413 reports that CHO cells generally produce less lactate at lower pH (e.g., pH 6.8) than at higher values (e.g., pH 7.0), and also suggests that shifting the culture pH to a lower value will decrease the concentration of extracellular ammonia.

WO 2008/033517 describes methods and compositions for producing recombinant proteins (in particular anti-TNFα or anti-interleukin-12 antibodies), including use of a linear pH ramp starting from a pH of about 7.1 to 7.2 and reducing to a final pH of about 6.9 over 24, 48, or 72 hours. This method reportedly leads to increased cell growth and productivity.

In an investigation of temperature and pH effects on THIOMAB 3LC formation, Gomez et al. (2010) report that high temperature and high pH conditions increases lactate accumulation that correlates with low cell viability.

In summary, previous studies have shown that pH down-shift in combination with temperature down-shift positively impacts cell viability, cellular productivity, and/or final product quality in mammalian cell cultures.

In addition to lactate, the accumulation of ammonia at high levels is also known to negatively affect cell growth, product titer, and post-translational modification of product in mammalian cell cultures (Hassell et al., 1991; Ozturk, et al. 1992).

Ammonia dissolved in the cell culture medium is converted to ammonium in a reaction (ammonia+$H_2O \rightleftharpoons$ ammonium+$OH^-$) that is dependent on the pH culture medium. When discussing their effects as inhibitory metabolites in cell culture processes, the terms "ammonia" and "ammonium" are generally used interchangeably.

Ammonia accumulated to over 14 mM has been shown to be detrimental to culture growth (Hayter et al., 1991; Lao and Toth, 1997), and high ammonium concentrations have also been shown to adversely impact the glycosylation patterns of recombinant proteins, reducing both galactosylation and sialylation (Andersen and Goochee, 1995; Borys et al., 1994; Gawlitzek et al., 2000).

Yang and Butler (2000) report that cell density decreases by 10% at 5 mM ammonia, and that the glycosylation pattern is altered at 10 mM ammonia in CHO cell cultures.

Despite this, few published studies have attempted to address the problem of ammonia accumulation in fed-batch production process.

Elevated levels of dissolved carbon dioxide is also known to affect cell growth and protein production in mammalian cell cultures. For fed-batch processes in bioreactors, $pCO_2$ levels can increase to significantly higher than normal physiological values. Dissolved $CO_2$ at such high levels can reduce cell growth and metabolism, lower productivity, and eventually elicit adverse effects on glycosylation (Mostafa and Gu, 2003; Kimura and Miller, 1997; deZengotita et al., 2002; Schmelzer and Miller, 2002; Zhu et al., 2005).

In fed-batch processes, high $pCO_2$ concentration normally results from both cellular metabolism and the use of $NaHCO_3/Na_2CO_3$ as a buffer in the culture medium. In addition, further $NaHCO_3$ is often added as a base in order to neutralize lactate produced by the cells.

One approach to reduce high $pCO_2$ level is to use bicarbonate-reduced or bicarbonate-free buffers. Goudar et al. (2007) used bicarbonate-free buffers in a perfusion process and achieved a 70% reduction in $pCO_2$ levels, as well as subsequent positive effects on cell growth and specific productivity. Despite this, the negative effects of elevated $pCO_2$ remain significant.

Another approach to remove $CO_2$ from cell cultures is gas stripping, however this generally has a limited impact in bioreactors in view of the relatively high solubility and low Henrys law constant for $CO_2$. Under normal cell culture operating conditions, adequate gas dispersion and ventilation is required to remove high levels of $CO_2$. However, as the bubble residence time increases with scale, the average driving force for $CO_2$ removal decreases rapidly. Therefore much higher gas flow rates are necessary for adequate $CO_2$ stripping to be effective. There is, however, an upper limit on sparging rates given the detrimental effects this has on cells (Michaels et al., 1995a, b).

Matching $pCO_2$ level and profile is also desirable during cell culture process scale-up and transfer between different manufacturing facilities. One key issue here is how to achieve the same or similar $pCO_2$ profiles across different scales. Normally larger scales show higher $pCO_2$ levels due to differences in fermenter hydrostatic pressure, mixing, and $CO_2$ stripping characteristics (Li et al., 2006; Mostafa and Gu, 2003). It is possible that a process with high $pCO_2$ level will be even more challenging to scale-up, as further escalation of $pCO_2$ could push the process to damaging conditions. Therefore, there is also a clear need to improve comparability of $pCO_2$ profiles between scales to increase the understanding of process levers on $pCO_2$ and to benefit future scale down models.

The small number of studies addressing $pCO_2$ control in mammalian cell bioreactors, focus largely on reducing $CO_2$ addition and on $CO_2$ removal. Alternative, more effective, approaches are required.

Osmolality is another important process variable during cultivation of mammalian cells. When increased to high levels, osmolality has been found to be detrimental to mammalian cell culture (Kim and Lee, 2002; deZengotita et al., 2002; Cherlet and Marc, 1999).

As the bioreactor pH during fed-batch cultivation is controlled at a pre-defined set-point, high $pCO_2$ leads to a concomitant increase in medium osmolality as a result of increasing concentrations of $HCO_3$ added as a base to control pH (Zanghi et al., 1999; Schmelzer et al., 2000). When osmolality and $pCO_2$ are both high, cell death rate increases significantly (deZengotita et al., 1998), and can lead to a significant reduction in the overall productivity.

In view of the above, there is a continued need for efficient cell culture processes overcoming these deficiencies. The present invention seeks to address this need.

SUMMARY OF THE INVENTION

This invention relates to processes for culturing cells, particularly mammalian cells. In particular the invention relates to a process for culturing mammalian cells in which the process comprises a pH up-shift.

In a first aspect the invention provides a fed-batch process for culturing mammalian cells, the process comprising a first culture stage comprising inoculating mammalian cells into a culture medium at a first pH and culturing the cells at the first pH, and a second culture stage comprising culturing the cells at a second pH that is higher than the first pH.

The processes disclosed herein advantageously avoid accumulation of undesirable metabolites. Such undesirable metabolites include lactate, ammonium and $CO_2$. The processes of the invention may result in higher cell viability, higher cell concentration and/or higher product titer.

The processes comprise a first culture stage at a first pH and a second culture stage at a second pH, wherein the second pH is higher than the first pH. The second pH may be at least 0.10 pH units higher than the first pH. The second pH may be about 0.1 to 0.5, 0.1 to 0.4, or 0.1 to 0.3 pH units higher than the first pH. The second pH may be about 0.2 pH units higher than the first pH. The first pH may be about 7.0. The first pH may be about 7.0 and the second pH may be about 7.2.

The first pH may be a range having a first lower limit and a first upper limit. The second pH may be a range having a second lower limit and a second upper limit, wherein the second lower limit is equal to or higher than the first upper limit, or wherein the second lower limit is higher than the first upper limit.

The processes may comprise controlling the pH using a set-point. In this context, the set-point may vary. Thus the processes may comprise controlling the pH using pH set-points. The processes may further comprise controlling the pH using a dead-band, which may be ±0.05 pH units relative to a pH set-point.

The processes of the invention comprise a pH up-shift. The processes comprise a first culture stage at a first pH and a second culture stage at a second pH, wherein the second pH is higher than the first pH. The first culture stage may comprise inoculating mammalian cells into a culture medium at the first pH. The pH up-shift stage is between the first culture stage and the second culture stage. The pH up-shift is the pH increase from the first pH to the second pH. This may be a gradual increase, which may be a continuous increase, or which may comprise discrete steps or increments. The processes may be processes that do not comprise a pH down-shift.

The processes may be fed-batch processes. A fed-batch process is where one or more nutrients are added to the culture vessel during the culture process. The cells remain in the culture vessel throughout the cell culture process. The cells and/or a product of the cells is harvested the end of the process.

The processes may comprise inoculating mammalian cells into a culture medium. The first culture stage of the process, which is carried out at a first pH, may comprise inoculating cells into a culture medium at the first pH. Inoculating cells into a culture medium refers to adding one or more cells, which may be a population of cells, into sterile culture medium. Inoculating may also be referred to as seeding. The mammalian cells may be CHO cells.

The temperature of the processes may be maintained at a substantially constant value. Processes in which the temperature is maintained at a substantially constant value do not comprise a significant temperature shift between the first culture stage and the second culture stage. A substantially constant temperature value may be within ±0.5° C. A substantially constant temperature value may be about 37° C. A substantially constant temperature value may be about 36.5° C. A substantially constant temperature value may be 36.0-37.0° C.

The processes of the invention may comprise culturing mammalian cells that are capable of expressing an antibody. The cells may be recombinant cells. The antibody may be a recombinant antibody. The cells may comprise a nucleic acid encoding the antibody under the control of a promoter, which may be an inducible promoter.

In a second aspect the invention provides a process for culturing mammalian cells, the process comprising a first culture stage, comprising culturing the cells at a first pH and a second culture stage comprising culturing the cells at a second pH, wherein the second pH is higher than the first pH and wherein the temperature of the process is maintained at a substantially constant value.

In a third aspect the invention provides a process for culturing mammalian cells, which mammalian cells are capable of expressing an antibody, the process comprising a first culture stage comprising inoculating mammalian cells into a culture medium at a first pH and culturing the cells at the first pH and a second culture stage comprising culturing the cells at a second pH that is higher than the first pH.

In each of the FIGS. 2A-G, 3A-G, 4A-G, 5A-G, 6A-G, 7A-G, 8A-G, 9A-G, 10A-F (FIGS. 2 to 10 series B to G) the grey diamonds indicate the process that is maintained at 7.00±0.05, and the black squares indicate the process involving a pH up-shift, as summarised in more detail below. Each of FIGS. 2B, 3B, 4B, 5B, 6B, 7B, 8B, 9B, 10B (series B) shows average cell viability (in %); each of FIGS. 2C, 3C, 4C, 5C, 6C, 7C, 8C, 9C, 10C (series C) shows lactate concentration (in %); each of FIGS. 2D, 3D, 4D, 5D, 6D, 7D, 8D, 9D, 10D (series D) shows ammonium concentration (in %); each of FIGS. 2E, 3E, 4E, 5E, 6E, 7E, 8E, 9E, 10E (series E) shows product titer (in %); each of FIGS. 2F, 3F, 4F, 5F, 6F, 7F, 8F, 9F, (series F) shows $pCO_2$ concentration (in %); and each of FIGS. 2G, 3G, 4G, 5G, 6G, 7G, 8G, 9G, 10F (series G) shows osmolality (mOsm/kg). Each of FIGS. 2B-G, 3B-G, 4B-G, 5B-G, 6B-G, 7B-G, 8B-G, 9B-G (FIGS. 2 to 9, each of series B to G) plots the average value of two 2 L bioreactors under identical conditions.

Figure 2A:
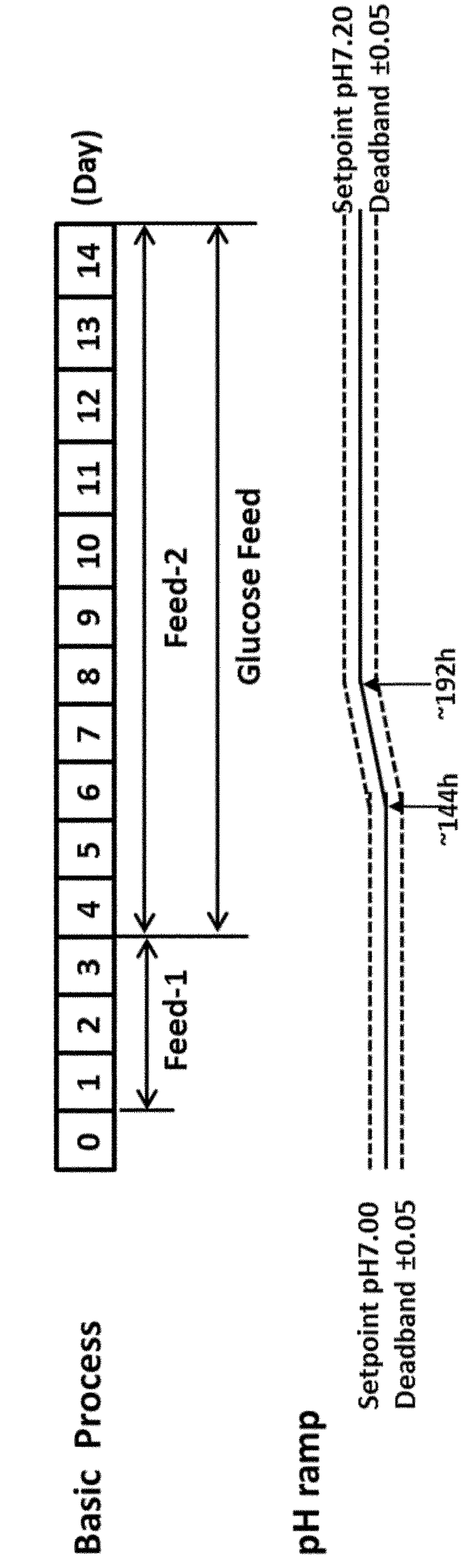

FIGS. 2A-2G show the effects of a pH up-shift (Δ0.20 pH-ramp) on a process for the production of an anti-Ang2NEGF bispecific antibody. FIG. 2A shows an overview of the process; the process begins with a pH set-point of 7.00±0.05, which is increased in a linear ramp to 7.20±0.05 over the period 144 hours to 192 hours. Following this, the pH set-point is maintained at 7.20±0.05 for the remainder of the 14 day runtime.

Figure 3A:
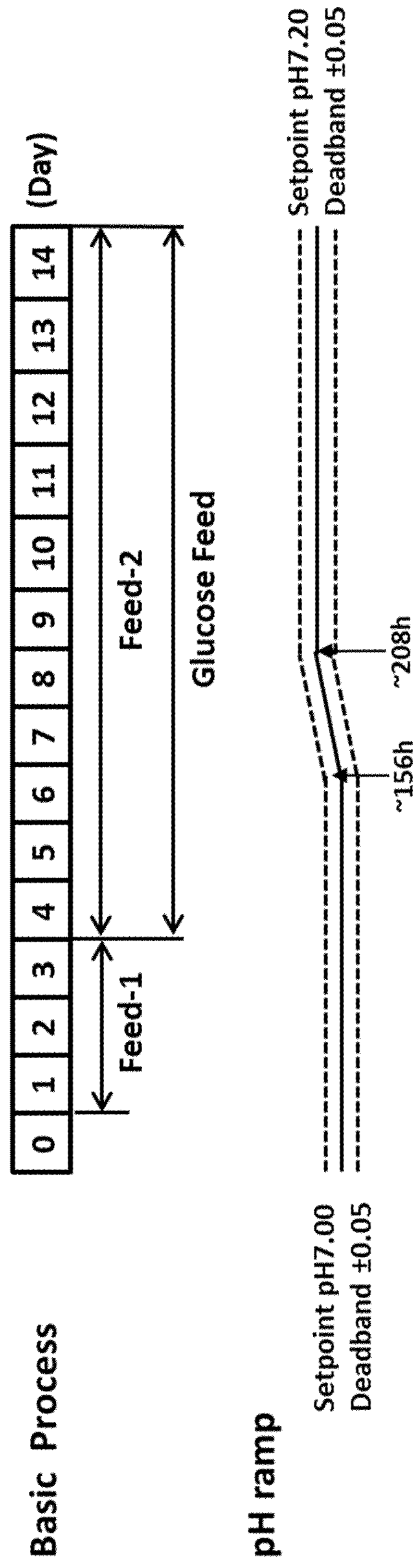

FIGS. 3A-G show the effects of a pH up-shift (Δ0.20 pH-ramp) on a process for the production of an anti-Ang2NEGF bispecific antibody. FIG. 3A shows an overview of the process; the process begins with a pH set-point of 7.00±0.05, which is increased in a linear ramp to 7.20±0.05 over the period 156 hours to 208 hours. Following this, the pH is maintained at 7.20±0.05 for the remainder of the 14 day runtime.

Figure 4A:
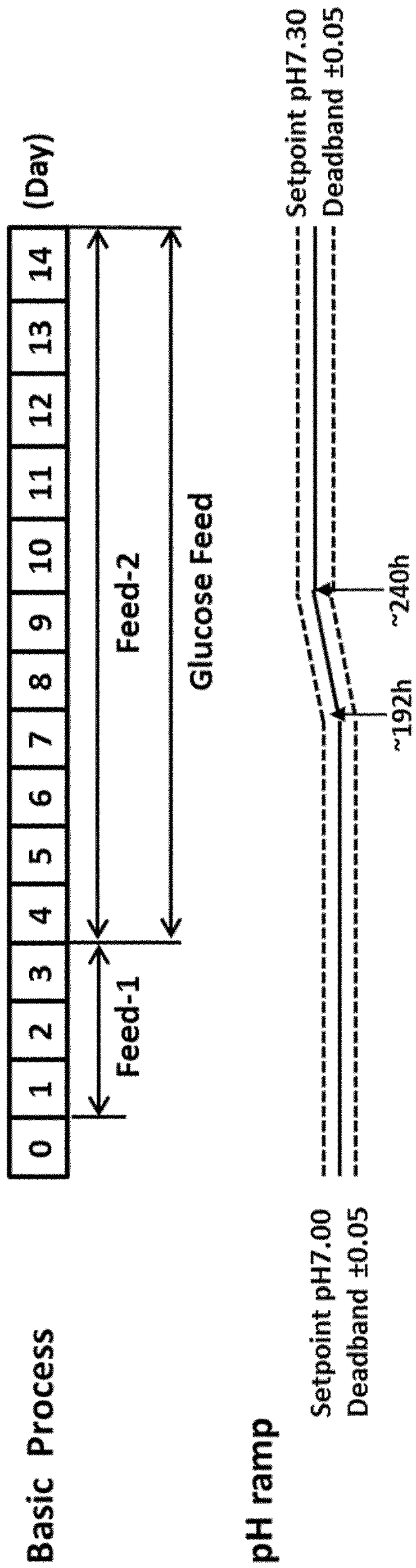

FIGS. 4A-G show the effects of a pH up-shift (Δ0.30 pH-ramp) on a process for the production of an anti-Ang2NEGF bispecific antibody. FIG. 4A shows an overview of the process; the process begins with pH maintained at a set-point of 7.00±0.05, which is increased in a linear ramp to 7.30±0.05 over the period 192 hours to 240 hours. Following this, the pH is maintained at 7.30±0.05 for the remainder of the 14 day runtime.

Figure 5A:
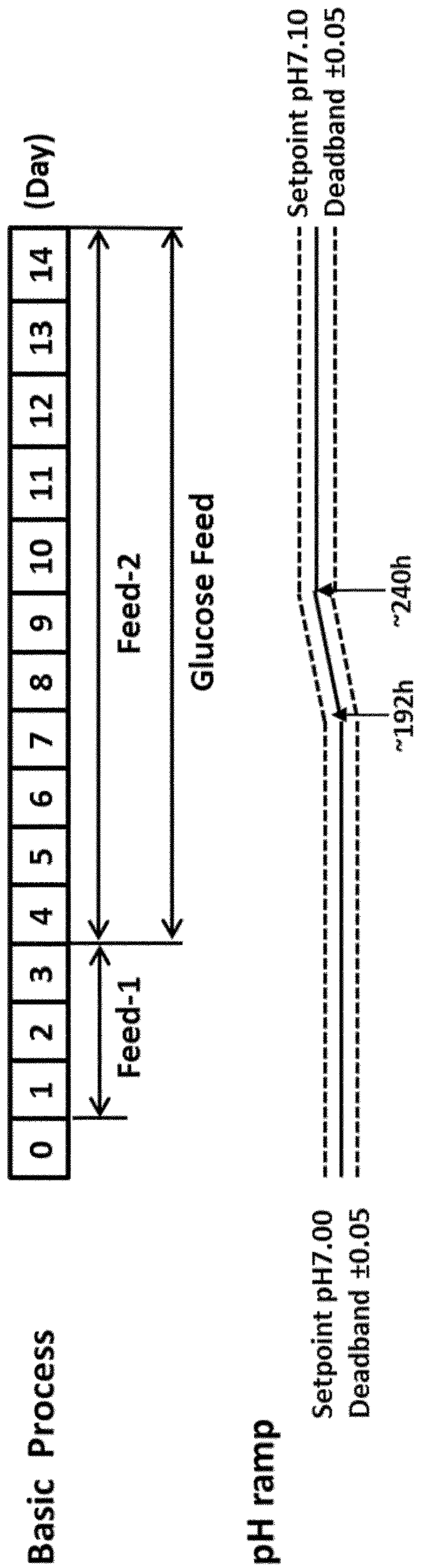

FIGS. 5A-G show the effects of a pH up-shift (Δ0.10 pH-ramp) on a process for the production of an anti-Ang2NEGF bispecific antibody. FIG. 5A shows an overview of the process; the process begins with a pH set-point of 7.00±0.05, which is increased in a linear ramp to 7.10±0.05 over the period 192 hours to 240 hours. Following this, the pH is maintained at 7.10±0.05 for the remainder of the 14 day runtime.

Figure 6A:
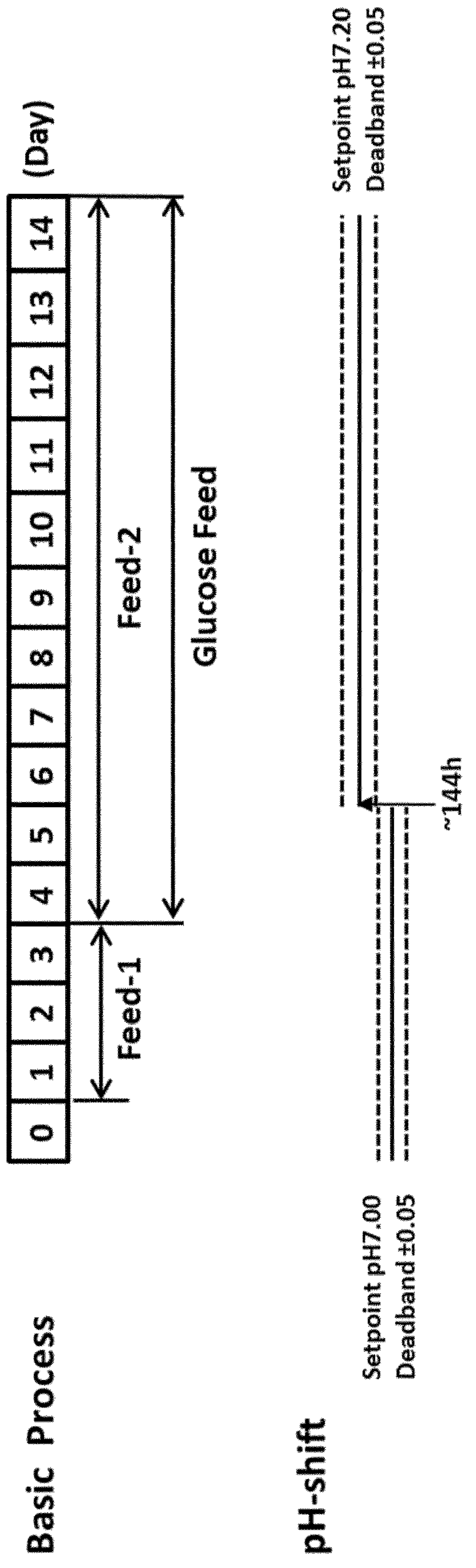

FIGS. 6A-G show the effects of an immediate pH up-shift (Δ0.20) on a process for the production of an anti-Ang2NEGF bispecific antibody. FIG. 6A shows an overview of the process; the process begins with a pH set-point of 7.00±0.05. At 144 hours, the pH set-point is increased instantly (in a single step) to 7.20±0.05 and is maintained at this level for the remainder of the 14 day runtime.

Figure 7A:
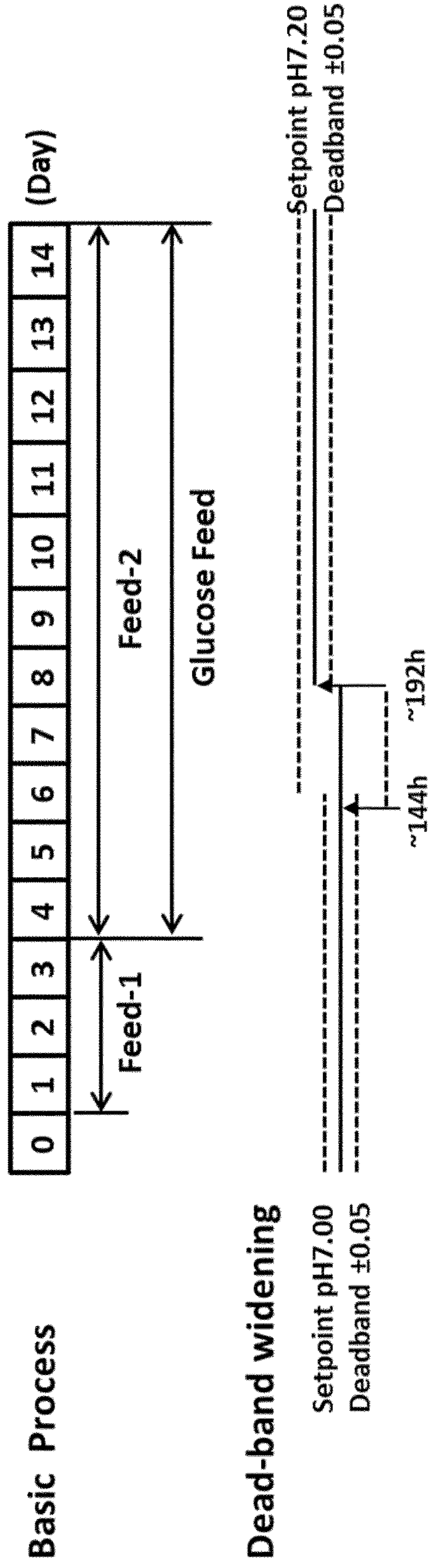

FIGS. 7A-G show the effects of a pH up-shift (Δ0.20 dead-band widening) on a process for the production of an anti-Ang2NEGF bispecific antibody. FIG. 7A shows an overview of the process. The process begins with a pH set-point of 7.00±0.05. At 144 hours, the pH dead-band is widened from 0.05 to 0.25. At 192 hours the pH set-point is increased to pH 7.20 and the pH dead-band is restored to 0.05. The pH set-point is maintained at 7.20±0.05 for the remainder of the 14 day runtime.

Figure 8A:
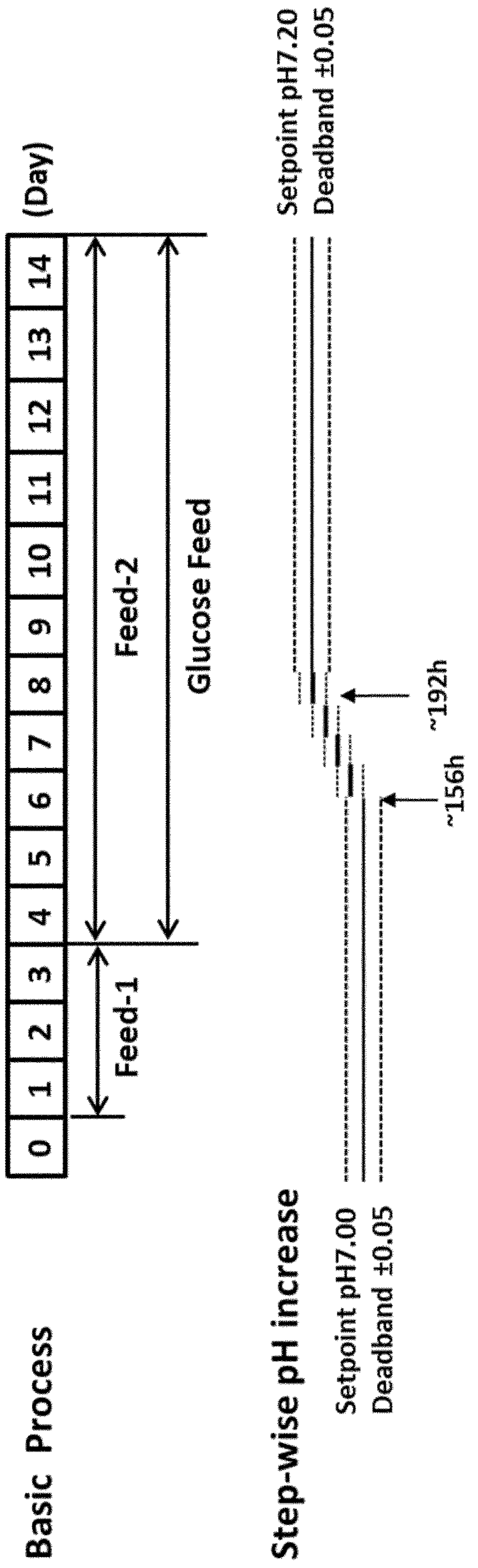

FIGS. 8A-G show the effects of a pH up-shift (Δ0.20 in incremental set-point increases of 0.05 from 7.00 to 7.20) on a process for the production of an anti-Ang2NEGF bispecific antibody. FIG. 8A shows an overview of the process. The process begins with a pH set-point of 7.00±0.05. At 156 hours, the pH set-point is increased to pH 7.05±0.05 and maintained for 12 hours. At 168 hours, the pH set-point is increased to pH 7.10±0.05 and maintained for 12 hours. At 180 hours, the pH set-point is increased to pH 7.15±0.05 and maintained for 12 hours. Finally, at 192 hours the pH set-point is increased to pH 7.20±0.05, and is maintained at this level for the remainder of the 14 day runtime FIGS. 9A-G show the effects of a pH up-shift (Δ0.20 in incremental dead-band widenings of 0.05 from 0.05 to 0.25) on a process for the production of an anti-Ang2NEGF bispecific antibody. FIG. 9A shows an overview of the process. The process begins with a pH set-point of 7.00±0.05. At 152 hours, the pH dead-band is widened to ±0.10 and maintained for 12 hours. At 164 hours, the pH dead-band is widened to ±0.15 and maintained for 12 hours. At 176 hours, the pH dead-band is widened to ±0.20 and maintained for 12 hours. At 188 hours, the pH dead-band is widened to ±0.25 and maintained for 12 hours. Finally, at 200 hours the pH set-point is increased to pH 7.20 with a dead-band of ±0.05, and is maintained at this level for the remainder of the 14 day runtime.

Figure 10A:
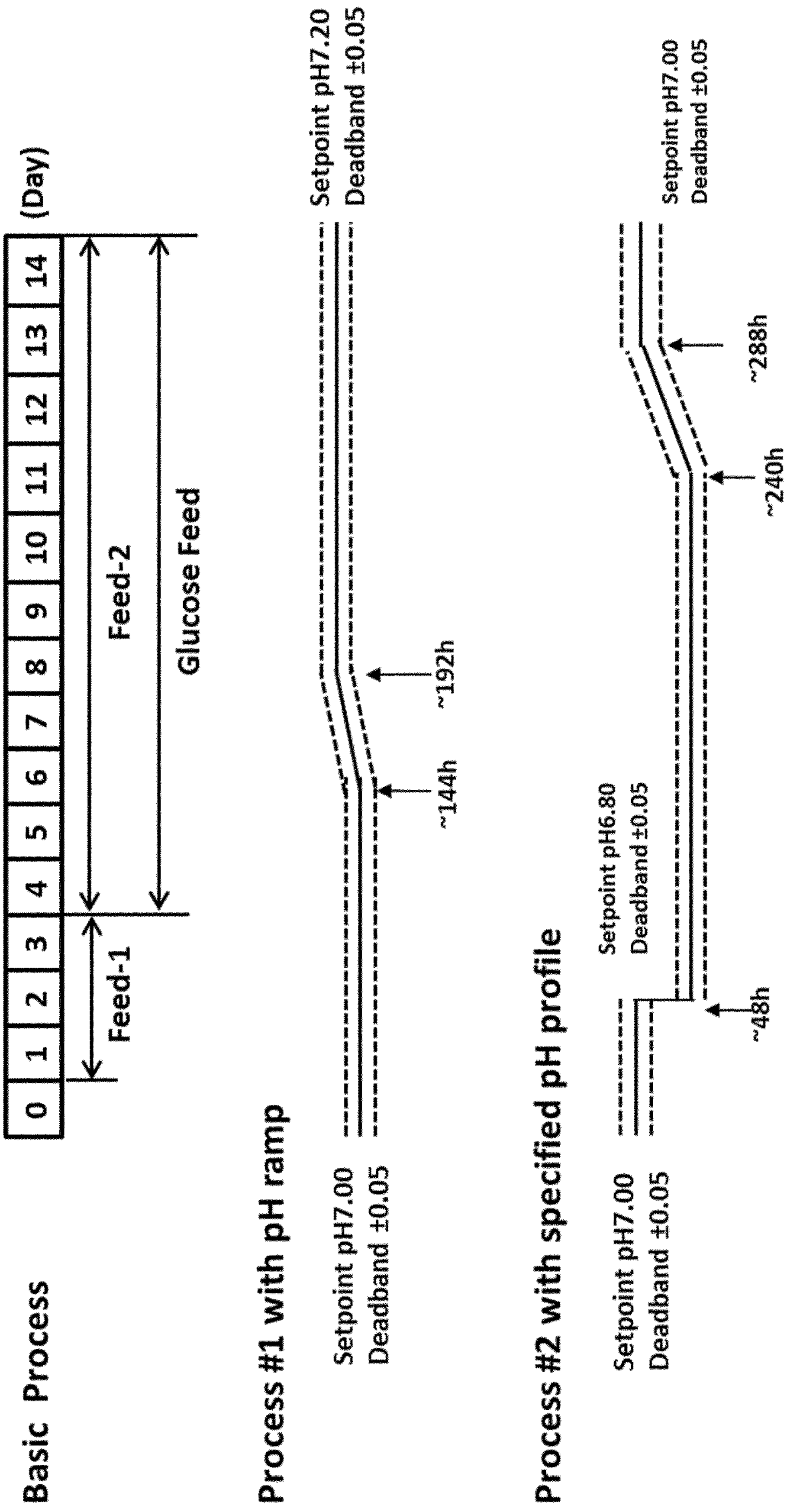
Figure 10B:
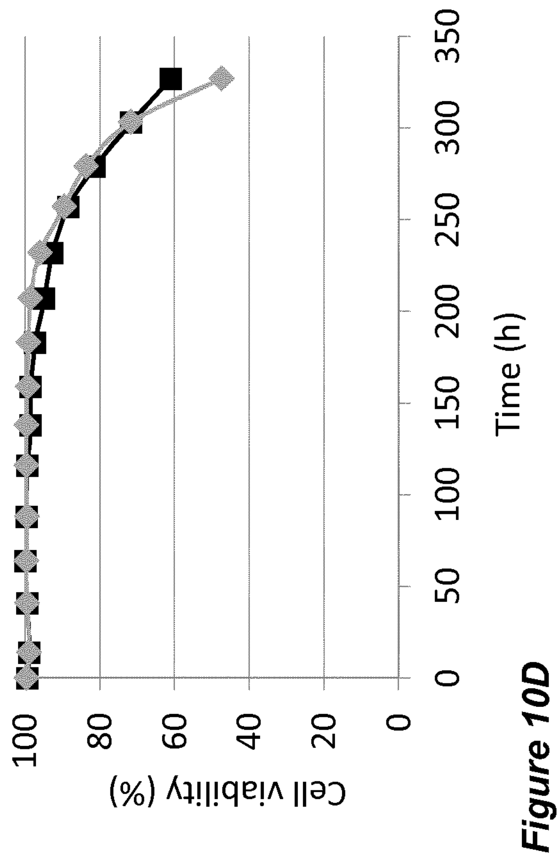
Figure 10C:
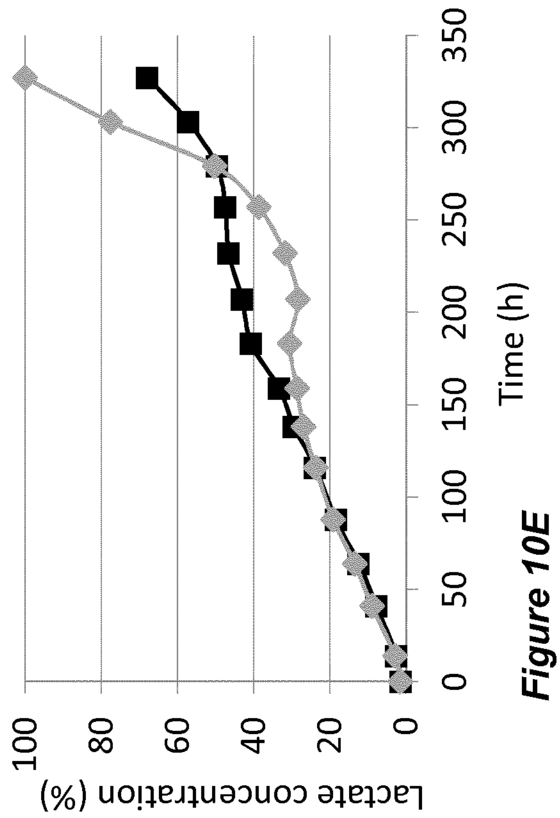
Figure 10D:
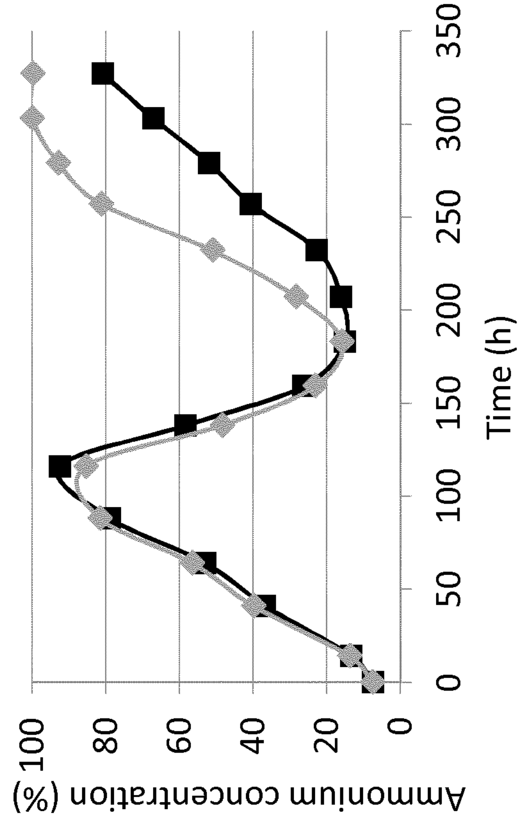
Figure 10E:
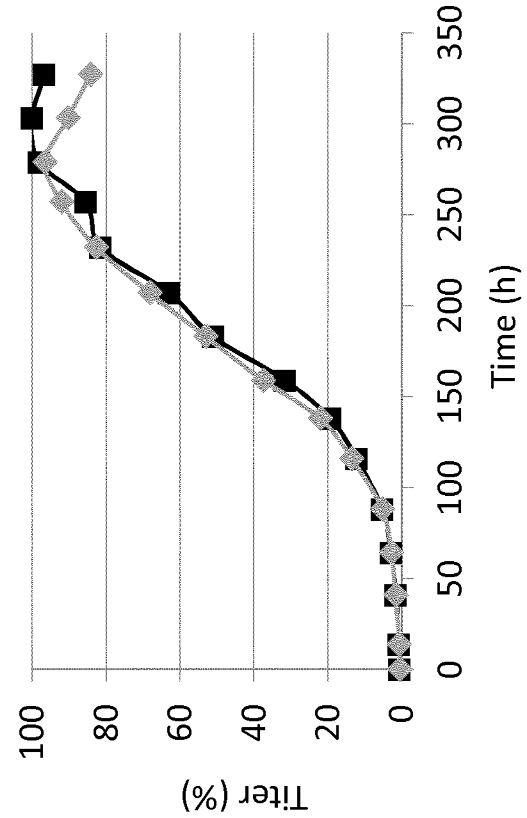
Figure 10F:
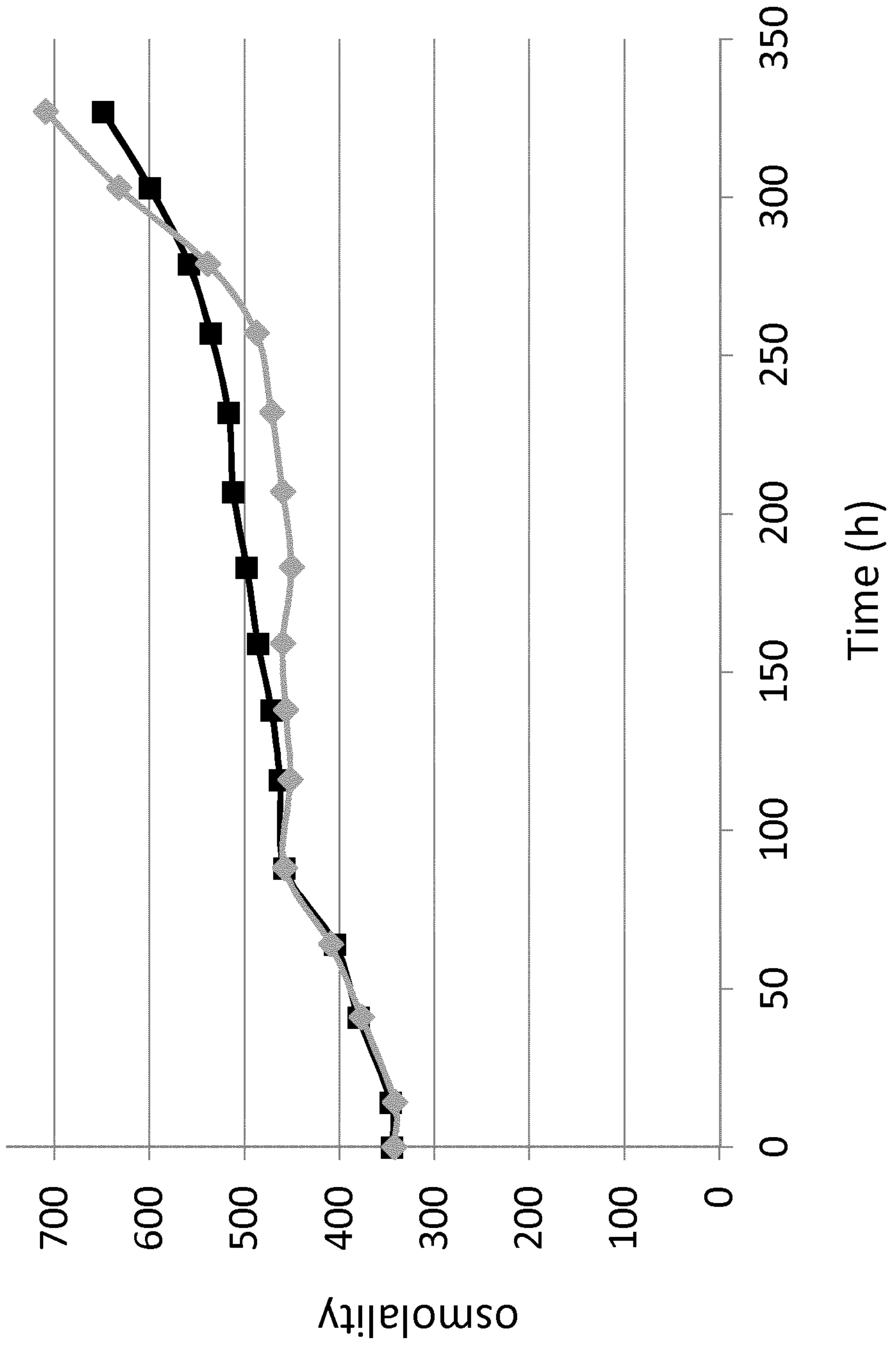

FIGS. 10A-F show the effects of different pH set-point and dead-band settings on processes for the production of an anti-CSF-1R antibody. FIG. 10A shows an overview of the two processes. Process #1 begins with a pH set-point of 7.00±0.05, which is increased in a linear ramp to 7.20±0.05 over the period 144 hours to 192 hours, and is subsequently maintained at this level for the remainder of the 14 day runtime. Process #2 begins with a pH set-point of 7.00±0.05, which is lowered instantly to 6.80±0.05 at 48 hours and maintained for 192 hours. Beginning at 240 hours the pH set-point is increased from 6.80±0.05 in a linear ramp to 7.00±0.05 over the period 240 hours to 288 hours, and is subsequently maintained at this level for the remainder of the 14 day runtime. FIG. 10B shows average cell viability (in %); FIG. 10C shows lactate concentration (in %); FIG. 10D shows ammonium concentration (in %); FIG. 10E shows product titer (in %); FIG. 10F shows osmolality (mOsm/kg). Each of FIGS. 10B to 10F plots the value for one bioreactor.

Figure 11A:
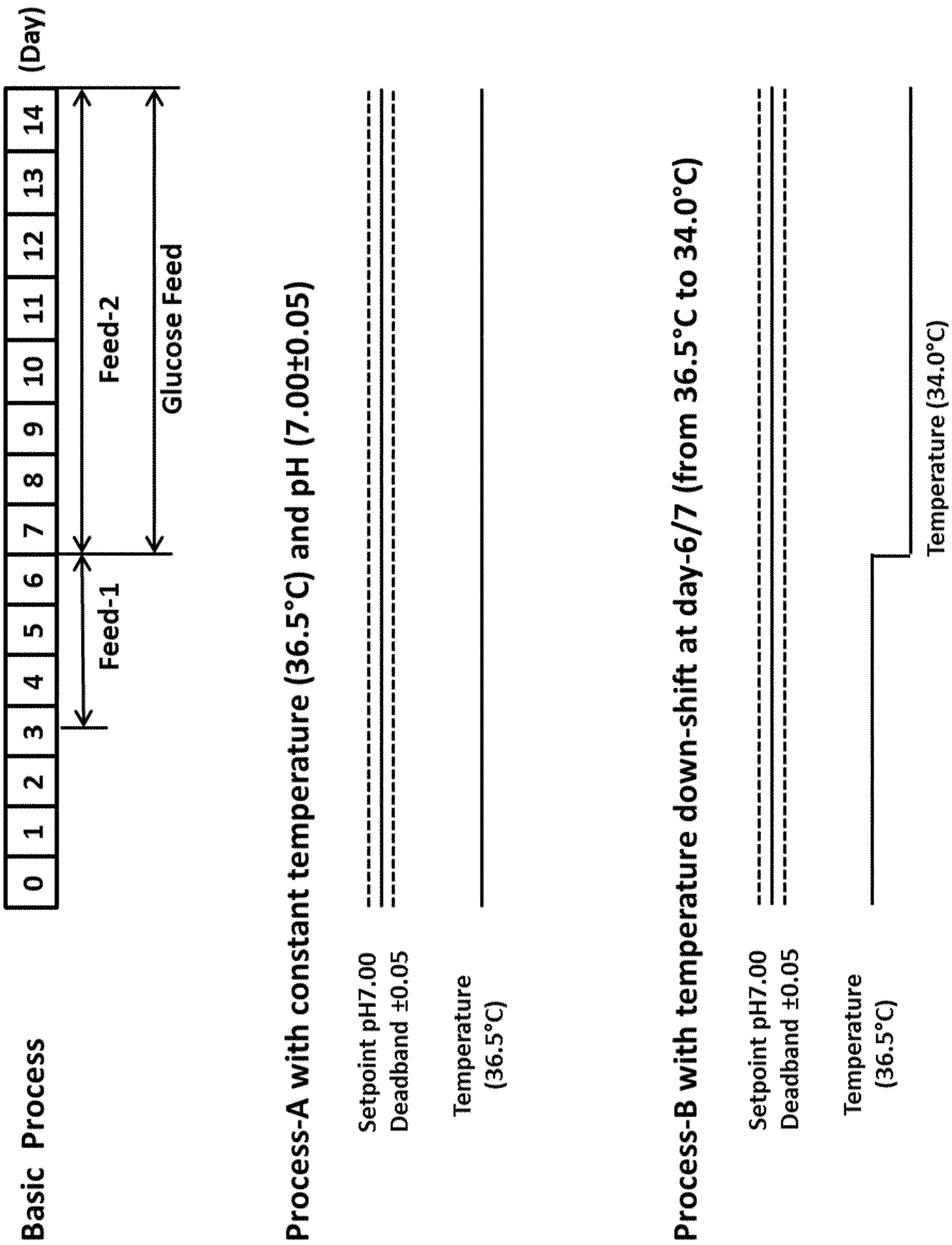
Figure 11B:
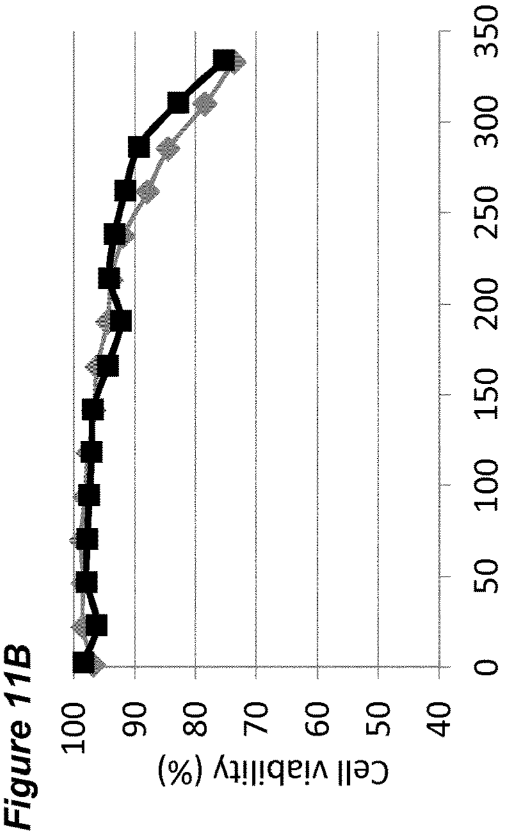
Figure 11C:
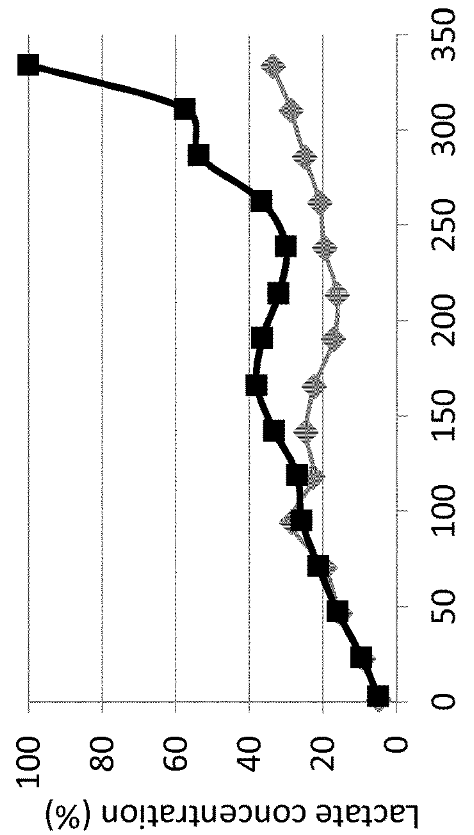
Figure 11D:
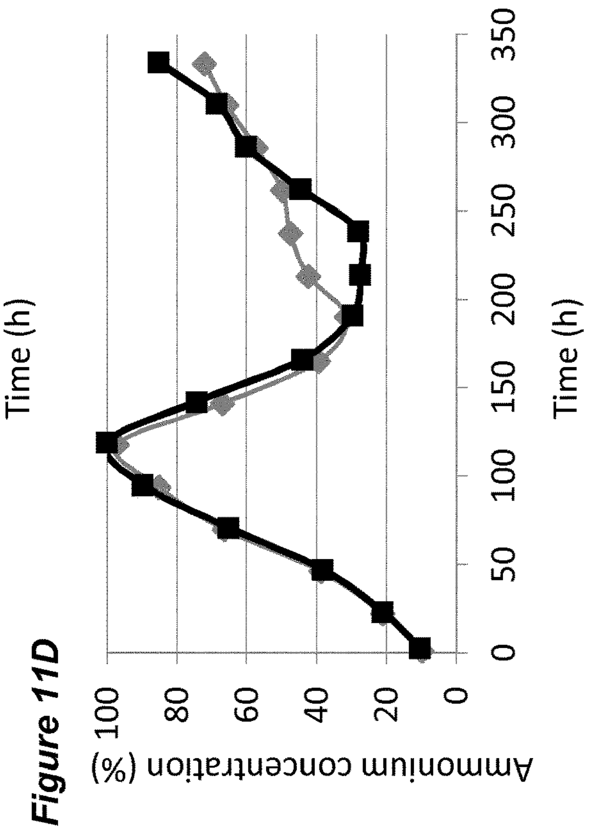
Figure 11E:
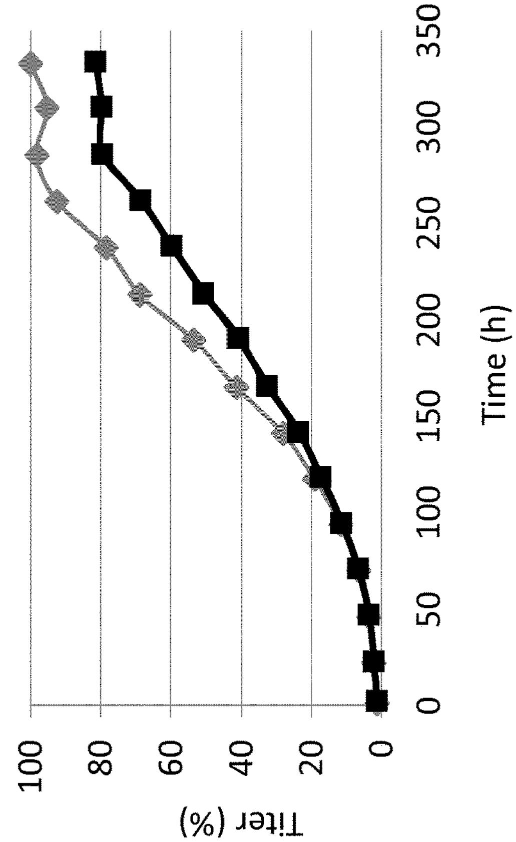
Figure 11G:
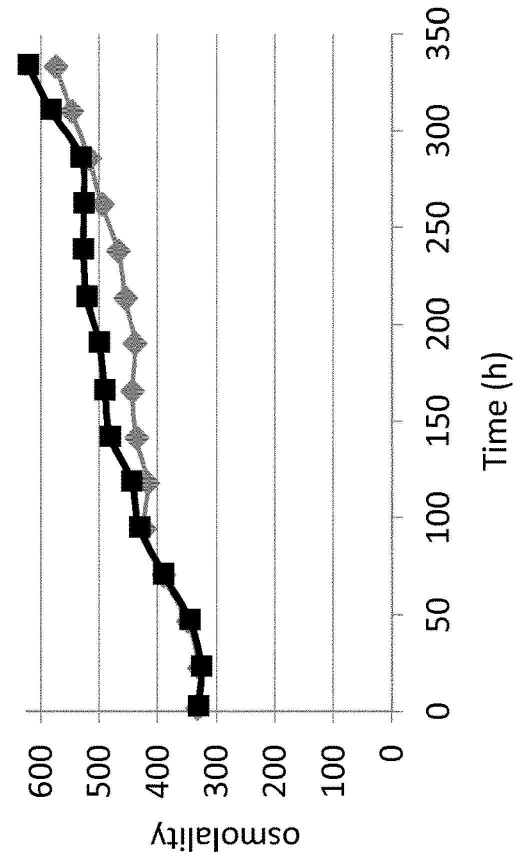
Figure 11F:
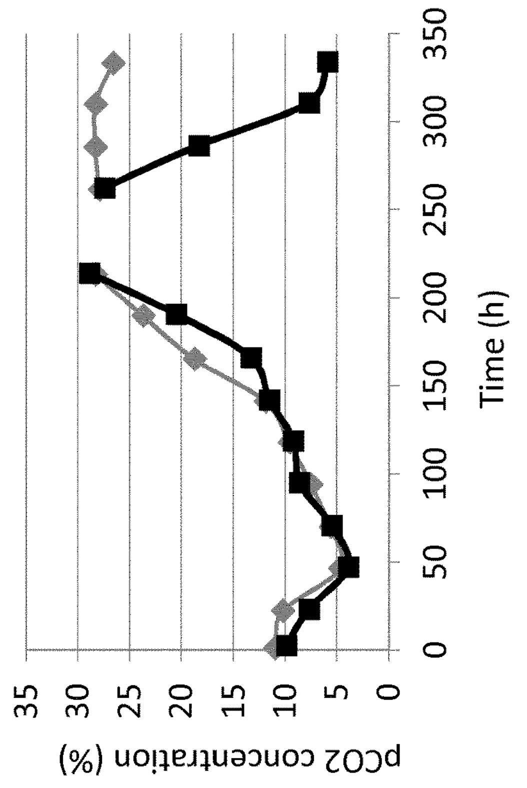

FIGS. 11A-11G show the effects of a temperature downshift on processes for the production of an anti-Ang2NEGF bispecific antibody. FIG. 11A shows an overview of the process. In Process A the temperature is maintained at 36.5° C. and the pH set-point is maintained at 7.00±0.05 for the entire 14 day runtime. Process B begins with the temperature maintained at 36.5° C. After 6/7 days the temperature is lowered to 34.0° C. and is subsequently maintained at this level for the remainder of the 14 day runtime. The pH is maintained at a constant set-point of 7.00±0.05 throughout. FIG. 11B is a line graph showing average cell viability (in %) for Process A (grey diamonds) and Process B (black squares). FIG. 11C is a line graph showing time course profiles of lactate concentration (in %) for Process A (grey diamonds) and Process B (black squares). FIG. 11D is a line graph showing time course profiles of ammonium concentration (in %) for Process A (grey diamonds) and Process B (black squares). FIG. 11E is a line graph showing time course profiles of product titer (in %) for Process A (grey diamonds) and Process B (black squares). FIG. 11F is a line graph showing time course profiles of $pCO_2$ concentration (in %) for a Process A (grey diamonds) and Process B (black squares). FIG. 11G is a line graph showing time course profiles of osmolality for Process A (grey diamonds) and Process B (black squares). In FIGS. 11B to 11F each plot is the average of two 2 L bioreactors under identical conditions.

Figure 12:
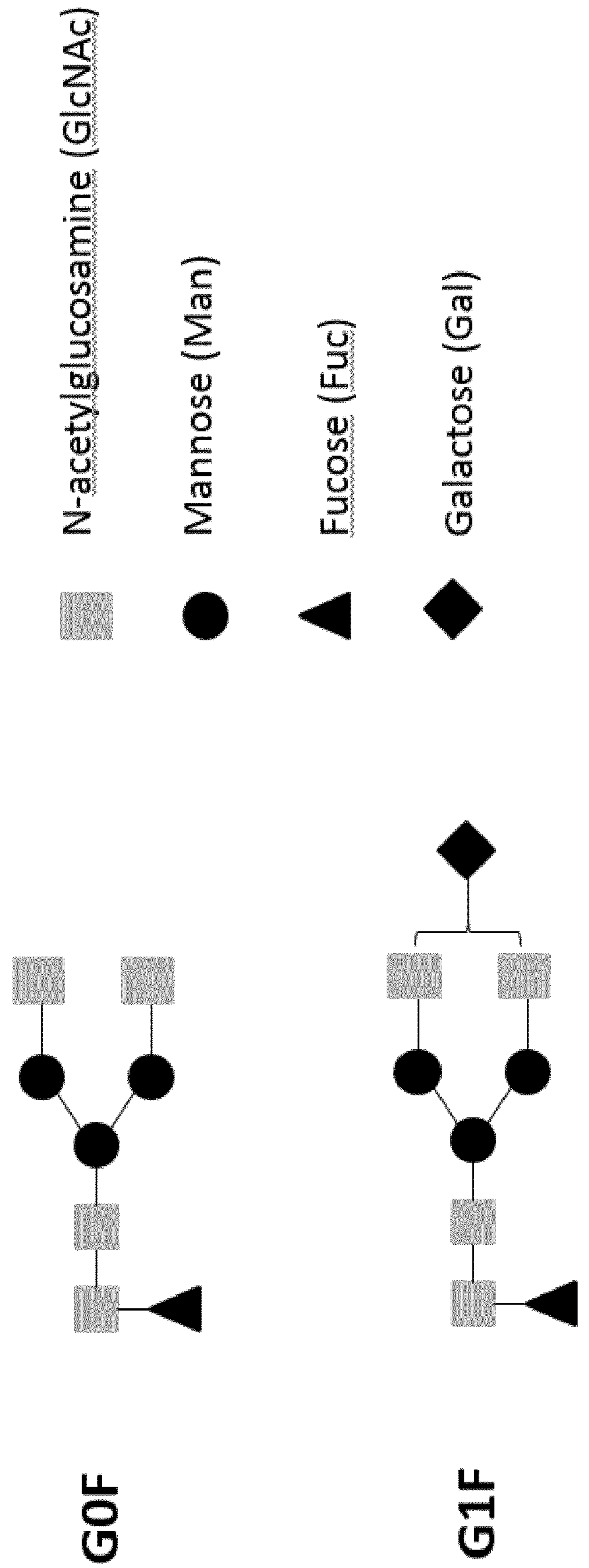

FIG. 12 shows related glycosylation structures for proteins produced in the processes disclosed herein.

DETAILED DESCRIPTION OF THE INVENTION

The invention provides processes for culturing mammalian cells. The processes of the invention involve a pH up-shift. In particular the processes of the invention involve a sustained pH up-shift. This reduces the accumulation of undesirable metabolites such as lactate and ammonium. The processes disclosed herein may improve maintenance of moderate $pCO_2$ levels and/or lower culture osmolality. Consequently the processes may result in higher cell viability, higher cell concentration, higher cell productivity, higher product titer, and/or improved product quality.

The processes comprising a pH up-shift may be improved relative to a control process in which the pH is the same throughout the process (same pH set-point in first and second culture stages). These improvements are illustrated in the accompanying FIGS. 2A-G to 9A-G, which show improvements in cell viability (B series of figures), lactate levels (C figures), ammonium levels (D figures), product titer (E figures), $pCO_2$ profile (F figures) and osmolality (G figures). The processes disclosed herein may advantageously avoid excessive lactate accumulation, especially in the late stages of the process and at the end of the processes. The processes may advantageously reduce ammonia production, and/or reduce excessive ammonia accumulation especially in the late stages of the process and at the end of the process.

The processes are particularly suitable for industrial-scale cell culture, and for culture of cells that produce therapeutic products. The culture vessels for such cell cultures may be termed bioreactors. An industrial scale process may be a process in which the volume of culture medium is at least about 50 L, 100 L, 500 L, 1000 L, or 10000 L. An industrial scale process may be a process in which the volume of culture medium is at least about 20 L, 30 L or 40 L. An industrial scale process may be a process in which the volume of culture medium is about 20-100 L, 20-500 L, 20-1000 L, 50-100 L, 50-500 L, 50-1000 L, 50-5000 L, 50-10000 L, 50-20000 L, 100-1000 L, 100-5000 L, 100-10000 L, 100-20000 L, 500-5000 L, 500-10000 L, or 500-20000 L.

The processes of the invention involve a pH up-shift. More specifically, the processes of the invention comprise a first culture stage at a first pH and a second culture stage at a second pH, wherein the second pH is higher than the first pH. The first culture stage may comprise inoculating mammalian cells into a culture medium at the first pH. The first culture stage may begin on Day 0 of the process. The first culture stage is the initial culture stage. The first culture stage may be the stage in which cell seeding and lag phase growth occurs. The first culture stage may be followed directly by a pH up-shift, which is followed directly by the second culture stage. The second culture stage may comprise harvesting the cells and/or a product produced by the cells. The process may terminate at termination of the second culture stage.

The processes are particularly suitable for industrial-scale cell culture, and for culture of cells that produce therapeutic products. The processes comprise a first culture stage, carried out at a first pH, and a second culture stage, carried out at a second pH that is higher than the first pH.

Disclosed herein is a fed-batch process for culturing mammalian cells, the process comprising a first culture stage comprising inoculating mammalian cells into a culture medium at a first pH and culturing the cells at the first pH, and a second culture stage comprising culturing the cells at a second pH that is higher than the first pH.

Disclosed herein is a fed-batch process for culturing CHO cells expressing an antibody such as Vanucizumab, the process comprising a first culture stage comprising inoculating mammalian cells into a culture medium at a first pH and culturing the cells at the first pH, and a second culture stage comprising culturing the cells at a second pH that is higher than the first pH, wherein the first pH is about 7.0 and wherein the second pH is about 0.1, 0.2, 0.3, 0.4, 0.5, or 0.1-0.5 units higher than the first pH.

The first pH may be a value in the range 6.5-7.5, 6.6-7.4, 6.7-7.3, 6.8-7.2, or 6.9-7.1. The first pH may be about 7.0. The first pH may be about 7.0 and the second pH may be about 7.2.

The first pH may have a value of about pH 6.5, 6.6, 6.7, 6.8, 6.9, 7.0, 7.1, 7.2, 7.3, 7.4, or 7.5. The second pH may have a value of about pH 6.6, 6.7, 6.8, 6.9, 7.0, 7.1, 7.2, 7.3, 7.4, 7.5, or 7.6. The first pH may have a value of about pH 6.5 to 7.5. The second pH may have a value of about pH 6.6 to 7.6, wherein the second pH is higher than the first pH.

The first pH may have a value of pH 6.5±0.05, 6.6±0.05, 6.7±0.05, 6.8±0.05, 6.9±0.05, 7.0±0.05, 7.1±0.05, 7.2±0.05, 7.3±0.05, 7.4±0.05, or 7.5±0.05. The second pH may have a value of pH 6.6±0.05, 6.7±0.05, 6.8±0.05, 6.9±0.05, 7.0±0.05, 7.1±0.05, 7.2±0.05, 7.3±0.05, 7.4±0.05, 7.5±0.05, or 7.6±0.05. The first pH may have a value of pH 6.5±0.05 to 7.5±0.05. The second pH may have a value of pH 6.6±0.05 to 7.6±0.05, wherein the second pH is higher than the first pH. The second pH may be about 0.1 pH units, or at least about 0.1 pH units higher than the first pH. A second pH that is about 0.1 pH units higher than the first pH may be referred to herein as pH Δ0.1. The second pH may be about 0.2, 0.3, 0.4, 0.5, 0.6, 0.7, 0.8, 0.9, or 1.0 pH units, or at least about 0.2, 0.3, 0.4, 0.5, 0.6, 0.7, 0.8, 0.9 or 1.0 pH units higher than the first pH. The second pH may be about 0.1-0.5 pH units higher than the first pH, about 0.1-0.4 units higher than the first pH, or about 0.1-0.3 pH units higher than the first pH. The first pH may be about 7.0. The second pH may be about 7.1-7.4, 7.1-7.5, 7.2-7.4 or about 7.2-7.5.

The first pH may be a value in the range 6.50-7.50, 6.60-7.40, 6.70-7.30, 6.80-7.20, or 6.90-7.10. The first pH may be about 7.00. The first pH may be about 7.00 and the second pH may be about 7.20.

The first pH may have a value of about pH 6.50, 6.60, 6.70, 6.80, 6.90, 7.00, 7.10, 7.20, 7.30, 7.40, or 7.50. The second pH may have a value of about pH 6.60, 6.70, 6.80, 6.90, 7.00, 7.10, 7.20, 7.30, 7.40, 7.50, or 7.60. The first pH may have a value of about pH 6.5 to 7.5. The second pH may have a value of about pH 6.6 to 7.6, wherein the second pH is higher than the first pH.

The second pH may be about 0.10 pH units, or at least about 0.10 pH units higher than the first pH. A second pH that is about 0.10 pH units higher than the first pH may be referred to herein as pH Δ0.10. The second pH may be about 0.20, 0.30, 0.40, 0.50, 0.60, 0.70, 0.80, 0.90 or 1.00 pH units, or at least about 0.20, 0.30, 0.40, 0.50, 0.60, 0.70, 0.80, 0.90 or 1.00 pH units higher than the first pH. The second pH may be about 0.10-0.50 pH units higher than the first pH, about 0.10-0.40 units higher than the first pH, or about 0.10-0.30 pH units higher than the first pH. The first pH may be about 7.00. The second pH may be about 7.10-7.40, 7.10-7.50, 7.20-7.40 or about 7.20-7.50.

The processes disclosed herein may comprise controlling the pH using a pH set-point. The set-point is the desired or target pH value. The processes may be in a bioreactor or other controlled culture facility that is programmable to regulate the pH using a pH set-point. In this context the bioreactor contains at least one pH probe to monitor the culture pH. Departure of the culture pH from its set-point may trigger a pH corrective action (or pH regulatory action) to bring the pH closer to the set-point. A pH corrective action may comprise addition of an agent that reduces the pH (such as $CO_2$, HCl or any other suitable acid) or addition of an agent that increases the pH (such as NaOH or any other suitable base). A pH corrective action may comprise removal of an agent that reduces the pH (for example removal of $CO_2$, known as $CO_2$ stripping). A pH corrective action may comprise attenuating the addition of an agent that reduces or increases the pH, in order to increase or reduce the pH respectively, for example attenuating the addition of $CO_2$ to maintain a relatively high pH.

The processes may comprise controlling the pH using a dead-band. A dead-band defines a zone within which no pH corrective action is triggered. Only when the pH drifts outside the zone defined by the dead-band is a pH corrective action triggered. The pH set-point may have a dead-band. The dead-band may be ±0.05, that is, the dead-band may be ±0.05 pH units relative to the pH set-point.

The processes disclosed herein may comprise controlling the pH using a pH set-point, wherein in the first culture stage the set-point is set to the first pH, and in the second culture stage the set-point is set to the second pH. In the first culture stage the set-point may be maintained at the first pH. In the second culture stage the set-point may be maintained at the second pH. In the first culture stage the set-point may be maintained at the first pH and in the second culture stage the set-point may be maintained at the second pH. The maintenance of the set-point may in the first and second culture stages may have a duration as set out below for the durations of the first and second culture stages respectively. A set point for the first culture stage, or the second culture stage, or both, may be maintained for at least 2, 4, 6, 8, 12, or 18 hours; or 3 to 10 days, 4 to 10 days, 4 to 8 days or 4 to 6 days; or at least 1, 2, 3, 4, 5, 6, 7, 8, 9, 10, 11, 12, 13, or 14 days. In the first culture stage the set-point may be set to pH 6.50, 6.60, 6.70, 6.80, 6.90, 7.00, 7.10, 7.20, 7.30, 7.40, or 7.50. In the second culture stage the set-point may be set to pH 6.60, 6.70, 6.80, 6.90, 7.00, 7.10, 7.20, 7.30, 7.40, 7.50, or 7.60, wherein the pH set-point of the second culture stage is higher than the pH set-point of the first culture stage. The pH set-point of the second culture stage may be about 0.10 pH units, or at least about 0.10 pH units higher than the pH set point of the first culture stage. A second pH that is about 0.10 pH units higher than the first pH may be referred to herein as pH Δ0.10. The second pH set-point may be about 0.20, 0.30, 0.40, 0.50, 0.60, 0.70, 0.80, 0.90 or 1.00 pH units, or at least about 0.20, 0.30, 0.40, 0.50, 0.60, 0.70, 0.80, 0.90 or 1.00 pH units higher than the first pH set-point. The second pH set-point may be about 0.10-0.50 pH units higher than the first pH, about 0.10-0.40 units higher than the first pH set-point, or about 0.10-0.30 pH units higher than the first pH set-point. The first pH set-point may be about 7.00. The first pH set point may be a value in the range 6.50-7.50, 6.60-7.40, 6.70-7.30, 6.80-7.20, or 6.90-7.10. The pH set-point may have a dead-band that is the same throughout the process, that is, the dead-band may have a constant value. The pH set-point in the first culture stage may have a dead-band that is the same as the dead-band of the pH set-point in the second culture stage. Alternatively, the pH set-point in the first culture stage and the pH set-point in the second culture stage may have dead-bands that are different from each other.

The pH set-point in the first culture stage and/or the second culture stage may have a dead-band of ±0.50, a dead-band of ±0.25, a dead-band of ±0.10, a dead-band of ±0.05 pH units, a dead-band of ±0.01, or a dead-band of ±0.005 pH units.

The pH set-point in the first culture stage may be 7.00±0.05. The pH set-point in the second culture stage may be from 7.10±0.05 to 7.40±0.05. The pH set-point in the first culture stage may be 7.00±0.05 and the pH in the second culture stage may be from 7.10±0.05 to 7.40±0.05. The pH set-point in the first culture stage may be 7.00±0.05 and the pH set-point in the second culture stage may be 7.10±0.05. The pH set-point in the first culture stage may be 7.00±0.05 and the pH set-point in the second culture stage may be 7.20±0.05. The pH set-point in the first culture stage may be 7.00±0.05 and the pH set-point in the second culture stage may be 7.30±0.05. The pH set-point in the first culture stage may be 7.00±0.05 and the pH set-point in the second culture stage may be 7.40±0.05.

The first pH may be a range having a first lower limit and a first upper limit. The second pH may be a range having a second lower limit and a second upper limit. The second lower limit may be equal to or higher than (≥) the first upper limit of the first pH, or higher than (>) the first upper limit of the first pH. In the processes of the invention the first culture stage comprises culturing the cells within the range having the first lower limit and first upper limit, and the second culture stage comprises culturing the cells within the range having the second lower limit and second upper limit.

The second lower limit may be equal to the first upper limit of the first pH. For example, the first pH may be a range having a first lower limit of 6.95 and a first upper limit of 7.05. For example the second pH may be a range having a second lower limit of 7.05 and a second upper limit of 7.15. The second lower limit may be greater than the first upper limit of the first pH. For example, the first pH may be a range having a first lower limit of 6.95 and a first upper limit of 7.05. For example the second pH may be a range having a second lower limit higher than 7.05 and a second upper limit higher than 7.15.

The second lower limit may be at least 0.10 pH units higher than the first upper limit. For example the first pH may be a range having a first lower limit of 6.95 and a first upper limit of 7.05, and the second pH may be a range having a second lower limit of 7.15 and a second upper limit of 7.25.

The second lower limit may be at least 0.20 pH units higher than the first upper limit. For example the first pH may be a range having a first lower limit of 6.95 and a first upper limit of 7.05, and the second pH may be a range having a second lower limit of 7.25 and a second upper limit of 7.35.

The second lower limit may be, or may be at least, 0.10 pH units higher than the first upper limit. The second lower limit may be, or may be at least, 0.20, 0.30, 0.40, 0.50, 0.60, 0.70, 0.80, 0.90 or 1.00 pH units, higher than the first upper limit.

The first pH and/or the second pH may be a range having a width of 1.00, 0.50, 0.20, 0.10, 0.02 or 0.01 pH units. The first pH may be a range having a mid-point value of pH 6.50, 6.60, 6.70, 6.80, 6.90, 7.00, 7.10, 7.20, 7.30, 7.40, or 7.50. The second pH may be a range having a mid-point value of pH 6.60, 6.70, 6.80, 6.90, 7.00, 7.10, 7.20, 7.30, 7.40, 7.50, or 7.60. For example the first pH may be a range having a mid-point value of pH 7.00 and a width of 0.10, which is a range of pH 6.95 to 7.05. The second pH may be a range having a mid-point value of pH 7.20 and a width of 0.10, which is a range of pH 7.15 to 7.25.

The process may be a process that does not comprise a pH down-shift (negative shift). That is, the processes may be a process that does not comprise any significant decrease in pH. A significant decrease in pH may be a decrease of at least 0.10, 0.20, 0.30, 0.40, 0.50, 0.60, 0.70, 0.80, 0.90 or 1.00 pH units, which may last at least 1, 5, or 30 minutes. The process may be a process that does not comprise culturing the cells at any pH that is lower than the first pH.

The processes of the invention comprise a pH up-shift. The pH up-shift is between the first and second culture stages. A pH up-shift is a positive shift or an alkaline shift, that is, the pH up-shift is an increase in pH. The pH up-shift is an increase in pH from the first pH to the second pH.

The pH up-shift may be gradual. That is, the pH up-shift may comprise a gradual increase in pH over a period of time. The pH may gradually increase from the first pH to the second pH for example over a period of time of 24-72 hours. The period of time may be 24-72 hours, 36-60 hours, or about 48 hours. The period of time may be, or may be at least 6, 12, 24, 36 or 48 hours. A gradual increase in pH may increase the pH by about, or by less than about, 0.001, 0.002, 0.003, 0.004, 0.005, 0.006, 0.007, 0.008, 0.009, 0.01, or 0.05 pH units per hour. A gradual increase in pH may increase the pH by about 0.001 to 0.05, 0.001 to 0.01, 0.001 to 0.005 or 0.002 to 0.008 pH units per hour.

Alternatively a pH up-shift may be "non-gradual". Such a pH up-shift may have a duration of less than 2 hours, or less than 1 hour, or less than 30, 20, 10, 9, 8, 7, 6, 5, 4, 3, 2, or 1 minutes. A non-gradual increase in pH may increase the pH by about, or by at least about, 0.1, 0.2, 0.3, 0.4, 0.5, 0.6, 0.7, 0.8, 0.9, 1.0, 1.5, 2.0, 2.5 or 3.0 pH units per hour, Increasing the pH gradually may advantageously minimise detrimental effects on the mammalian cells. Detrimental effects may be associated with an immediate or sudden increase of the pH of the culture medium, which effects are avoided by a gradual increase in pH. Processes of the invention in which the pH is increased gradually may have improved product titer and/or product quality compared to processes in which the pH increase is non-gradual, or in which pH set-point is increased in a single step as discussed below.

Processes of the invention which comprise controlling the pH using a pH set-point may comprise a pH up-shift in which the set-point is increased from the first pH to the second pH either (a) gradually or (b) instantly.

When the pH set-point is increased gradually, this may comprise a continuous increase in the set-point from the first pH to the second pH over a period of time. Alternatively, this may comprise a stepped increase in the set-point from the first pH to the second pH over a period of time. This period of time may be 24-72 hours, 36-60 hours or about 48 hours. This period of time may be at least 6, 12, 24, 36 or 48 hours.

A gradual continuous increase in pH set-point may be a termed a pH ramp, or a pH linear ramp. Thus the processes of the invention may comprise a pH up-shift which is a pH ramp, in which the set-point is continuously increased from the first pH to the second pH.

A gradual stepped increase in pH set-point may comprise discrete steps or increments. This may be termed a gradated increase. Each discrete step may increase the pH set-point by at least about 0.05 pH units. Each discrete step may increase the pH set-point by at least about 0.01, 0.05, 0.10, 0.15, 0.20, or 0.25 pH units. Each discrete step may be maintained for a period which is at least about 12 hours. Each discrete step may be maintained for a period which is at least about 1, 2, 4, 6, 8, 12, 18, 24 or 36 hours, or at least about 1-24 or 6-18 hours.

A gradual stepped increase in pH set-point may be carried out by repeatedly increasing the pH set-point until the pH set-point reaches the second pH. The stepped increase may repeatedly increase the pH set-point in a series of discrete steps, or increments.

For example a gradual stepped increase in pH set-point may be carried out by:

a) incrementally increasing the pH set-point from the first pH to an intermediate pH set-point and maintaining the culture at this intermediate pH set-point for a period of time;
b) incrementally increasing the pH set-point to a higher intermediate pH set-point and maintaining the culture at this higher intermediate pH set-point for a period of time; and;
c) repeating step b) until the pH set-point reaches the second pH.

Incrementally increasing the pH set-point may comprise increasing the pH set-point by increments of, or of at least, 0.05 pH units. The increments may be, or may be at least, about 0.01, 0.05, 0.10, 0.15, 0.20, or 0.25 pH units. Intermediate pH set-points may be maintained for a period which is at least about 12 hours. Each discrete step or increment may be maintained for a period which is at least about 1, 2, 4, 6, 8, 12, 18, 24 or 36 hours, or at least 1-24 or 6-18 hours. Each discrete step may be about 0.05 pH units maintained for about 12 hours.

A gradual increase in pH set-point that is a stepped pH set-point increase may be preferable in some situations. For example when technical limitations mean that the bioreactor cannot be programmed to gradually increase the pH set-point in a continuous increase.

The pH set-point may be increased instantly. An instant change in pH set-point may comprise an increase in the pH set-point from the first pH to the second pH in a single step. In this way, the pH set-point is changed from the first pH directly to the second pH without being set to any intermediate value. When the pH set-point is increased instantly from the first pH to the second pH, the pH of the fermentation may increase in a non-gradual manner. The amount of time taken for the pH of the fermentation to change from the first pH to the second pH may depend on the volume of the fermentation and/or the stirring rate. For example, Example 6 below involves an instant increase in the pH set-point, and the time taken for the fermentation to increase from the first pH to the second pH was about 10 minutes for a 2 L fermentation and 1-2 hours for a 1000 L fermentation.

The dead-band may be maintained at a constant value throughout the process. For example, the dead-band may be ±0.05 pH units about the set-point throughout the process. In embodiments in which the pH set-point increase is gradual, the dead-band may be maintained at a constant value in the first culture stage, the pH up-shift, and the second culture stage. Embodiments of processes in which the dead-band is maintained at a constant value are shown in FIGS. 2A, 3A, 4A, 5A, 6A, 8A, and 10A.

Alternatively the dead-band may be widened. In particular, the pH up-shift may comprise dead-band widening. The dead-band may be widened instantly, that is, the dead-band may be widened in a single step. An embodiment of a process in which the dead-band is widened in a single step is shown in FIG. 7A. Alternatively the dead-band may be widened gradually, for example the dead-band may be widened in a series of discrete steps or increments. An embodiment of a processes in which the dead-band is widened in a series of increments is shown in FIG. 9A.

The pH up-shift may comprise widening the dead-band in a single step, or instantly. The pH up-shift may comprise widening the dead-band from an initial value about the set-point that is set to the first pH to a wider value about the set-point that is set to the first pH in a single step, such that it encompasses the second pH, and then increasing the pH set-point to the second pH. The dead-band may be restored to its initial value about the pH set-point at the same time as the pH set-point is increased to the second pH. Alternatively, the dead-band may be restored to a value different from its initial value. The dead-band may be restored to a value that does not encompass the first pH.

For example, the process may comprise a first culture stage at pH 7.00 and a second culture stage at pH 7.20; the pH set-point in the first culture stage and the second culture stage may have a dead-band of ±0.05; the pH up-shift may comprise widening the dead-band about the set-point that is set to the first pH from ±0.05 to ±0.25 (from pH 7.00±0.05 to pH 7.00±0.25) in a single step such that it encompasses the second pH, and then increasing the pH set-point to the second pH. The dead-band may be restored to ±0.05 about the pH set-point that is set to the second pH (pH 7.20±0.05) at the same time as the pH set-point is increased to the second pH. FIG. 7A shows a process in accordance with this embodiment.

The pH up-shift may comprise widening the dead-band in a single step from ±0.05 to ±0.25. The pH up-shift may comprise widening the dead-band in a single step from ±0.01 to ±0.05, from ±0.05 to ±0.25, from ±0.05 to ±0.50, or from ±0.10 to ±0.50.

The dead-band may be widened in a single step and the widened dead-band may be maintained for about, or for at least 12, 18, 24, 36, 48, 60 or 72 hours. The widened dead-band may be maintained for 36-60, 40-56 or 44-52 hours, or about 48 hours. The widened dead-band may be maintained until the pH reaches the second pH.

The pH up-shift may comprise a gradual widening of the dead-band. The pH up-shift may comprise repeatedly widening the dead-band in a series of discrete steps or increments. The pH up-shift may comprise repeatedly widening the dead-band from an initial value about the pH set-point that is set to the first pH in a series of discrete steps or increments until the dead-band encompasses the second pH, and then increasing the pH set-point to the second pH. The dead-band may be restored to its initial value about the set-point that is set to the second pH at the same time as the pH set-point is increased to the second pH. Alternatively, the dead-band may be restored to a value different from its initial value. The dead-band may be restored to a value that does not encompass the first pH.

For example, the process may comprise a first culture stage at pH 7.00 and a second culture stage at pH 7.20; the pH set-point in the first culture stage and the second culture stage may have a dead-band of 0.05; the pH up-shift may comprise incrementally widening the dead-band about the set-point that is set to the first pH from ±0.05 to a value that encompasses pH 7.20 in a series of increments, for example four increments. The dead-band may then be restored to ±0.05 about the pH set-point that is set to the second pH (pH 7.20±0.05) at the same time as the pH is increased to the second pH. FIG. 9A shows a process in accordance with this embodiment.

The pH up-shift may comprise widening the dead-band in a series of increments or discrete steps. The increments may be 0.05 pH units. The increments, or discrete steps, may be, or may be less than, 0.01, 0.02, 0.03, 0.04, or 0.05 pH units. There may be at least two, three, four or five increments. The increments may be the same size as each other, or different sizes. For example a dead-band of ±0.05 may be widened to ±0.25 in a series of four increments of 0.05 pH units as follows: to ±0.10, to ±0.15, to ±0.20, to ±0.25.

The dead-band may be widened in a series of increments or discrete steps, and each increment or discrete step may be maintained for about, or for at least, 12 hours. Each increment or discrete step may be maintained for about, or for at least 2, 4, 6, 8, 12, 18, or 24 hours. The increments may have the same duration as each other, or different durations.

The pH up-shift may comprise a continuous gradual widening of the dead-band over a period of time. The pH up-shift may comprise continuously widening the dead-band from an initial value about the pH set-point that is set to the first pH until the dead-band encompasses the second pH, and then increasing the pH set-point to the second pH. The dead-band may be restored to its initial value about the set-point that is set to the second pH at the same time as the pH set-point is increased to the second pH. Alternatively, the dead-band may be restored to a value different from its initial value. The dead-band may be restored to a value that does not encompass the first pH.

For example, the process may comprise a first culture stage at pH 7.00 and a second culture stage at pH 7.20; the pH set-point in the first culture stage and the second culture stage may have a dead-band of ±0.05; the pH up-shift may comprise continuously widening the dead-band about the set-point that is set to the first pH from ±0.05 to a value that encompasses pH 7.20. The dead-band may then be restored to ±0.05 about the pH set-point that is set to the second pH (pH 7.20±0.05) at the same time as the pH is increased to the second pH.

The period of time over which the dead-band is continuously widened may be 24-72 hours, 36-60 hours or about 48 hours. This period of time may be at least 6, 12, 24, 36 or 48 hours.

An incremental increase in dead-band may be preferable in some situations. For example when technical limitations mean that the bioreactor cannot be programmed to gradually increase the pH set-point in a continuous increase or when technical limitations mean that the bioreactor cannot be programmed to continuously widen the dead-band.

The pH up-shift may comprise an increase in the set-point and a widening of the dead-band in any operable combination of the above. In some situations, the combinations in the embodiments shown in FIGS. 2A to 9A may be preferable, for example to minimise fluctuations in pH (pH turbulence).

The pH may be measured on-line or off-line. The pH values discussed herein refer to on-line values unless stated otherwise. The pH may be measured at 37.0±1.0° C. The pH may be measured at 36.5±1.0° C. The pH may be measured at the temperature used in the bioreactor for the production fermentation. For on-line measurements the pH is measured by a probe in the bioreactor. Suitable pH probes for on-line measurements include a Mettler-Toledo InPro pH sensor. For off-line measurements the pH is measured by a probe in a sample from the bioreactor, for example in a temperature controlled sample vessel. Suitable apparatus for off-line measurement include the Knick Portavo 907 pH meter, pH 3310 WTW, and the Mettler-Toledo InPro Semi-Micro pH electrode. Suitable sampling devices include the S-S-MONOVETTE® 9 mL (Sarstedt).

The procedure for off-line pH measurement may be as follows: pre-warm benchtop pH electrode to the measurement temperature (e.g. 37.0±1.0° C.) by immersing in a water bath or aluminium block at the measurement temperature; then heat the sample to the measurement temperature (e.g. 37.0±1.0° C.) and measure the pH as soon as the sample has reached the measurement temperature (e.g. after three minutes); then wait until a stable pH value is reached (e.g. less than 1 minute); the sable pH value is used as the off-line measurement. Calibration buffers may be used to calibrate the pH measurement apparatus, for example Duracal Buffers (Hamilton).

The on-line measurement may be re-calibrated if it differs significantly from the off-line measurement. For example if the on-line measurement differs by more than 0.05 pH units. A re-calibration procedure may comprise taking a second sample from the bioreactor if the first sample has measured as having an off-line pH value that differs by more than 0.05 pH units from the on-line value. If the second sample also as an off-line pH value that differs by more than 0.05 pH units from the on-line value then the on-line (internal) pH probe is re-calibrated by setting to the pH value determined by the off-line (external) pH probe.

The processes of the invention may comprise addition of a pH up-shift feed medium to the culture medium. The pH up-shift feed medium may have an alkaline (basic) pH relative to the culture medium. Alternatively or additionally, the pH up-shift feed medium may contain factors, such as nutrients, that when metabolised by cells increase the pH of the culture medium. For example, certain amino acids such as glutamate, aspartate and alanine are metabolised by cells to yield ammonium. The pH up-shift feed medium may contain glutamate, aspartate and/or alanine.

Alternatively or additionally, the pH up-shift may comprise addition of alkaline agents (bases) such as NaOH, $Na_2CO_3$, or $NaHCO_3$ to the culture medium. Alkaline agents may be referred to as bases, alkalis, and alkali salts.

Alternatively or additionally, the pH up-shift may comprise allowing the cell culture to accumulate cellular metabolites that increase the pH of the culture medium.

Alternatively or additionally, the pH up-shift may comprise removing dissolved $CO_2$ from the culture medium, for example by stripping $CO_2$ from the bioreactor. Stripping $CO_2$ from the bioreactor causes dissolved $CO_2$ to leave the culture medium. As the pH of the culture medium is dependent on the balance of dissolved $CO_2$ and bicarbonate ($HCO_3^-$), removing dissolved $CO_2$ from the culture medium can alter the pH of the culture medium.

In some embodiments comprising addition of a pH up-shift feed medium and/or allowing the cell culture to accumulate metabolites that increase the pH of the culture medium, the process does not comprise an increase in pH at a rate faster than 0.15, 0.20, 0.25, or 0.5 pH units per 24 hours.

In some embodiments comprising addition of a pH up-shift feed medium and/or allowing the cell culture to accumulate metabolites that increase the pH of the culture medium, the process does not also comprise addition of concentrated solutions of alkaline reagents (bases), such as NaOH, $Na_2CO_3$, $NaHCO_3$, to the culture medium. Concentrated solutions of alkaline reagents (bases) are those having a concentration above, for example, 0.5, 0.6, 0.7, 0.8, 0.9, or 1.0 M. Processes in which the pH up-shift does not involve addition of concentrated solutions of base may advantageously minimise increases in culture osmolality.

Adding a pH up-shift feed medium is advantageous for the fed-batch processes of the invention, because it efficiently enables both feeding of the cell culture and increasing of the pH of the cell culture in a single process step. The addition of a pH up-shift feed medium over a period of time also facilitates a gradual increase in pH over a period of time, which may be advantageous as discussed above.

The processes of the invention comprise inoculating cells into a culture medium. Inoculating cells into a culture medium refers to adding one or more cells, or a population of cells, into sterile culture medium. Inoculating may also be referred to as seeding. In the context of culture process duration and timings, the inoculation of cells into the culture medium defines Day 0 of the process.

The processes of the invention may be fed-batch processes (Whitford, 2006). A fed-batch process is a cell culture process, or fermentation process, in which cells are cultured in a culture vessel, or bioreactor, with one or more nutrients necessary for cell growth or product formation added to the bioreactor during the culture process. Nutrients can be added to the culture vessel either continuously or intermittently. Nutrients may be added in the form of a feed medium. Nutrients include sugars and amino acids, as well as vitamins, nucleosides, organic chemical compounds, and inorganic metal salts. A feed medium may comprise sugar (mono- or disaccharide), amino acids, vitamins, nucleosides, organic chemical compounds, and inorganic metal salts. The cells remain in the bioreactor throughout the cell culture process, until the cells and or cell products are harvested.

By contrast, a batch process is a cell culture process in which the cells and all necessary culture medium components are added to the culture vessel at the beginning of the fermentation process and no nutrients are subsequently added to the culture vessel. Unlike a fed-batch process, in a batch process there is no addition of a feed medium to the culture. For example, in a batch process there is no addition of sugar (e.g. glucose), and/or no addition of amino acids.

The fed-batch processes of the invention are not batch processes. The fed-batch processes of the invention may comprise addition of sugars to the culture medium. The fed-batch processes of the invention may comprise addition of a feed medium to the culture medium.

The cells are inoculated into a culture medium. The culture medium may be a commercially available medium. The culture medium may be chemically defined, and protein- and serum-free, for example CD CHO AGT™ Medium (Thermo Fisher Scientific, Formula No. A15649).

In the fed-batch processes of the invention a feed medium ("feed 1") is added to the culture medium. In this context the initial culture medium may be termed a basal medium, which is supplemented with feed medium during the fed-batch culture process. The basal medium may be a chemically defined, and protein- and serum-free, for example CD CHO AGT™ Medium (Thermo Fisher Scientific, Formula No. A15649). The basal medium may be any suitable commercially available medium, including customised media, used in accordance with the supplier or manufacturer instructions.

The feed medium may comprise additional methionine, threonine, serine, tyrosine and glycine. The feed medium may comprise additional methionine, threonine, serine, tyrosine and glycine at respective concentrations in the range of about 0.5 g/l to about 1.5 g/l.

The feed medium may be added to the culture medium in the range of about 2.0 to about 3.0 wt % of the initial culture weight per day.

The feed medium may be, for example, a feed medium containing Feed Base 5 Medium (Thermo Fisher Scientific, catalogue number 074-91011DW), Feed Base 2 Medium (Thermo Fisher Scientific, catalogue number 074-91007MV), Feed Base 6 Medium (Thermo Fisher Scientific, catalogue number 074-91012MW), Minimum Essential Medium Vitamins (MEM 100x, Thermo Fisher Scientific, catalogue number 074-91008BX), CD CHO AGT™ Medium (Thermo Fisher Scientific, Formula No. A15649), and SPE (Lonza Verviers Sprl, catalogue number BESP531F) and. The feed medium may be a medium containing specific ratios of Feed Base 5 Medium, Feed Base 2 Medium, Feed Base 6 Medium, Minimum Essential Medium Vitamins, SPE and CD CHO AGT Medium. A feed medium may be prepared by combining Feed Base 5 Medium, Feed Base 2 Medium, and Feed Base 6 Medium to provide a feed medium, any of Minimum Essential Medium Vitamins, SPE and CD CHO AGT Medium may also be included in the feed medium. The feed medium may be any suitable commercially available medium, including customised media, used in accordance with the supplier or manufacturer instructions.

The fed-batch processes of the invention may further comprise addition of pH up-shift feed medium ("feed 2"). The pH up-shift feed medium may comprise nutrients that, when metabolised by the cells, increase the pH. The pH up-shift feed medium may comprise elevated levels of glutamate, aspartate and/or alanine relative to the feed medium. The pH up-shift feed medium may comprise additional lysine, threonine, serine, valine, leucine and tryptophan. The pH up-shift feed medium may comprise additional lysine, threonine, serine, valine, leucine and tryptophan at respective concentrations in the range of about 0.5 g/l to about 6.0 g/l.

The pH up-shift feed medium may be, for example, a feed medium containing Feed Base 8 Medium (Thermo Fisher Scientific, catalogue number 074-91013RW) and Feed Base 9 Medium (Thermo Fisher Scientific, catalogue number 074-91014EW). A pH up-shift feed medium may be prepared by combining Feed Base 8 Medium and Feed Base 9 Medium to provide a pH up-shift medium. The pH up-shift medium may have a pH of about 10-11. The relative proportions of Feed Base 8 Medium and Feed Base 9 Medium may be adjusted and tested for effectiveness in achieving a desired pH up-shift in any cell culture using routine techniques, for example in preparatory design of experiment processes.

The pH up-shift feed medium may have a basic (alkaline) pH relative to the culture medium. The pH up-shift feed medium may have a pH above 10.0. The pH up-shift medium may have a pH above 8.0, 9.0 or 10.0. The pH up-shift medium may have a pH of about 8.0-12.0, about 10.0-11.0, or about 10-11. The pH up-shift feed medium may have a pH of about 10.0, 10.5 or 11.0. The pH up-shift feed medium may have a pH of about 10 or about 11.

The up-shift feed medium may be added to the culture medium in the range of about 0.5 to about 1.5 wt % of the initial culture weight per day.

The fed-batch processes of the invention may comprise addition of a feed medium to the culture medium during the first culture stage, followed by addition of a pH up-shift medium to the culture medium. The feed medium may be substituted with the pH up-shift medium after a certain number of days, as discussed below. The addition of the pH up-shift medium to the culture may precede the pH up-shift by several days, as discussed below.

An additional glucose feed solution may be added to the culture to maintain an appropriate glucose concentration, for example ≥3 g/l.

The experimental examples below demonstrate that it is the pH up-shift itself that causes in the advantageous effects in the processes carried out in accordance with the invention (rather than a component of the pH up-shift medium). This is because each example of a process in accordance with the invention is compared with a control process in which the pH up-shift medium is added to the fermentation but any increase in pH is resisted by addition of $CO_2$ (see for instance the protocol described in Example 1). This means that the advantageous effects observed in Examples 2 to 9 and Example 10 process #1 are directly attributable to the pH up-shift in accordance with the processes of the invention. A pH up-shift in accordance with the processes of the invention may be carried out using any appropriate culture media.

Example 10 also demonstrates that the pH up-shift in accordance with the invention (process #1, in which the pH up-shift is followed by a second culture stage at a higher pH than the first culture stage) is advantageous compared with a process (process #2) in which there is a pH up-shift but there is no culture stage at a pH that is higher than the first culture stage (the culture stage in which the cells were inoculated into the medium, or the culture stage starting with Day 0).

In the context of culture process duration and timings, the inoculation of cells into the culture medium defines Day 0 of the process.

The processes of the invention may comprise a first culture stage having a duration of, or of at least, 3, 4, 5 or 6 days. The first culture stage may have a duration of, or of at least 1, 2, 4, 6, 8, 12, or 18 hours. The first culture stage may have a duration of 3 to 10 days, 4 to 10 days, 4 to 8 days or 4 to 6 days. The first culture stage may have a duration of, or of at least, 1, 2, 3, 4, 5, 6, 7, 8, 9, 10, 11, 12, 13, or 14 days. The first culture stage may begin with inoculation of cells into a cell culture medium. When the mammalian cells are CHO cells the first culture stage may have a duration of 6, 7, 8 or 9 days. Reference to the first culture stage having a certain duration may specifically mean that the culture is at, or is maintained at, the first pH for that duration. In this context "maintained at" may mean "continuously maintained at". That is the processes of the invention may comprise a first culture stage that comprises culturing the cells at the first pH, or maintaining the first pH, or maintaining the set-point that is set to the first pH, for or for at least 1, 2, 4, 6, 8, 12, or 18 hours; or for 3 to 10 days, 4 to 10 days, 4 to 8 days or 4 to 6 days; or for or for at least 1, 2, 3, 4, 5, 6, 7, 8, 9, 10, 11, 12, 13, or 14 days.

The processes of the invention involve a sustained pH up-shift. A sustained pH up-shift is a pH up-shift that is maintained for a certain duration. For example a sustained pH up-shift may be a pH up-shift that is maintained for at least 1 hour, or for a duration disclosed herein as the duration for the first and/or second culture stage. The processes of the invention may comprise a second culture stage having a duration of, or of at least 4, 5, or 6 days. The second culture stage may have a duration of or of at least 1, 2, 4, 6, 8, 12, or 18 hours. The second culture stage may have a duration of 3 to 10 days, 4 to 10 days, 4 to 8 days or 4 to 6 days. The second culture stage may have a duration of, or of at least, 1, 2, 3, 4, 5, 6, 7, 8, 9, 10, 11, 12, 13, or 14 days. The second culture stage may continue until the end of the process. The second culture stage may terminate with harvesting of cells and/or products expressed by the cells. When the mammalian cells are CHO cells the second culture stage may have a duration of 6, 7, 8 or 9 days. Reference to the second culture stage having a certain duration may specifically mean that the culture is at, or is maintained at, the second pH for that duration. In this context "maintained at" may mean "continuously maintained at". That is the processes of the invention may comprise a second culture stage that comprises culturing the cells at the second pH, or maintaining the second pH, or maintaining the set-point that is set to the second pH for or for at least 1, 2, 4, 6, 8, 12, or 18 hours; or for 3 to 10 days, 4 to 10 days, 4 to 8 days or 4 to 6 days; or for or for at least 1, 2, 3, 4, 5, 6, 7, 8, 9, 10, 11, 12, 13, or 14 days.

The process of the invention may be a process for culturing mammalian cells, the process comprising a first culture stage and a second culture stage, wherein the first culture stage wherein the first culture stage is at or maintained at a first pH, and the second culture stage is at or maintained at a second pH that is higher than the first pH. The first culture stage may comprise inoculating mammalian cells into a culture medium at the first pH. The process may be a fed-batch process. The process may be a process wherein the temperature is maintained at a substantially constant value. The process may be a process in which the mammalian cells are capable of expressing an antibody, The processes of the invention my comprise controlling the pH using a pH set-point, the process comprising a first culture stage, in which the set-point is set to the first pH, and a second culture stage in which the set-point is set to the second pH. The first culture stage may comprise inoculating mammalian cells into a culture medium at the first pH. The first culture stage may have a specific duration as set out above, in which the set-point is maintained at the first pH for that duration. The second culture stage may have a specific duration as set out above, in which the set-point is maintained at the second pH for that duration.

In the context of the present disclosure "culturing the cells" may refer to culturing the cells at a specific pH for a specific duration. This may more specifically refer to culturing the cells at a specific pH that is maintained for a specific duration. This may refer to culturing the cells using a specific pH set-point for a specific duration. For example reference to a second culture stage comprising "culturing the cells at a second pH" may refer to culturing the cells at the second pH for a specific duration using a set-point set to the second pH.

The processes of the invention may comprise a pH up-shift at, or starting at, Day 6-8 (144-192 hours). The processes of the invention may comprise a pH up-shift at Day 5-9 or Day 4-10. The process may comprise a pH up-shift at Day 4, 5, 6, 7, 8, 9 or 10, or after Day 4, 5, 6, 7, 8, 9 or 10. When the mammalian cells are CHO cells the process may comprise a pH up-shift at Day 6 (144 hours), 156 hours, Day 7 (168 hours), or Day 8 (192 hours).

The optimal timing of the pH up-shift may be determined in a series of preparatory, design of experiment, processes. For example, the timing of the pH up-shift may be chosen to maximise the final product titer while retaining key product quality parameters within desired ranges (e.g. retaining Critical Quality Attributes within specific ranges specified by the FDA or EMEA in its approval of a therapeutic product, see below). The timing of the pH up-shift may be determined by measuring final product titer in a series of preparatory, design of experiment, processes to determine the pH up-shift timing yielding the maximal product titer with a product quality profile suitable for clinical application. In such cases, product titer and quality can be measured in a series of preparatory process (which may be a scaled-down version of the process) in which the timing of the pH up-shift is varied, and the timing of the pH up-shift chosen to take place on the day determined to provide a process that yields maximal product titer and a product quality profile suitable for clinical application. Product quality profile may be determined by measuring glycosylation, IEC pattern, electrophoretic pattern, Mass Spectrometry, chromatography, or Caliper data.

The product quality profile suitable for clinical application may be those approved by the FDA or EMEA for a particular therapeutic product. For example the approved product may be required to have certain attributes in terms any or all of: size-related variants, charge-related variants, trisulfide content, Fc glycosylation, microheterogeneity, glycation, mode of action related bio-functions, sequence variants, cell-age related product modifications and process related impurities. The specific mode of action (MoA) for therapeutic products at the cellular level is usually well described. Based on the MoA, non-clinical safety data, clinical study registrations and early phase of clinical study results, a set of quality parameters for any specific drug may be well defined. For late stage drug substance production, the drug substance should maintain the similar or comparable quality in order to achieve desired therapeutical effects. Key drug substance quality parameters may differ from one drug to another. These quality parameters usually include: glycosylation, glycation, amino acid misincorporation, c-terminal lysine removal, C-terminal amidation, addition to cysteine, incorrect dissulfide pairing, trisulfide formation, deamidation, succinimide formation, sulfation, phosphorylation, Met/Trp oxidation, γ-carboxylation, β-hydroxylation, etc.

Certain attributes may have potential to affect product safety or efficacy and thereby be classified as Critical Quality Attributes (CQA) that should be controlled during production and storage. Manufacturing of therapeutic proteins such as therapeutic antibodies is designed to control the desired levels of CQAs within defined limits to provide a consistent product quality.

In the processes disclosed herein variables such as the timing of the pH-upshift, the appropriate total process duration, or the harvest time may be determined by the criteria of maximal final product titer with acceptable product quality profile for clinical application.

The fed-batch processes of the invention may comprise adding a feed medium to the culture. The feed medium may be added on Day 1-3. The feed medium may be added on Day 1-3, 1-4, 1-5 or 1-6. In the Figures the feed medium is referred to as "Feed-1".

The fed-batch processes of the invention may comprise adding a pH up-shift feed medium to the culture. The pH up-shift feed medium may be added on Day 4-14. The pH up-shift feed medium may be added on Day 4, 5, 6, or 7 of the process and on each subsequent day. The feed medium may be substituted with the pH up-shift feed medium from Day 4, 5, 6, or 7 of the process onwards. In the Figures the pH up-shift feed medium is referred to as "Feed-2". The pH up-shift feed medium may prevent a down-shift in the pH of the cell culture medium, for example by neutralising acidic metabolites produced by cells. Alternatively, the pH up-shift feed medium may increase the pH of the cell culture medium.

The fed-batch processes of the invention may comprise supplementing the culture with a glucose solution on days when the pH up-shift medium is added to the culture, in order to maintain an appropriate glucose concentration.

The processes of the invention may have a duration of at least 6 days, or at least 7, 8, 9, 10, 11, 12, 13, 14, 15, 16, 17 or 18 days. The total duration may be the duration from the day of inoculation (Day 0) to the day of harvesting of cells and/or products expressed by the cells. When the mammalian cells are CHO cells the process may have a duration of 14 days. The total number of days of the process may also be referred to as the "runtime". The runtime of the process may be selected for maximal product titre, or maximal product titre with constant product quality profile. The product quality profile may be predefined for clinical application. The product quality profile may be determined by measuring glycosylation, and/or ion exchange chromatography (IEC) pattern.

The first culture stage may have a duration of 1-5, 1-4 or 1-3 days. The pH up-shift may have a duration of about 10 or 30 minutes, or about 1, 2, 3, 4, 5, 6, 7, 8, 12, 24, 36, 48, 52, or 60 hours, or may have a duration of about 2-72, 2-60, 2-52, 2-48, 8-52, 12-52, 12-48, 24-52 or 24-48 hours. The pH up-shift may have a duration of at least about 10 or 30 minutes, or at least about 1, 2, 3, 4, 5, 6, 7, 8, 12, 24, 36, 48, 52, or 60 hours, or may have a duration of at least about 2-72, 2-60, 2-52, 2-48, 8-52, 12-52, 12-48, 24-52 or 24-48 hours. The second culture stage may have a duration of about 4, 5, 6, 7, 8, 9, 10, 11, 12, 13, or 14 days, or about 4-14, 5-14, 6-14, 7-14, or 8-14 days.

The processes may comprise a harvest step. In the harvest step the cells and/or product are harvested. The harvest step terminates the process. The harvest step may be on Day 10-18, for example on Day 14.

The timing of the harvest step may be determined by measuring cell viability daily. The harvest step may be carried out on the first day in the process in which cell viability is below 85%, 80%, 75% or 70%.

The timing of the harvest step in the process of the invention may be determined by measuring lactate accumulation in a control process. The control process is identical to the process of the invention except that the first pH is maintained throughout the process (throughout both the first and second culture stages). Lactate is measured daily in the control process. The harvest step may be carried out on the Day number corresponding to the first day in the second culture stage of the control process after which at least 4, at least 5, or at least 6 consecutive daily increases in lactate have been measured. The additional criterion may be applied that the harvest step may be only carried out on a day on which no increase in lactate is measured in the process of the invention relative to the previous day.

The timing of the harvest step may be determined by measuring product titer. The timing of the harvest step may be determined by measuring final product titer in a series of preparatory, design of experiment, processes to determine which timing yields the maximal product titer with a product quality profile suitable for clinical application. In such cases, product titer and quality can be measured daily in a preparatory process (which may be a scaled-down version of the process of the invention, or may be identical to the process of the invention), and the harvest step chosen to take place on the day with highest product titer with a product quality profile suitable for clinical application.

The timing of the harvest step may be determined by measuring product quality. Product quality can be measured in terms of glycosylation (e.g. galactosylation, high mannose structure) or in terms of an in vitro or in vivo activity having a threshold value beyond which the product is non-optimal. In such cases the product quality can be measured daily in a preparatory process (which may be a scaled-down version of the process of the invention, or may be identical to the process of the invention), and the harvest step takes place on the day before the day that product quality was determined to be non-optimal in the preparatory process.

The temperature of the processes of the invention may be maintained at a substantially constant value.

When the temperature is maintained at a substantially constant value there is no significant temperature shift. A significant temperature shift may be defined as a shift of about 0.5, 1.0, 1.5, 2.0, 3.0, 4.0, or 5.0° C. or more. A substantially constant value may be within ±0.1° C., ±0.2° C., ±0.3° C., ±0.4° C., ±0.5° C., ±1.0° C., ±1.5° C., or ±2.0° C. of a target value. A target value may be 35.0, 35.5, 36.0, 36.5, 37.0, or 37.5° C.

A temperature of substantially constant value may be 36.0-37.0° C. That is, the temperature may be maintained between the values of 36.0° C. and 37.0° C. Similarly, a temperature of substantially constant value may be 36.4-36.6° C. A temperature of substantially constant value may be 36.5° C. The temperature may be measured using an on-line temperature sensor in the bioreactor.

Maintaining the temperature of the process at a substantially constant value may advantageously avoid issues caused by a significant temperature shift during the process. Reduction of temperature in cell culture processes for the production of recombinant proteins may cause undesired changes in product quality (e.g. changes in glycosylation), or may cause a loss of cellular productivity. Reduction in temperature may reduce the Integral Viable Cell Density, which is an indicator of cellular productivity and therefore generally correlates with final product titer.

The mammalian cells may be recombinant cells. Recombinant cells may comprise a nucleic acid sequence encoding a heterologous protein. The mammalian cells may be CHO cells, more specifically recombinant CHO cells. The mammalian cells may be CHO K1. The mammalian cells may be CHO K1SV. The mammalian cells may be BHK cells, more specifically recombinant BHK cells. The mammalian cells may be BHK-21 cells. The mammalian cells may be PER.C6 cells. The mammalian cells may be from a myeloma cell line. The mammalian cells may be human cell lines, such as HEK293 and its derivatives and PER.C6. The mammalian cells may be capable of expressing an antibody. The mammalian cells may comprise a nucleic acid encoding an antibody. The nucleic acid encoding the antibody may be operably linked to a constitutive promoter, or to an inducible promoter. The antibody may be a multi-specific antibody, an antibody fragment, an antibody fragment with multispecific functions, a fusion antibody, or a fusion antibody fragment. The antibody may be a monoclonal antibody. The antibody may be a therapeutic antibody. The antibody may be a bispecific antibody. The antibody may be a humanized antibody. The antibody may be anti-Ang2NEGF-CrossMab (Schaefer 2011; Fenn 2013).

The processes may be processes for producing a product, wherein the product is expressed by the mammalian cells.

The mammalian cells may be engineered to express the product. Expression systems, methods, and vectors for genetically engineering cells to express a protein of interest are well known to those skilled in the art; for example, various techniques are illustrated in Sambrook et al., Molecular Cloning: A Laboratory Manual 3 ed. (2001). The mammalian cells may be engineered to express the product using the GS Gene Expression System (Lonza Biologics plc, Slough UK).

The product may be a recombinant protein. The product may be an antibody. The antibody may be a multi-specific antibody, an antibody fragment, an antibody fragment with multispecific functions, a fusion antibody, or a fusion antibody fragment. The antibody may be a monoclonal antibody. The antibody may be a therapeutic antibody. The antibody may be a bispecific antibody. The antibody may be a bivalent bispecific antibody, such as a CrossMAb antibody (Schaefer, et al. 2011; Fenn et al. 2013). The antibody may be a biologically functional fragment of an antibody. Antibody fragments include Fab, Fab', F(ab')2, scFv, dAb, complementarity determining region (CDR) fragments, linear antibodies, single-chain antibody molecules, minibodies, diabodies and multispecific antibodies formed from antibody fragments.

The product may be a bivalent bispecific antibody that binds to Ang2 and VEGF. The product may be a bivalent bispecific CrossMab antibody that binds to Ang2 and VEGF. The product may be the antibody anti-Ang2NEGF-CrossMab (Schaefer, et al. 2011; Fenn et al. 2013). The product may be Vanucizumab, that is, the product may be the antibody anti-Ang2NEGF-CrossMab having the INN Vanucizumab. The product may be the anti-Ang2NEGF-CrossMab antibody described in WO 2011/117329, or may be an antibody having the heavy and light chain CDR amino acid sequences, or having the VH and VL domain amino acid sequences, of the first and second antigen-binding sites of the anti-Ang2NEGF-CrossMab described in WO 2011/117329, or a fragment of the anti-Ang2NEGF-CrossMab described in WO 2011/117329. The product may be an antibody having the heavy and light chain CDR amino acid sequences, or having the VH and VL domain amino acid sequences, of the first and second antigen-binding sites of Vanucizumab, or a therapeutically active fragment of Vanucizumab. The product may be a monoclonal antibody that binds to CSF-1R. The product may be the anti-CSF-1R antibody having the INN Emactuzumab. The product may be an anti-CSF-1R antibody described in WO 2011/070024, or may be an antibody having the heavy and light chain CDR sequences, or VH and VL domain amino acid sequences, of an antibody described in WO 2011/070024 (or of Emactuzumab), or a fragment of an anti-CSF-1R antibody described in WO 2011/070024 (or of Emactuzumab). Alternatively, the product may be a therapeutic protein, peptide or enzyme. The product may be recombinant human glucuronidase, recombinant human acid alpha glucosidase, or recombinant human insulin. The processes may be process for producing an antibody that is not an anti-TNFα antibody, or may be a process that is not a process for producing an anti-TNGα antibody.

Therapeutic antibodies include, without limitation anti-VEGF antibodies; anti-Ang2 antibodies; anti-CSF-1R antibodies; anti-HER2 antibodies anti-CD20 antibodies; anti- IL-8 antibodies; anti-CD40 antibodies, anti-CD11a antibodies; anti-CD11b antibodies; anti-CD11c antibodies; anti-CD18 antibodies; anti-IgE antibodies; anti-Apo-2 receptor antibodies; anti-Apo2:/TRAIL antibodies; anti-Tissue Factor (TF) antibodies; anti-human $\alpha4\beta7$ integrin antibodies; anti-EGFR antibodies; anti-CD3 antibodies; anti-CD25 antibodies; anti-CD4 antibodies; anti-CD52 antibodies; anti-Fc receptor antibodies; anti-carcinoembryonic antigen (CEA) antibodies; antibodies directed against breast epithelial cells; antibodies that bind to colon carcinoma cells; anti-CD38 antibodies; anti-CD33 antibodies; anti-CD22 antibodies; anti-EpCAM antibodies; antiGpIIb/IIIa antibodies; anti-RSV antibodies; anti-CMV antibodies; anti-HIV antibodies; anti-hepatitis antibodies; anti-CA 125 antibodies; anti-$\alpha v\beta3$ antibodies; anti-human renal cell carcinoma antibodies; anti-human 17-1 A antibodies; anti-human colorectal tumor antibodies; anti-human melanoma antibody R24 directed against GD3 ganglioside; anti-human squamous-cell carcinoma; and anti-human leukocyte antigen (HLA) antibodies, anti-HLA DR antibodies; anti-IgE antibodies; anti-HER3 antibodies; anti-HER4 antibodies; anti-DR5 antibodies; anti-ICAM antibodies; antiVLA-4 antibodies; antiVCAM, antibodies, and anti-IL17A antibodies.

The product may be a protein, or an antibody, which is not Epo-Fc.

The processes of the invention may further comprise a step of isolating the product, or purifying the product. The step of isolating or purifying the product may comprise ion exchange chromatography. The step of isolating or purifying the product may comprise loading a composition comprising the product onto an ion exchange chromatography material, optionally washing the ion exchange chromatography material, and eluting the product from the ion exchange chromatography material. The composition comprising the product may comprise culture medium from the cell culture, and/or may comprise the mammalian cells, which may be lysed mammalian cells. The method of isolating or purifying the product may comprise a step of preparing a composition comprising the product. The step of preparing a composition comprising the product may comprise harvesting the cells, and/or lysing the cells, and/or harvesting cell culture medium. The step of preparing a composition comprising the product may comprise protein A chromatography. The step of preparing a composition may comprise lyophilising the product. The step of preparing a composition may comprise formulating the product in a pharmaceutically acceptable carrier (e.g. physiological saline) and/or formulating the product in a solution comprising one or more pharmaceutical excipients.

The invention further provides products and compositions produced by the processes of the invention.

The processes of the invention may avoid excessive accumulation of undesirable metabolites such as lactate and ammonium. The processes of the invention may improve maintenance of moderate $pCO_2$ levels and/or lower culture osmolality.

The process of the invention may be a process having an improved parameter relative to a control process, wherein the control process is identical to the process of the invention except that the first pH is maintained throughout the process (throughout both the first and second culture stages). For example, the control process may be a process in which the pH in the first culture stage is 7.00 and the pH in the second culture stage is 7.00.

The parameter may be determined at the harvest step, or on the day of the harvest step. When the mammalian cells are CHO cells the parameter may be determined on Day 14.

The process of the invention may be a process in which cell viability is at least 10%, 15% or 20% higher than a control process.

The process of the invention may be a process in which lactate levels are at least 10%, 20%, 30%, 40%, or 50% lower than a control process.

The process of the invention may be a process in which ammonium levels are at least 10%, 20%, 30%, 40%, 50%, 60%, 70% or 80% lower than a control process.

The process of the invention may be a process in which the product titer is at least 5%, 10% or 15% higher than a control process.

The process of the invention may be a process in which osmolality is at least 5% lower than a control process. The process of the invention may be a process in which osmolality is below 500 Osm/kg at the harvest step.

The processes of the invention are improved compared with processes in which the pH is maintained at the same value throughout the process (as in Example 1), as shown by Examples 2 to 9 and the accompanying figures.

The processes of the invention are also improved compared with processes comprising a pH down-shift from an initial value followed by a pH up-shift towards the initial value, as shown by Example 10 processes #1 and #2. Processes comprising a pH down-shift from an initial value followed by a pH up-shift towards the initial value are disclosed in U.S. Pat. No. 8,765,413.

The invention further provides a method of extending the longevity of a mammalian cell culture, the method comprising the process of the invention as described above. The invention provides a method of increasing cell viability in a mammalian cell culture, the method comprising the process of the invention as described above. The invention provides a method of increasing Integral Viable Cell Density (IVCD) in a mammalian cell culture, the method comprising the process of the invention as described above. The invention provides a method of reducing lactate accumulation in a mammalian cell culture, the method comprising the process of the invention as described above. The invention provides a method of reducing ammonium accumulation in a mammalian cell culture, the method comprising the process of the invention as described above. The invention provides a method of improving $pCO_2$ profile in a mammalian cell culture, the method comprising the process of the invention as described above. The invention provides a method of reducing osmolality in a mammalian cell culture, the method comprising the process of the invention as disclosed above.

The invention further provides the use of a pH up-shift feed medium, or of an pH-increasing agent (e.g. alkaline agent, or base), for extending longevity of a mammalian cell culture; for increasing cell viability in a mammalian cell culture; for increasing IVCD in a mammalian cell culture; for reducing lactate accumulation in a mammalian cell culture; for reducing ammonium accumulation in a mammalian cell culture; for improving $pCO_2$ profile in a mammalian cell culture; or for reducing osmolality in a mammalian cell culture, by performing a method or process of the invention as disclosed above. The process comprises adding the pH up-shift medium or pH-increasing agent to the mammalian cell culture to increase the pH from the first pH to the second pH. That is, where the invention is the use of a pH up-shift medium or pH-increasing agent to achieve a particular purpose the use involves adding the pH up-shift medium or pH-increasing agent to the culture medium of the mammalian cell culture to effect the pH up-shift that occurs between the first and second culture stages. The invention further provides the use of a pH up-shift feed medium, or of an pH-increasing agent (e.g. alkaline agent, or base), for increasing product titer in a mammalian cell culture. For example the invention provides the use of a pH-increasing agent for increasing product titer in a process for culturing mammalian cells as disclosed herein, wherein the product is expressed by the mammalian cells, for example a recombinant protein such as an antibody. The increase in product titre is relative to a mammalian cell culture in which no pH-increasing agent is added to the mammalian cell culture. The invention provides the use of a pH-increasing agent for increasing product titer in a process for producing a product (such as a recombinant protein product) as disclosed herein. In a second aspect the invention provides a process for culturing mammalian cells, the process comprising a first culture stage, comprising culturing the cells at a first pH and a second culture stage comprising culturing the cells at a second pH, wherein the second pH is higher than the first pH and wherein the temperature of the process is maintained at a substantially constant value.

In a third aspect the invention provides a process for culturing mammalian cells, which mammalian cells are capable of expressing an antibody, the process comprising a first culture stage comprising inoculating mammalian cells into a culture medium at a first pH and culturing the cells at the first pH and a second culture stage comprising culturing the cells at a second pH that is higher than the first pH.

The second and third aspects of the invention may include any of the features of the processes of the invention discussed above in relation to the first aspect of the invention.

Each and every compatible combination of the embodiments described above is explicitly disclosed herein, as if each and every combination was individually and explicitly recited, except where such a combination is clearly impermissible or expressly avoided.

The section headings used herein are for organizational purposes only and are not to be construed as limiting the subject matter described.

Various further aspects and embodiments of the present invention will be apparent to those skilled in the art in view of the present disclosure.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. For example a pH of about 7.2 may be a pH of 7.2.

A pH value that is "about" a certain figure may be interpreted according to the degree of precision with which it has been expressed. For example a pH of "about 7.0" may refer to pH 6.95-7.05, whereas a pH of "about 10" may refer to pH 9.5-10.5.

A pH value that is relatively high on the pH scale is relatively alkaline and a pH value that is relatively low is relatively acidic. Thus a higher pH in the context of the present disclosure refers to a more alkaline pH.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above. The examples should not be construed as to limit the scope of this invention. The examples are included for purposes of illustration and the invention is limited only by the claims. Further aspects and embodiments will be apparent to those skilled in the art. All documents mentioned in this text are incorporated herein by reference.

EXAMPLES

The following examples, including the experiments conducted and the results achieved, are provided for illustrative purposes only and should be construed to include all possible embodiments along with the full scope of equivalents to which such claims are entitled.

Cell-Line, Culture Medium, and Culture Process

In all of the following examples CHO K1SV, a cell-line derived from Chinese Hamster Ovary (CHO) cells, was used as the host cell-line (The GS Gene Expression System, Lonza Brochures, Lonza Biologics plc, Slough UK). The GS expression vector system was provided by Lonza Biologics. In Examples 1-9 and 11, CHO K1SV cells were engineered to express a bi-specific monoclonal antibody, anti-Ang2NEGF-CrossMab (anti-A2V; Vanucizumab, or RG7221; described in WO 2011/117329) recognizing VEGF-A with one arm and Ang2 with the other (Schaefer, et al. 2011; Fenn et al. 2013). In Example 10, CHO K1SV cells were engineered to express a humanized monoclonal antibody (anti-CSF-1R; Emactuzumab, or RG7155; described in WO 2011/070024) that inhibits CSF-1 receptor (CSF-1R) activation (Ries et al., 2014). Colony-stimulating factor 1 (CSF-1) and its receptor, CSF-1R, regulate the migration, differentiation, and survival of macrophages and their precursors (Hume and MacDonald, 2012).

In all cases, the commercially-available, serum-free, chemically-defined CD CHO AGT™ Medium basal medium (Thermo Fisher Scientific, Formula No. A15649) was used to culture the CHO K1SV cells. After thawing, the cells were passaged in this medium in the presence of 50 μM methionine sulfoximine (MSX; Bedford Laboratories, Bedford, Ohio) in shake flasks on a 3-4 day schedule. Passage conditions were 36.5° C., 7% $CO_2$, and 160 rpm for 125 mL and 500 mL flasks using Kuhner Shaker X platform (Adolf Kühner AG, Birsfelden, Basel, Switzerland).

The cultured cells were used to inoculate the N−1 step at about $3.0\times10^5$ cells/mL without MSX. Production bioreactors were inoculated at about $6.0\times10^5$ cells/mL without MSX. The cells were cultured in production bioreactors under fed-batch culture conditions with predefined pH, dissolved oxygen, temperature and nutrient feeding strategy.

2 L bioreactors with an initial culture volume of 1.2 L were employed, unless otherwise noted.

The temperature in the bioreactors was controlled at 36.5° C., and the stirrer speed was set to be about 213 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 25% by varying the oxygen partial pressure in the gas mixture. The pH was maintained at a defined set-point, or within a defined dead-band, by the addition of $CO_2$ or 1.0 M $NaHCO_3$, unless otherwise noted.

The feed medium (referred to as "Feed-1" in the Figures) and the pH up-shift feed medium (referred to as "Feed-2" in the Figures) included a combination of glucose, glutamine, amino acids, growth factors, nucleosides, vitamins, trace elements, and salts.

The feed medium was contained Feed Base 5 Medium (catalogue number 074-91011DW), Feed Base 2 Medium (catalogue number 074-91007MV), Feed Base 6 Medium (catalogue number 074-91012MW), Minimum Essential Medium Vitamins (MEM 100x, catalogue number 074-91008BX), CD CHO AGT™ Medium (Formula No. A15649), and SPE (Lonza Verviers Sprl, catalogue number BESP531F).

The pH up-shift feed medium contained Feed Base 8 Medium (catalogue number 074-91013RW) and Feed Base 9 Medium (catalogue number 074-91014EW).

Recipes for the feed medium and pH up-shift medium are available from Lonza Verviers Sprl.

Samples of about 10 ml were taken daily with a syringe for off-line analysis. Production duration typically lasted about 14 days.

Cell Analysis and Off-Line Measurements

Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration.

Dissolved carbon dioxide and oxygen were analyzed with a Cobas b221 analyzer (Roche Diagnostics Ltd. CH-6343 Rotkreuz, Switzerland). Osmolality was measured by freezing point depression on an Osmomat Auto Osmometer (Gonotec GmbH, Berlin, Germany).

Example-1: Control Process—Same pH Throughout (Constant pH Set-Point)

Anti-Ang2NEGF cells were grown in shake flasks and passaged several times. The production fermentation run was started with an initial cell count of approximately $6.0\times10^5$ cells/mL, at 36.5° C. and at a constant pH set-point of 7.00 with a dead-band of ±0.05 pH units. That is the process began (Day 0) with inoculation of approximately $6.0\times10^5$ cells/mL into the culture medium (CD CHO Medium AGT™ Medium) as discussed above.

Feed medium was prepared in solution and continuously added to the culture on Day 1-3, at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

The online pH set-point was 7.00±0.05, maintained using carbon-dioxide gas injection or by addition of 1M sodium carbonate. If the off-line pH measurement deviated from the online measurement by 0.05 pH unit or more, the online pH measurement was re-calibrated to be equal to the off-line pH measurement.

Process samples were taken daily from the cultures and analyzed for the required parameters.

Figure 1:
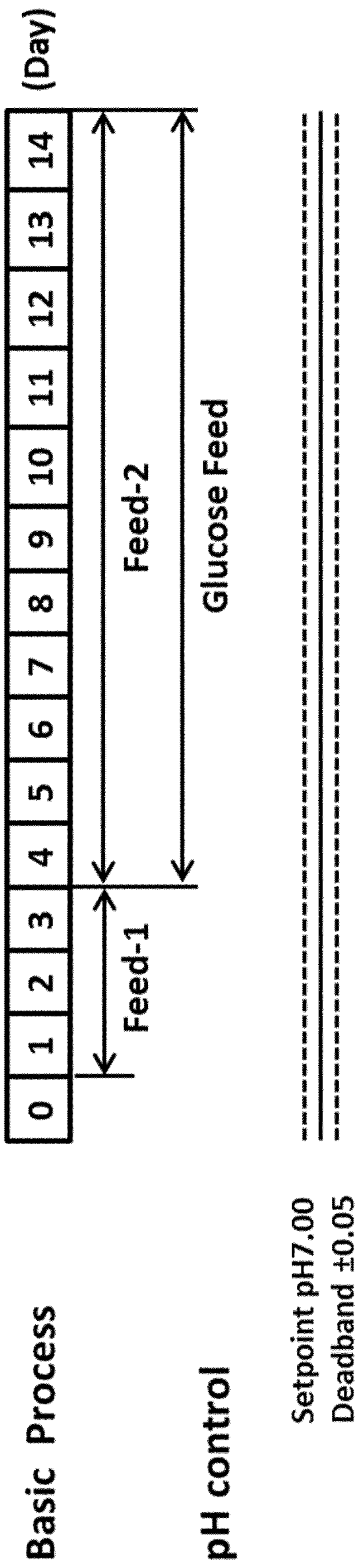
FIG. 1 shows an overview of a process for the production of an anti-Ang2NEGF bispecific antibody, in which the pH is maintained at 7.00±0.05 for the duration of the 14 day runtime.

FIG. 1 illustrates the pH set-point and dead-band settings and feed schedule for the culture process.

Example-2: pH Ramp (Δ0.20 Between 144 and 192 Hours)

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3, at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 2A illustrates the pH set-point and dead-band settings and feed schedule for the culture process. The online pH set-point was initially maintained at 7.00±0.05 using carbon-dioxide gas injection or by addition of 1M sodium carbonate. Starting from about 144 hours, the pH set-point was set to gradually increase from 7.00 to 7.20 in a pH ramp over a period of about 48 hours. At about 192 hours, the pH set-point reached pH 7.20±0.05 and was maintained at this value until the end of the production process. Process samples were taken from the cultures daily and analyzed for the required parameters.

Figure 2B:
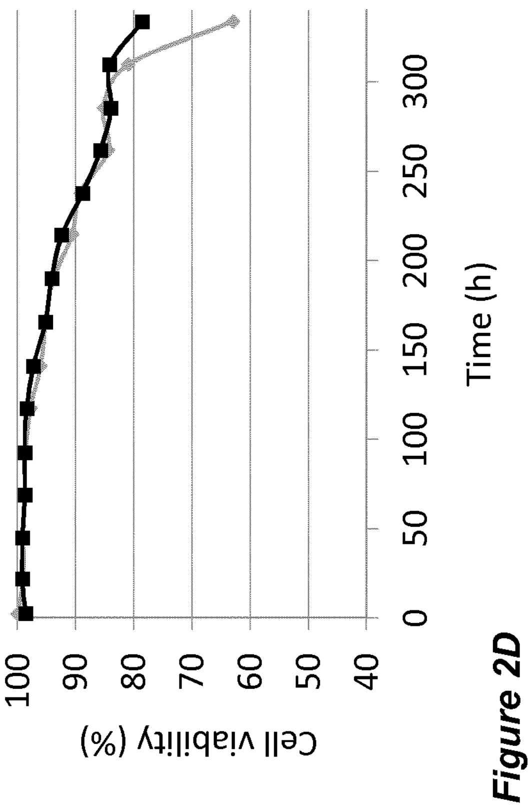
Figure 2C:
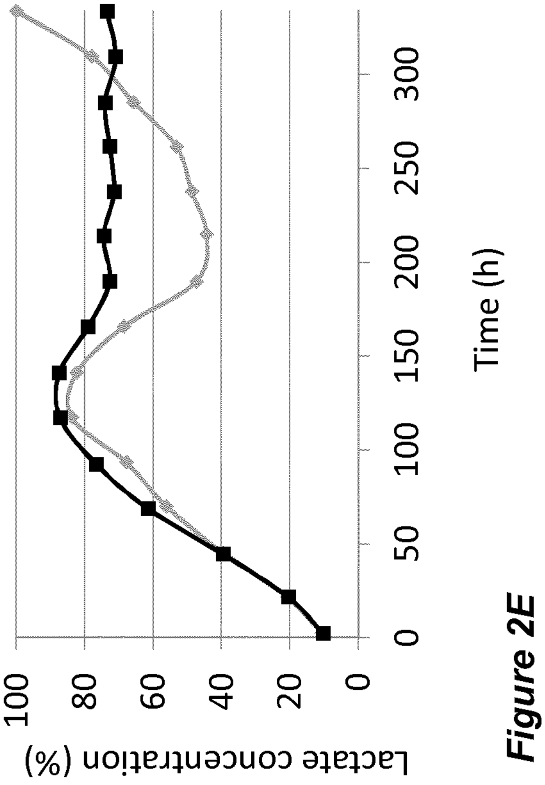
Figure 2D:
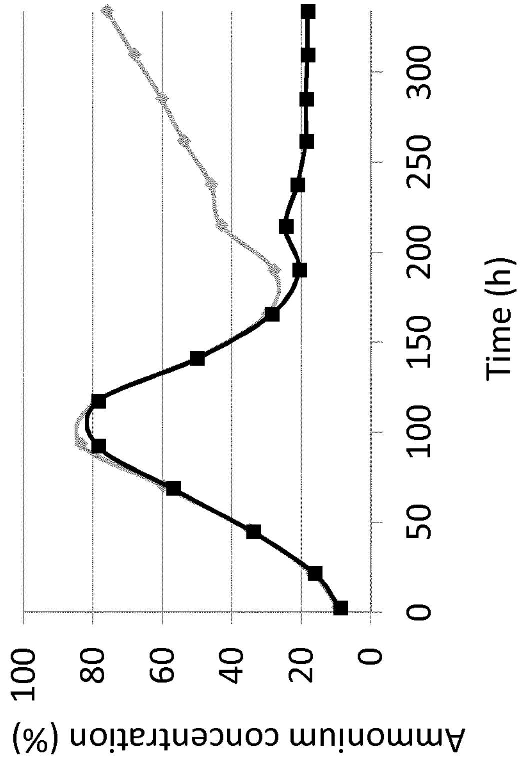
Figure 2E:
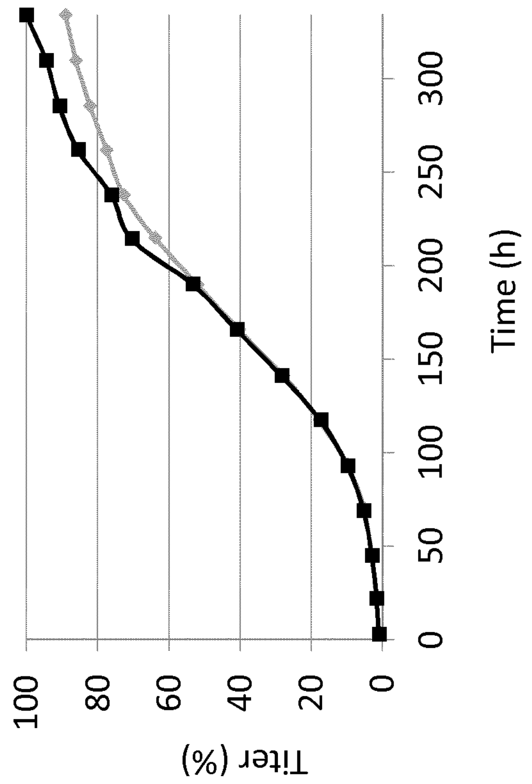
Figure 2F:
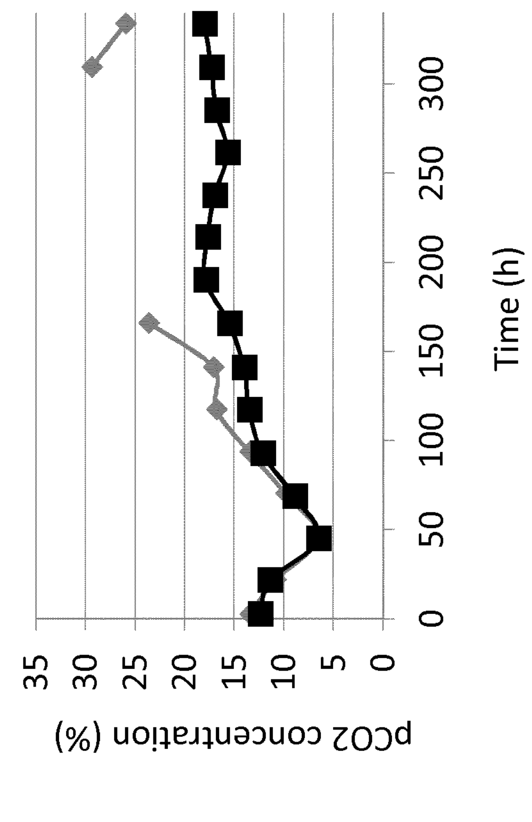
Figure 2G:
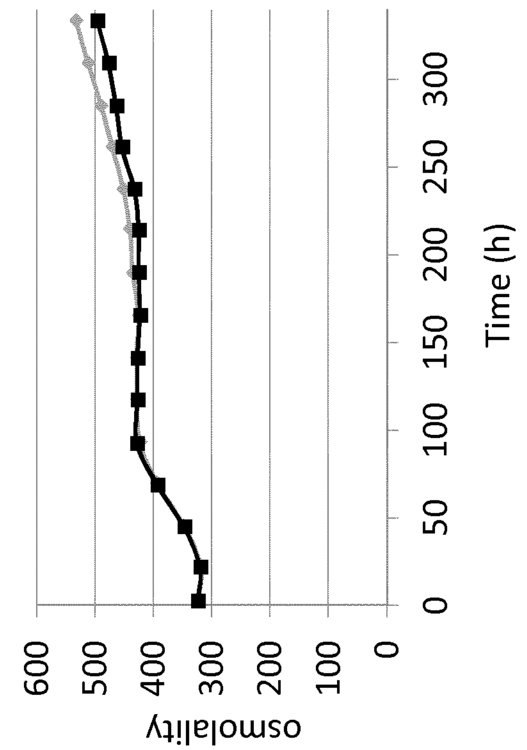

FIGS. 2B-G illustrate the effects on cell viability, lactate concentration, ammonium concentration, product titer, $pCO_2$, and osmolality during the culture process having pH settings according to FIG. 2A (black squares), as compared to a culture process having pH settings according to FIG. 1 (grey diamonds). FIG. 2B shows that at the end of the 14 day production process, cell viability in the process with the pH ramp (ΔpH 0.20 units between 144 and 192 hours) was higher than for the process without such a pH ramp. FIG. 2C shows that the process with the pH ramp lactate levels reach a high of about 88% between Day 4-5, before dropping to about 72% where they are maintained until the end of the process. At the end of the process lower amounts of lactate are produced with the pH ramp settings in comparison to the process without a pH ramp. FIG. 2D shows that ammonium levels reach a high of about 80% at approximately 100 hours, then drop to about 20% where they are maintained until the end of the process. Much lower amounts of ammonium are produced with the pH ramp settings in comparison to the process without a pH ramp. FIG. 2E shows that the end of the process, product titer in the process with the pH ramp is higher than in the process without a pH ramp. FIG. 2F shows that in the process with the pH-ramp $pCO_2$ level increased moderately but was maintained at under about 18% until the end of the process. In contrast, much higher $pCO_2$ levels were observed in the process without a pH-ramp, particularly between 160 and 320 hours. FIG. 2G shows that at the end of the process, culture osmolality in the process with the pH-ramp is lower than in the process without a pH-ramp.

Example-3: pH Ramp (Δ0.20 Between 156 and 208 Hours)

Anti-Ang2NEGF cells were grown in shake flasks and passaged several times. The production fermentation run was started with an initial cell count of about $6.0\times10^5$ cells/mL at 36.5° C. and a pH set-point of 7.00 with a dead-band of ±0.05 pH units. Feed medium was prepared in solution and was continuously added to the culture during Day 1-3 at an amount ranging from about 2.0 to about 3.0 weight % of the initial culture weight per day. pH up-shift feed medium was prepared in solution and was continuously added to the culture during Day 4-14 at an amount ranging from about 0.5 to about 1.5 weight % of the initial culture weight per day. An additional glucose feed solution was prepared and continuously added to the culture during Day 4-14 to maintain glucose concentration at about 3 g/l.

FIG. 3A illustrates the pH set-point and dead-band settings and feed schedule for the culture process. The online pH set-point was initially maintained at 7.00±0.05 using carbon-dioxide gas injection or by addition of 1M sodium carbonate. Starting from about 156 hours, the pH set-point was set to gradually increase from 7.00 to 7.20 in a pH ramp over a period of about 52 hours. At about 208 hours, the pH set-point reached pH 7.20±0.05 and was maintained at this value until the end of the production process. Process samples were taken from the cultures daily and analyzed for the required parameters.

FIGS. 3B-G illustrate the effects on cell viability, lactate concentration, ammonium concentration, product titer, $pCO_2$, and osmolality during the culture process having pH settings according to FIG. 3A (black squares), as compared to a culture process having pH settings according to FIG. 1 (grey diamonds).

Figure 3B:
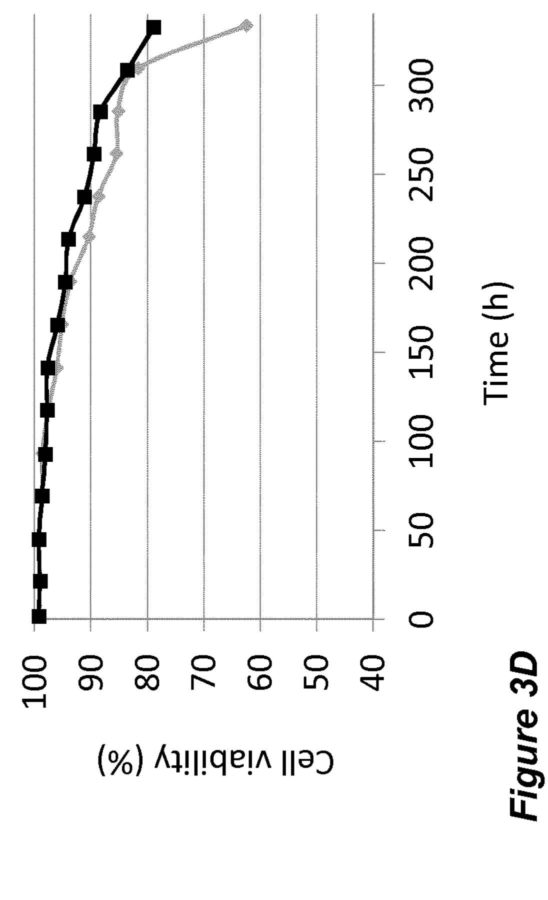
Figure 3C:
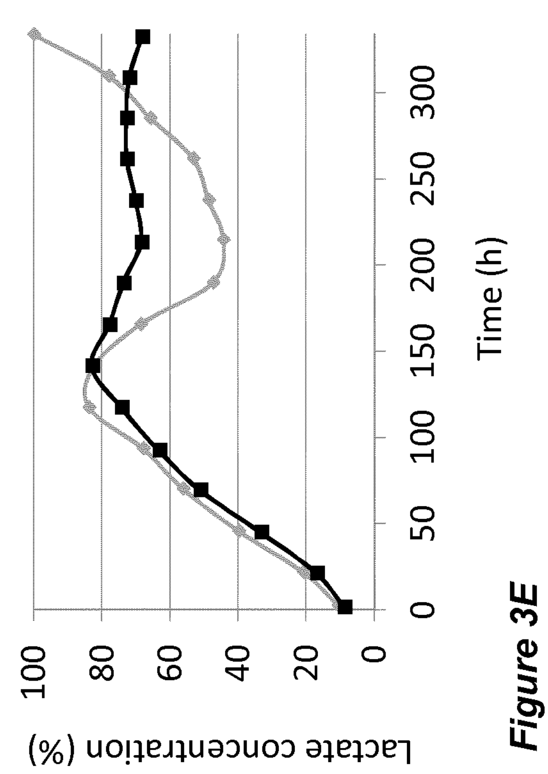
Figure 3D:
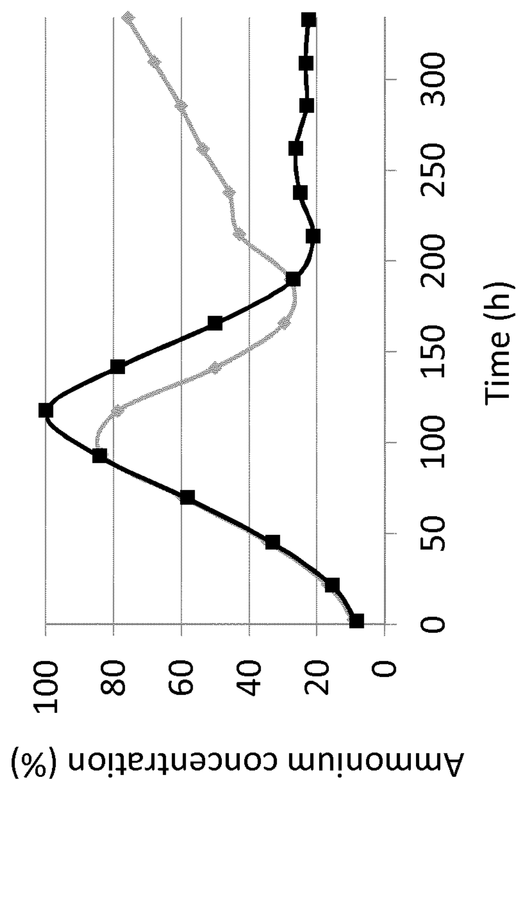
Figure 3E:
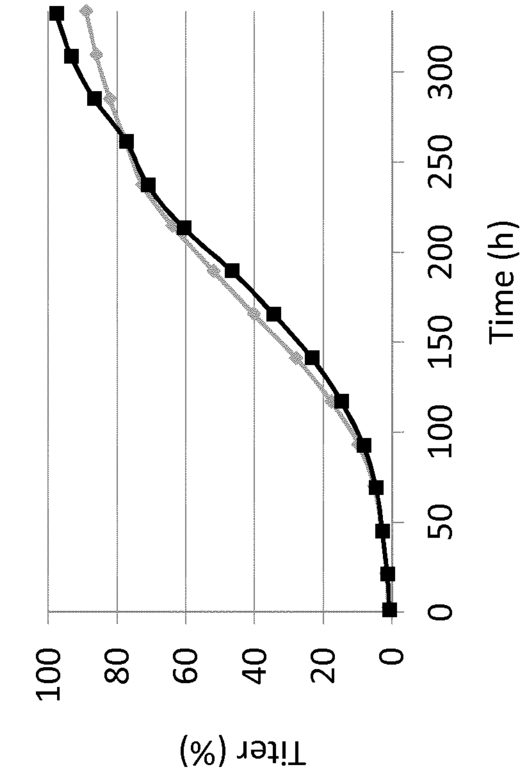

FIG. 3B shows that t the end of the 14 day production process, cell viability in the process with the pH ramp (ΔpH 0.20 units between 156 and 208 hours) was higher than for the process without a pH ramp. FIG. 3C shows that in the process with the pH ramp lactate levels reach a high of about 80% at approximately 140 hours, then drop to about 70% where they are maintained until the end of the process. At the end of the process lower amounts of lactate are produced with the pH ramp settings in comparison to the process without a pH ramp. FIG. 3D shows that in the process with the pH ramp ammonium levels reach a high of about 100% after approximately 110 hours, then drop to about 20% where they are maintained until the end of the process. Much lower amounts of ammonium are produced with the pH ramp settings in comparison to the process without a pH ramp. FIG. 3E shows that at the end of the process, product titer in the process with the pH ramp is higher than in the process without a pH ramp.

Figure 3G:
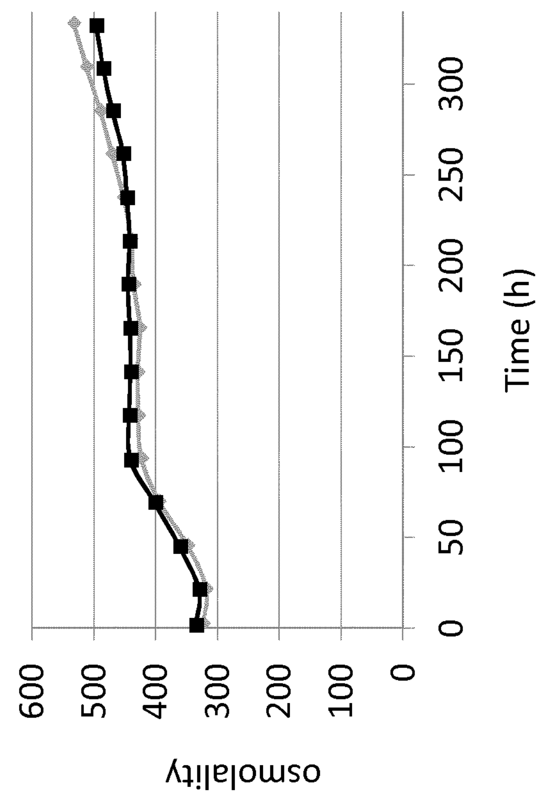
Figure 3F:
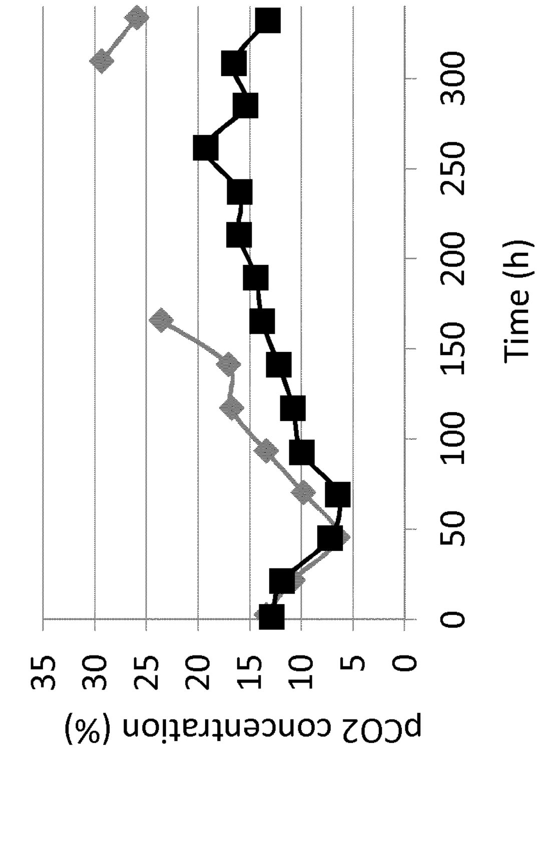

FIG. 3F shows that in the process with the pH-ramp $pCO_2$ level increased moderately but was maintained at under about 19% until the end of the process. In contrast, much higher $pCO_2$ levels were observed in the process without a pH-ramp, particularly between 160 and 320 hours. FIG. 3G shows that at the end of the process, culture osmolality in the process with the pH-ramp is lower than in the process without a pH-ramp.

Example-4: pH Ramp (40.30 Between 192 and 240 Hours)

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about 3 g/l.

FIG. 4A illustrates the pH set-point and dead-band settings and feed schedule for the culture process. The online pH set-point was initially maintained at 7.00±0.05 using carbon-dioxide gas injection or by addition of 1M sodium carbonate. Starting from about 192 hours, the pH set-point was set to gradually increase from 7.00 to 7.30 in a pH ramp over a period of about 48 hours. At about 240 hours, the pH set-point reached pH 7.30±0.05 and was maintained at this value until the end of the production process. Process samples were taken from the cultures daily and analyzed for the required parameters.

FIGS. 4B-G illustrate the effects on cell viability, lactate concentration, ammonium concentration, product titer, $pCO_2$, and osmolality during the culture process having pH settings according to FIG. 4A (black squares), as compared to a culture process having pH settings according to FIG. 1 (grey diamonds).

Figure 4B:
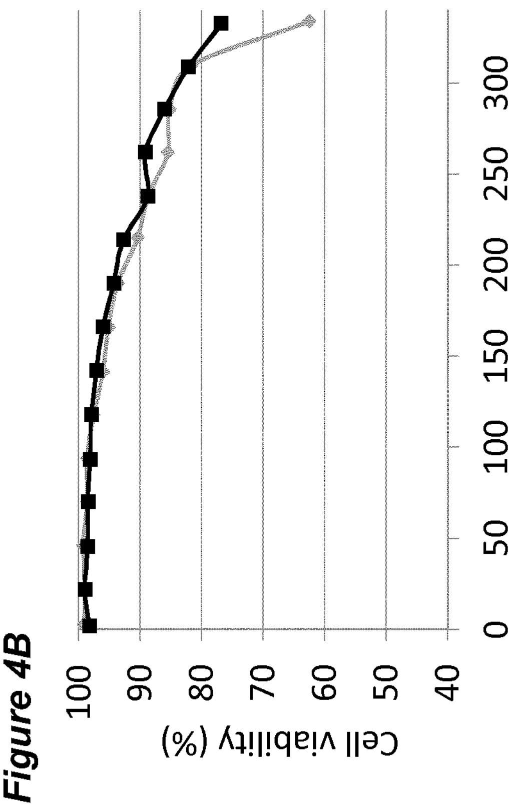
Figure 4C:
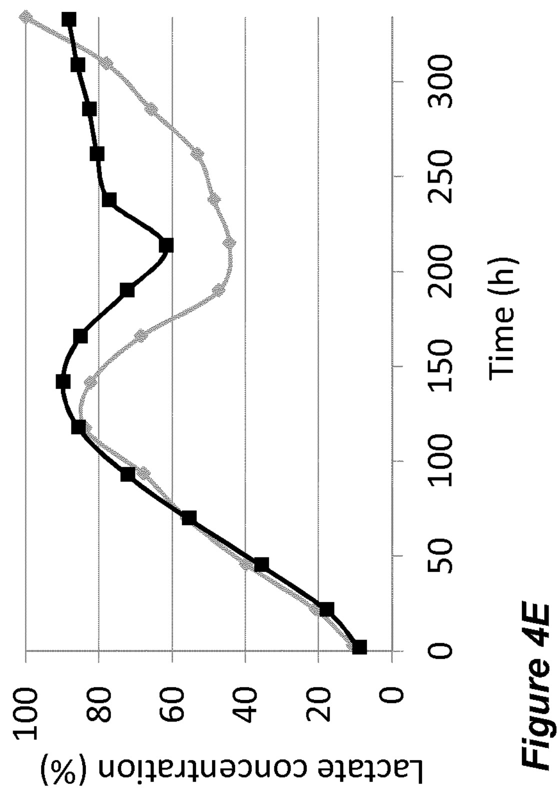
Figure 4D:
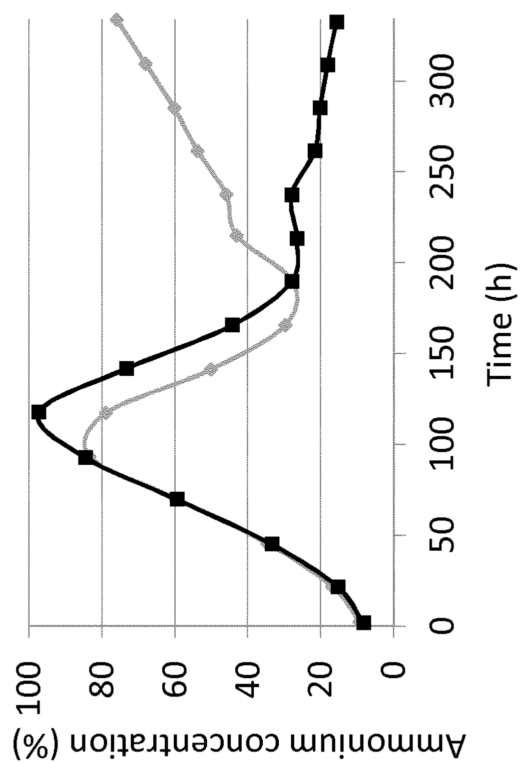
Figure 4E:
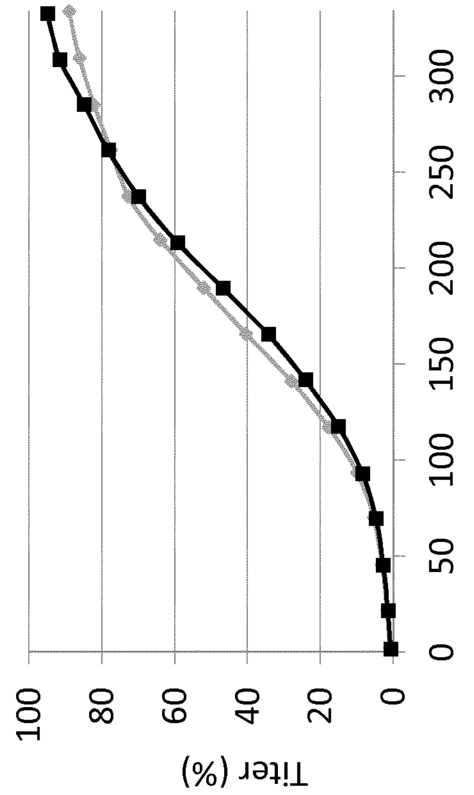
Figure 4F:
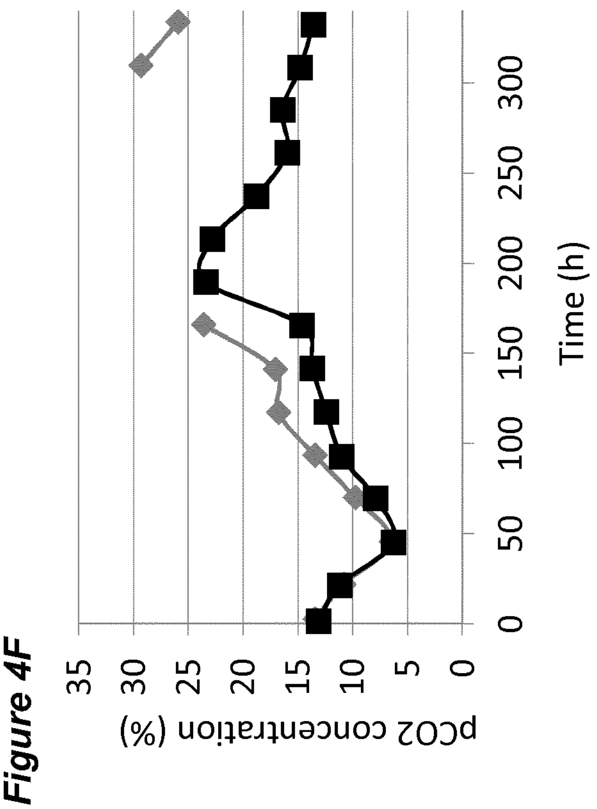
Figure 4G:
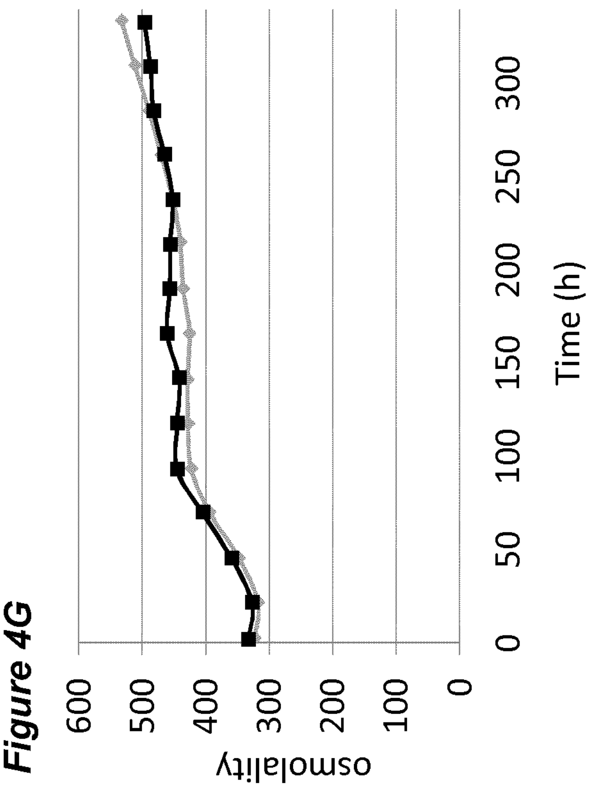

FIG. 4B shows that at the end of the 14 day production process, cell viability in the process with the pH ramp (ΔpH 0.30 units between 192 and 240 hours) is higher than for the process without a pH ramp. FIG. 4C shows that in the process with the pH ramp lactate levels reach a high of about 90% at approximately 140 hours, then drop to about 60% before gradually increasing to below 90% at the end of the process. At the end of the process lower amounts of lactate are produced with the pH ramp settings in comparison to the process without a pH ramp. FIG. 4D shows that in the process with the pH ramp ammonium levels reach a high of about 97% at approximately 110 hours, then drop rapidly to about 28% before continuing to drop to a low level of about 15% at the end of the process. Much lower amounts of ammonium are produced with the pH ramp settings in comparison to the process without a pH ramp. FIG. 4E shows that at the end of the process, product titer in the process with the pH ramp is higher than in the process without a pH ramp. FIG. 4F shows that in the process with the pH-ramp the $pCO_2$ level increased moderately to approximately 24% at around 200 hours before decreasing to less than 15% by the end of the process. In contrast, much higher $pCO_2$ levels were observed in the process without a pH-ramp, particularly between 160 and 320 hours. FIG. 4G shows that at the end of the process, culture osmolality in the process with the pH-ramp (ΔpH 0.30 units between 192 and 240 hours) is lower than in the process without a pH-ramp.

Example-5: pH Ramp (40.10 Between 192 and 240 Hours)

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 5A illustrates the pH set-point and dead-band settings and feed schedule for the culture process. The online pH set-point was initially maintained at 7.00±0.05 using carbon-dioxide gas injection or by addition of 1M sodium carbonate. Starting from about 192 hours, the pH set-point was set to gradually increase from 7.00 to 7.10 in a pH ramp over a period of about 48 hours. At about 240 hours, the pH set-point reached pH 7.10±0.05 and was maintained at this value until the end of the production process. Process samples were taken from the cultures daily and analyzed for the required parameters.

FIGS. 5B-G illustrate the effects on cell viability, lactate concentration, ammonium concentration, product titer, $pCO_2$, and osmolality during the culture process having pH settings according to FIG. 5A (black squares), as compared to a culture process having pH settings according to FIG. 1 (grey diamonds).

Figure 5B:
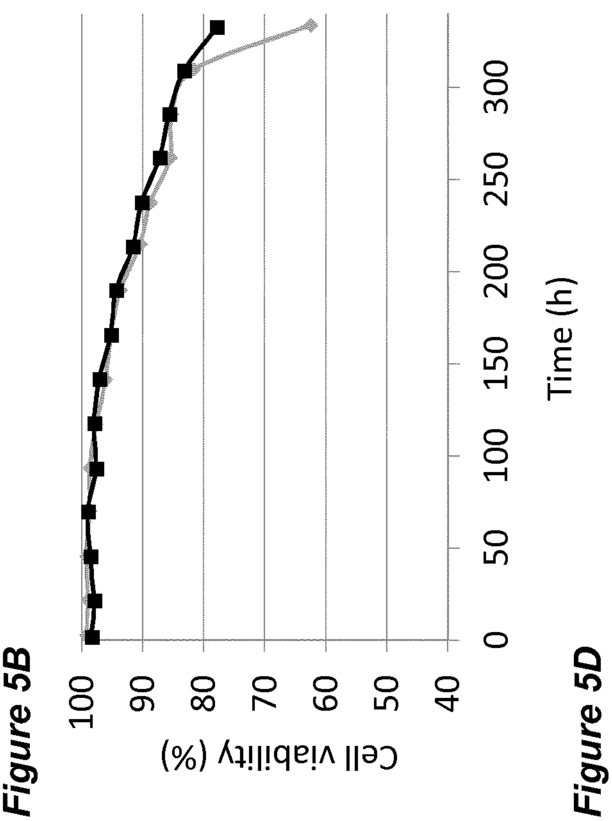
Figure 5C:
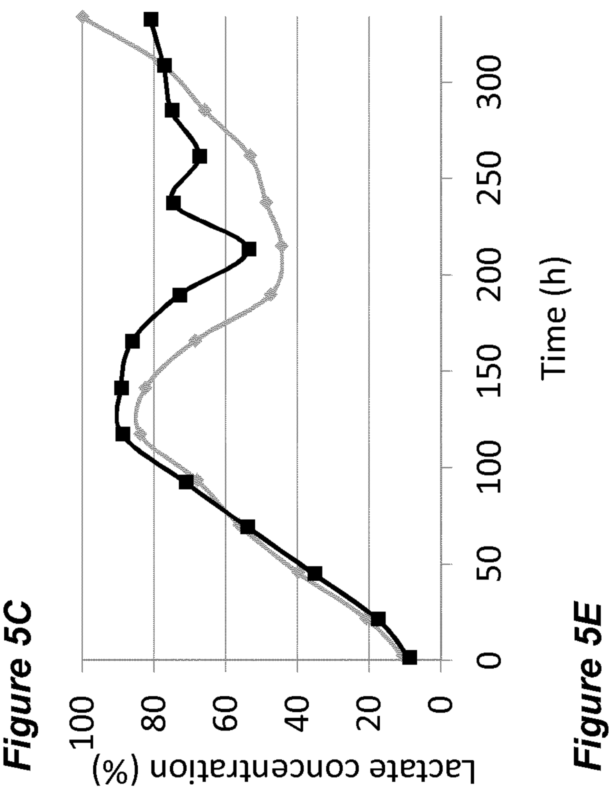
Figure 5D:
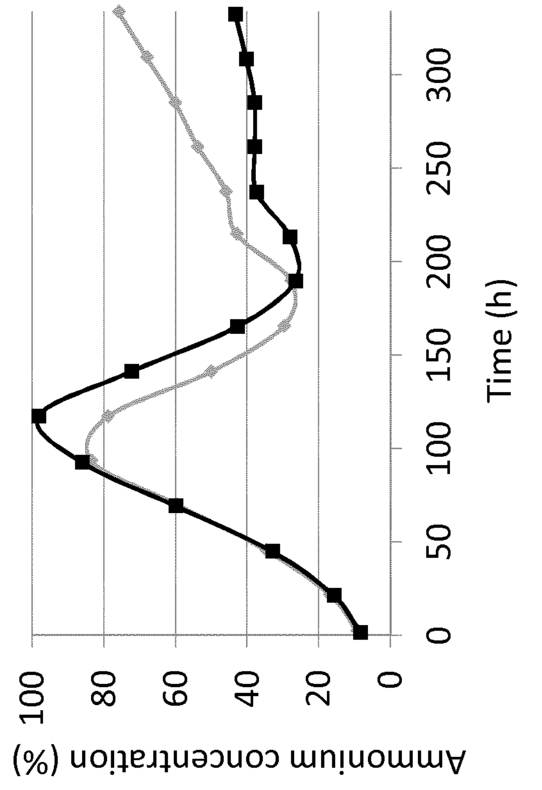
Figure 5E:
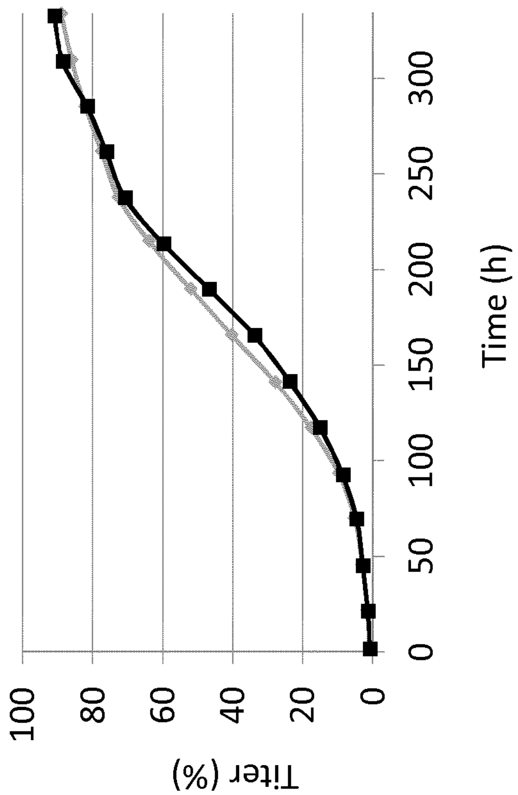
Figure 5G:
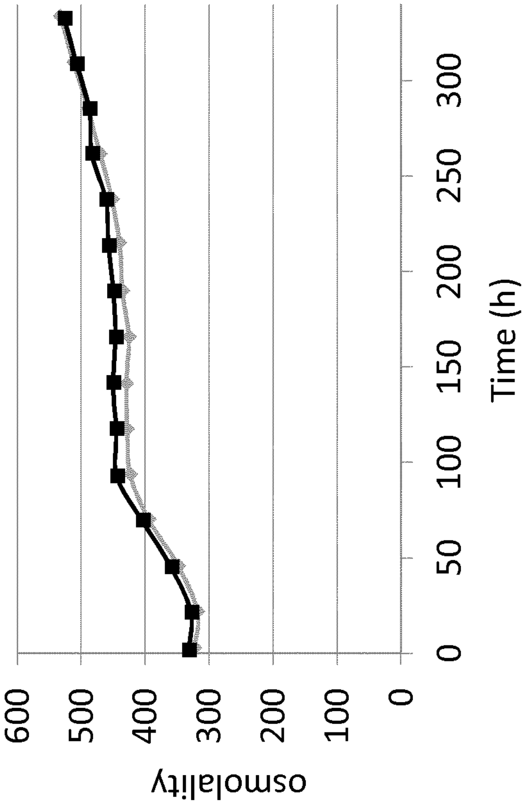
Figure 5F:
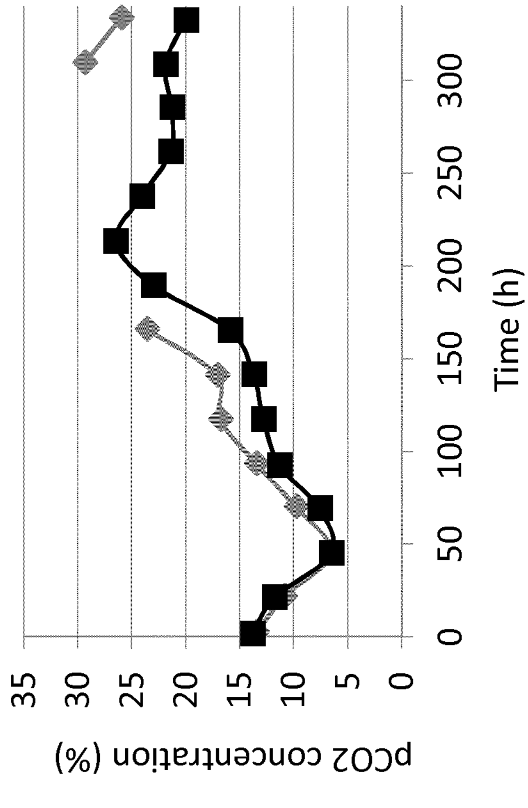

FIG. 5B shows that at the end of the 14 day production process, cell viability in the process with the pH ramp (ΔpH 0.10 units between 192 and 240 hours) was higher than in the process without a pH ramp. FIG. 5C shows that in the process with the pH ramp lactate levels reach a high of about 90% after approximately 110 hours, before dropping to about 55% and then gradually increasing to about 80% at the end of the process. At the end of the process lower amounts of lactate are produced with the pH ramp settings in comparison to the process without a pH ramp. FIG. 5D shows that in the process with the pH ramp, ammonium levels reach a high of about 97% after approximately 110 hours, before dropping rapidly to about 27% and then gradually increasing to a level of about 42% at the end of the process. Lower amounts of ammonium are produced with the pH ramp settings in comparison to the process without a pH ramp. FIG. 5E shows that at the end of the process, product titer in the process with the pH ramp is slightly higher than in the process without a pH ramp. FIG. 5F shows that in the process with the pH-ramp the $pCO_2$ level increased moderately to approximately 26% at around 200 hours before decreasing to less than 20% by the end of the process. In contrast, much higher $pCO_2$ levels were observed in the process without a pH-ramp, particularly between 160 and 320 hours. FIG. 5G shows that the end of the process, culture osmolality in the process with the pH-ramp (ΔpH 0.10 units between 192 and 240 hours) is slightly higher than in the process without a pH-ramp.

Example-6: Instant pH Up-Shift (Δ0.20 at 144 Hours)

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 6A illustrates the pH set-point and dead-band settings and feed schedule for the culture process. The online pH set-point was initially maintained at 7.00±0.05 using carbon-dioxide gas injection or by addition of 1M sodium carbonate. At about 144 hours, the pH set-point was increased in a single step from 7.00 to 7.20 with the same dead-band of pH±0.05 and was maintained at this value until the end of the production process. Process samples were taken from the cultures daily and analyzed for the required parameters.

FIGS. 6B-G illustrate the effects on cell viability, lactate concentration, ammonium concentration, product titer, $pCO_2$, and osmolality during the culture process having pH settings according to FIG. 6A (black squares), as compared to a culture process having pH settings according to FIG. 1 (grey diamonds).

Figure 6B:
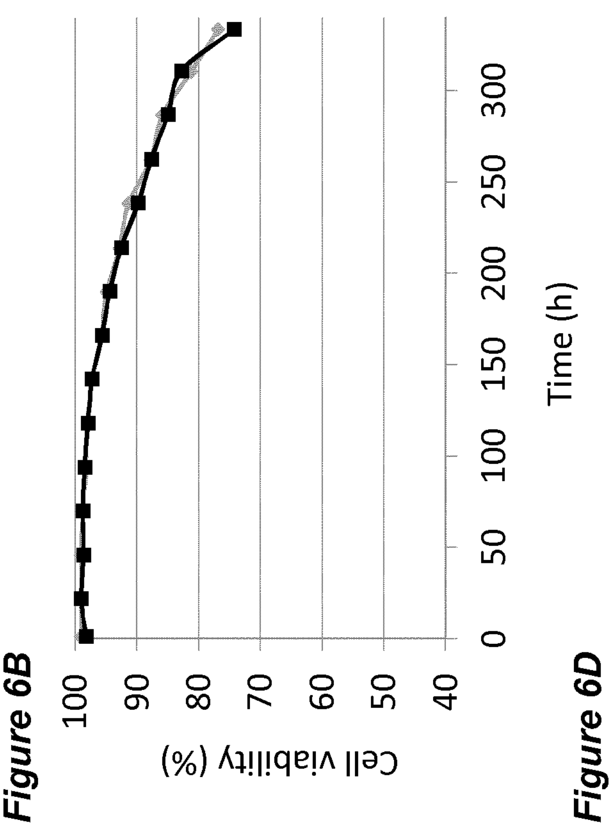
Figure 6C:
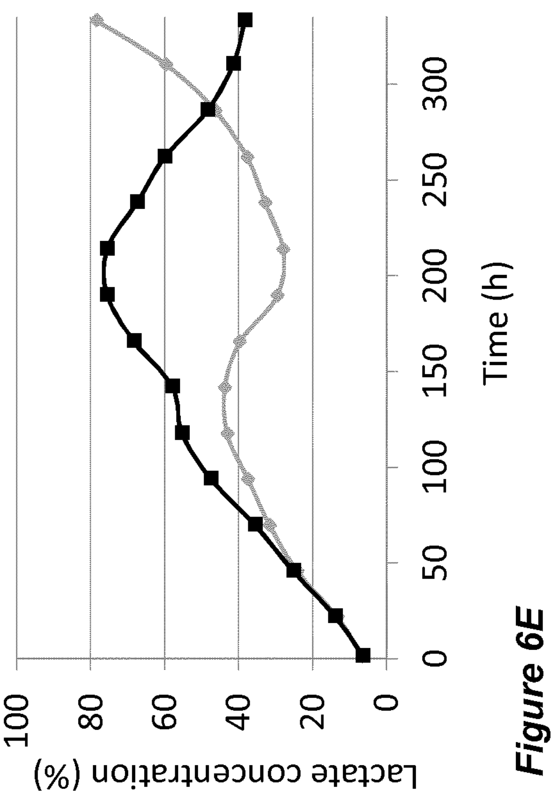
Figure 6D:
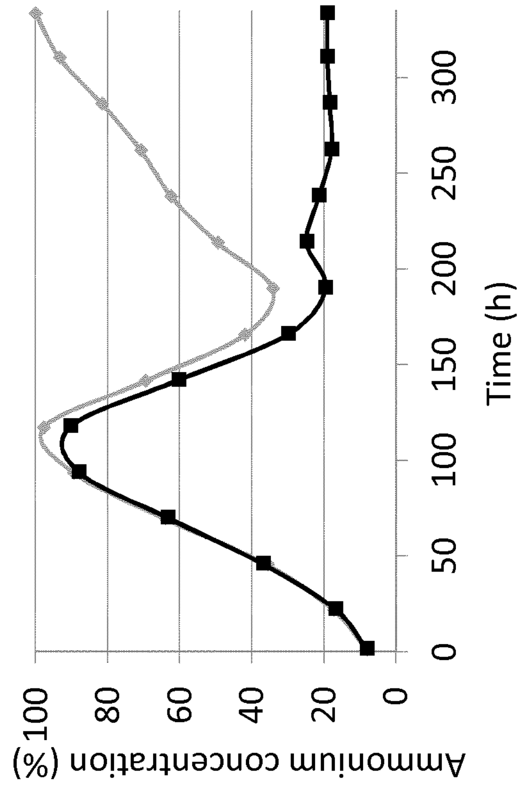
Figure 6E:
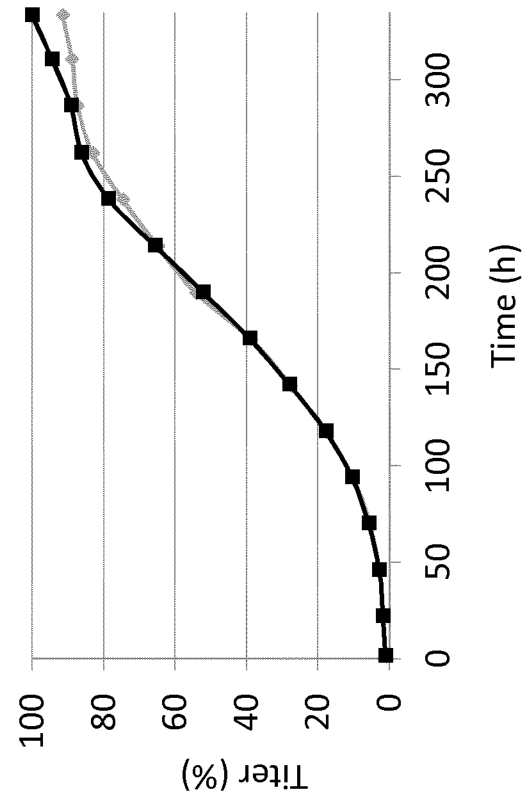
Figure 6G:
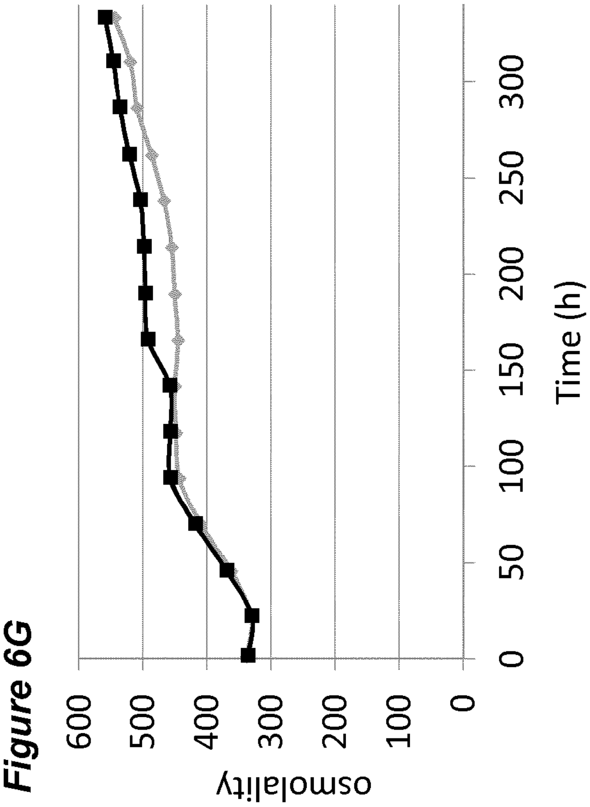
Figure 6F:
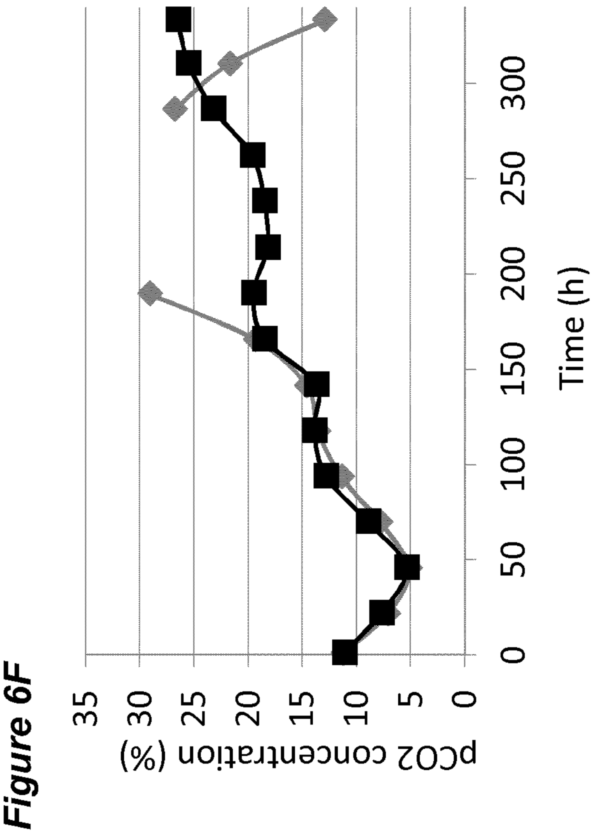

FIG. 6B shows that at the end of the 14 day production process, cell viability in the process with the instant pH up-shift (ΔpH 0.20 units at 144 hours) is comparable with the cell viability in the process without a pH up-shift. FIG. 6C shows that in the process with the instant pH up-shift lactate levels reach a high of about 78% after approximately 200 hours, before gradually dropping to less than 40% at the end of the process. At the end of the process lower amounts of lactate are produced with the instant pH up-shift settings in comparison to the process without a pH up-shift. FIG. 6D shows that in the process with the instant pH up-shift, ammonium levels reach a high of about 90% after approximately 110 hours, which then drop rapidly to about 20% before being maintained at this low level until the end of the process. Lower amounts of ammonium are produced with the instant pH up-shift settings in comparison to the process without a pH up-shift. FIG. 6E shows that at the end of the process, product titer in the process with the instant pH up-shift is higher than in the process without a pH up-shift. FIG. 6F shows that in the process with the instant pH up-shift, the $pCO_2$ level increased gradually and moderately to approximately 26% by the end of the process. In contrast, much higher $pCO_2$ levels were observed in the process without a pH up-shift, particularly between 160 and 320 hours. FIG. 6G shows that at the end of the process, culture osmolality in the process with the instant pH up-shift is just slightly higher than in the process without a pH up-shift.

Example-7: pH Up-Shift Through Widening pH Dead-Band

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 7A illustrates pH set-point and dead-band settings and feed schedule for the culture process. The online pH set-point was initially maintained at 7.00±0.05 using carbon-dioxide gas injection or by addition of 1M sodium carbonate. At about 144 hours, the pH set-point remained at 7.00 and the pH dead-band was widened from ±0.05 to ±0.25. At about 192 hours, the pH set-point was increased from 7.00 to 7.20 and the dead-band restored to ±0.05. The pH set-point was maintained at this value until the end of the production process. Process samples were taken from the cultures daily and analyzed for the required parameters.

FIGS. 7B-G illustrate the effects on cell viability, lactate concentration, ammonium concentration, product titer, $pCO_2$, and osmolality during the culture process having pH settings according to FIG. 7A (black squares), as compared to a culture process having pH settings according to FIG. 1 (grey diamonds).

Figure 7B:
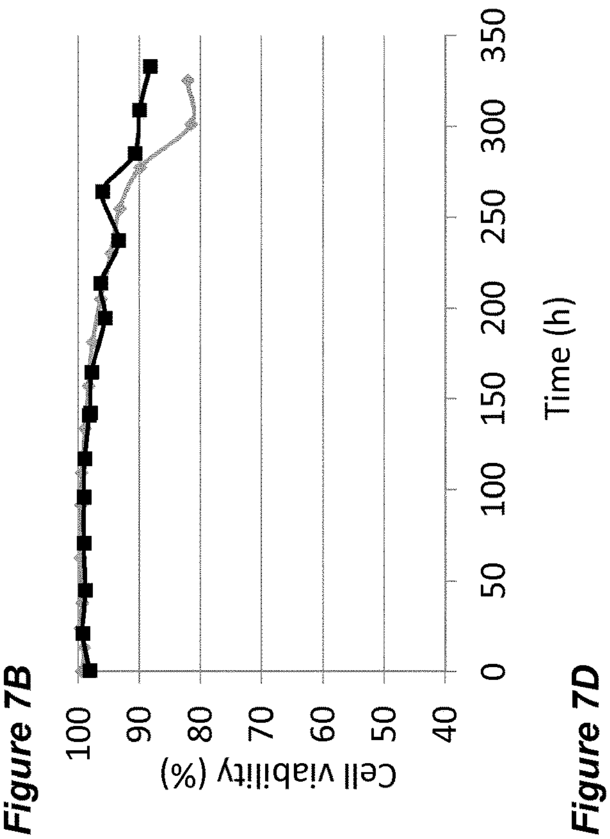
Figure 7C:
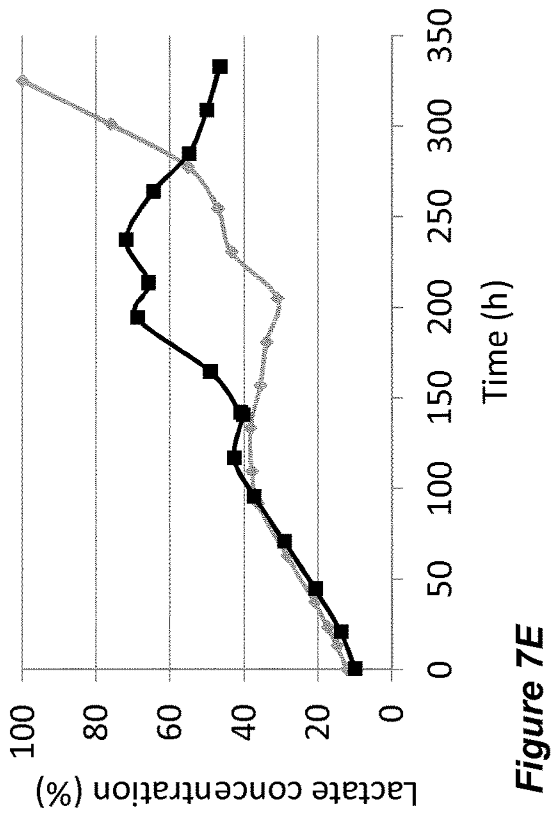
Figure 7D:
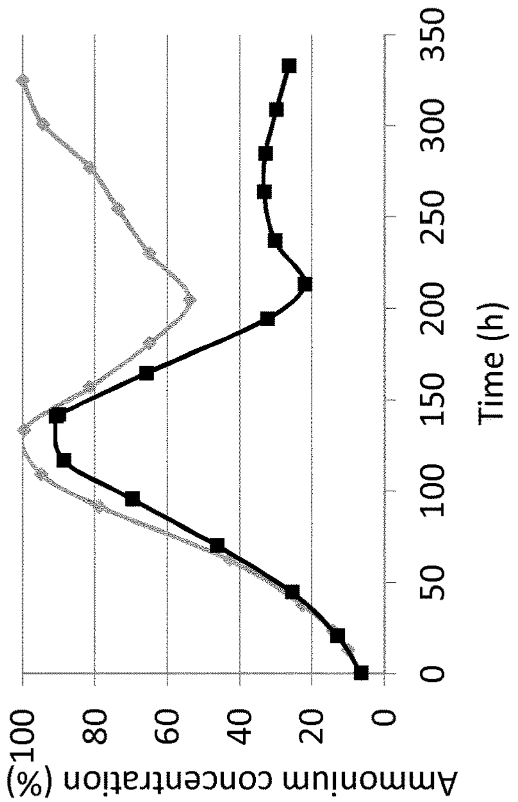
Figure 7E:
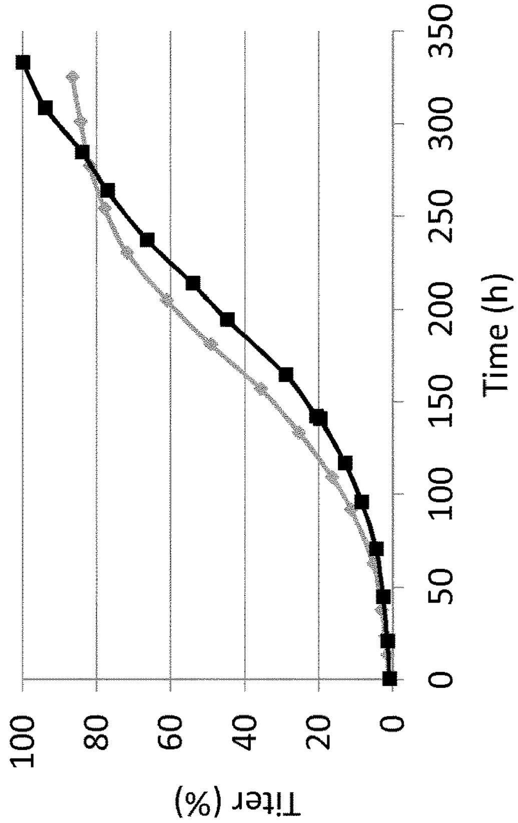
Figure 7G:
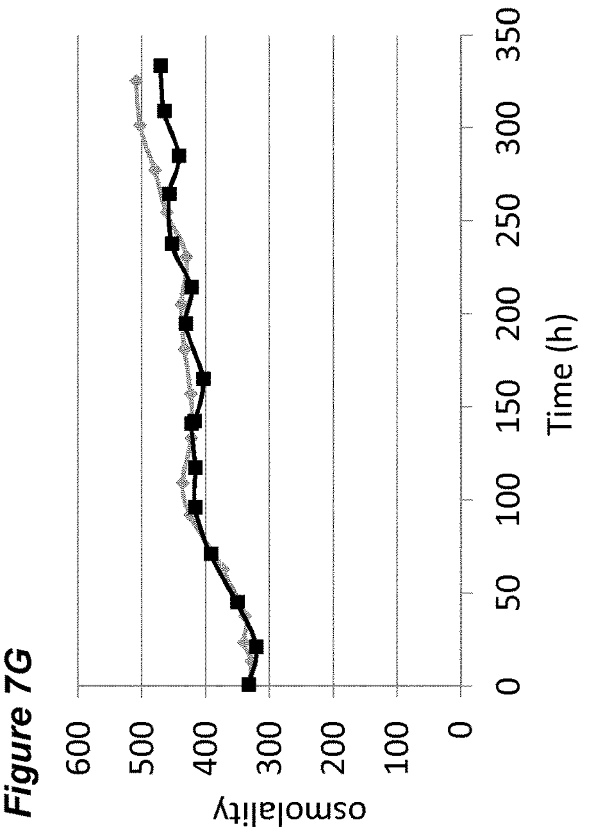
Figure 7F:
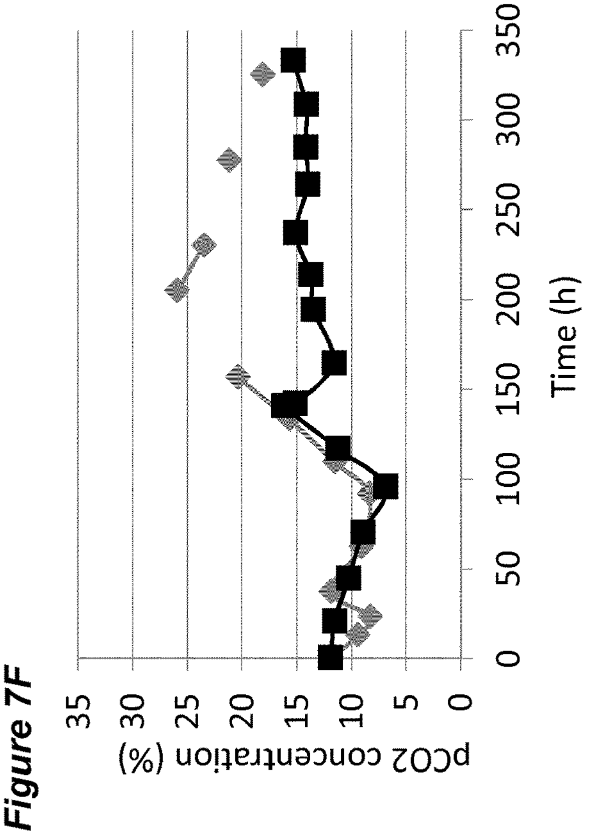

FIG. 7B shows that at the end of the 14 day production process, cell viability in the process with the pH up-shift (ΔpH 0.20 units through widening pH-dead-band between 144 and 192 hours) is higher than the cell viability in the process without a pH up-shift. FIG. 7C shows that in the process with the pH up-shift lactate levels reach a high of about 70% after approximately 240 hours, gradually dropping to about 45% at the end of the process. At the end of the process lower amounts of lactate are produced with the pH up-shift settings in comparison to the process without a pH up-shift. FIG. 7D shows that in the process with the pH up-shift ammonium levels reach a high of about 90% after approximately 110 hours, before dropping rapidly to about 22% and then being maintained between 22-32% until the end of the process. Lower amounts of ammonium are produced with the pH up-shift settings in comparison to the process without a pH up-shift. FIG. 7E shows that at the end of the process, product titer in the process with the pH up-shift is at least 10% higher than in the process without a pH up-shift. FIG. 7F shows that in the process with the pH up-shift the $pCO_2$ level increased gradually to approximately 16% at around 140 hours then was maintained at this level until the end of the process. In contrast, much higher $pCO_2$ levels were observed in the process without a pH up-shift, particularly between 160 and 280 hours. FIG. 7G shows that at the end of the process, culture osmolality in the process with the pH up-shift is lower than in the process without a pH up-shift.

Example-8: Incremental pH Set-Point Increase

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 8A illustrates the pH set-point and dead-band settings and feed schedule for the culture process. The online pH set-point was initially maintained at 7.00±0.05 using carbon-dioxide gas injection or by addition of 1M sodium carbonate. At about 156 hours, the pH set-point was increased to pH 7.05±0.05 and maintained for 12 hours. At about 168 hours, the pH set-point was increased to pH 7.10±0.05 and maintained for 12 hours. At about 180 hours, the pH set-point was increased to pH 7.15±0.05 and maintained for another 12 hours. Finally, at about 192 hours, the pH set-point was increased to pH 7.20±0.05 and maintained at this value until the end of the production process. Process samples were taken from the cultures daily and analyzed for the required parameters.

FIGS. 8B-G illustrate the effects on cell viability, lactate concentration, ammonium concentration, product titer, $pCO_2$, and osmolality during the culture process having pH settings according to FIG. 8A (black squares), as compared to a culture process having pH settings according to FIG. 1 (grey diamonds).

Figure 8B:
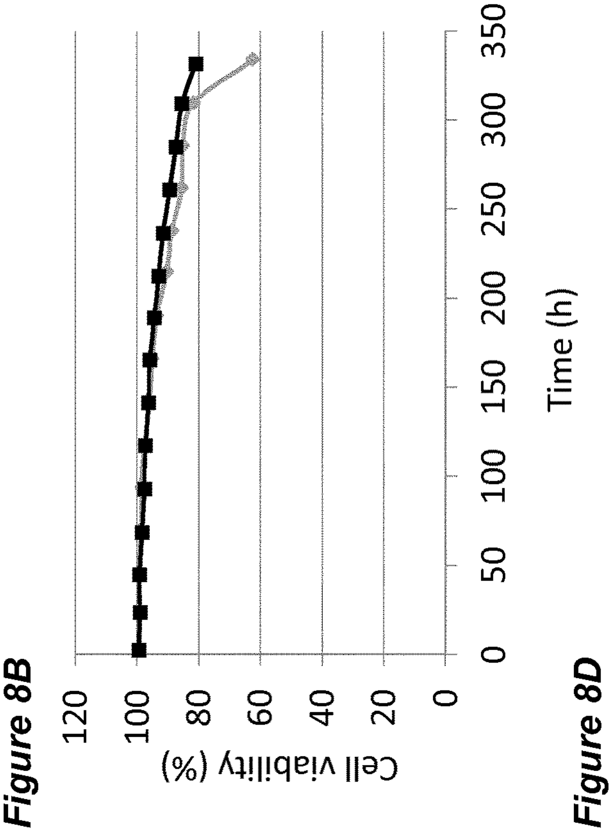
Figure 8C:
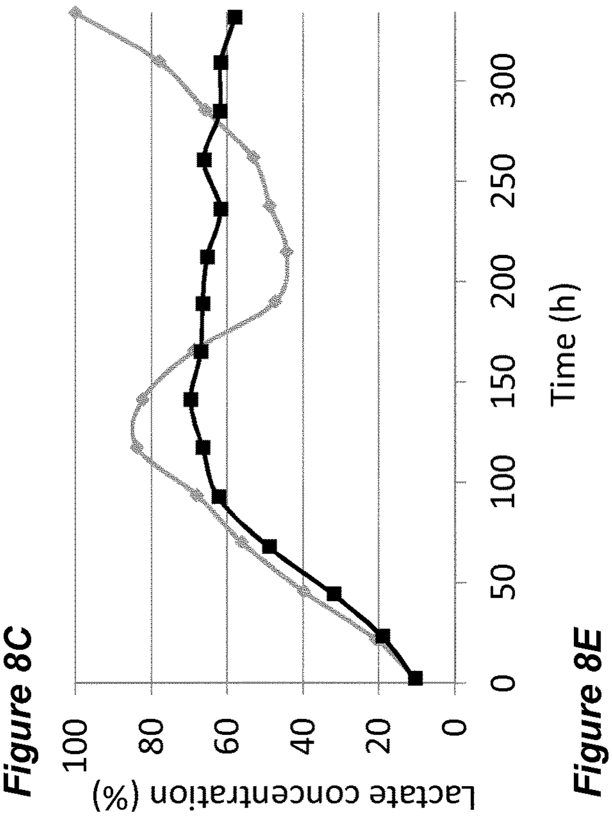
Figure 8D:
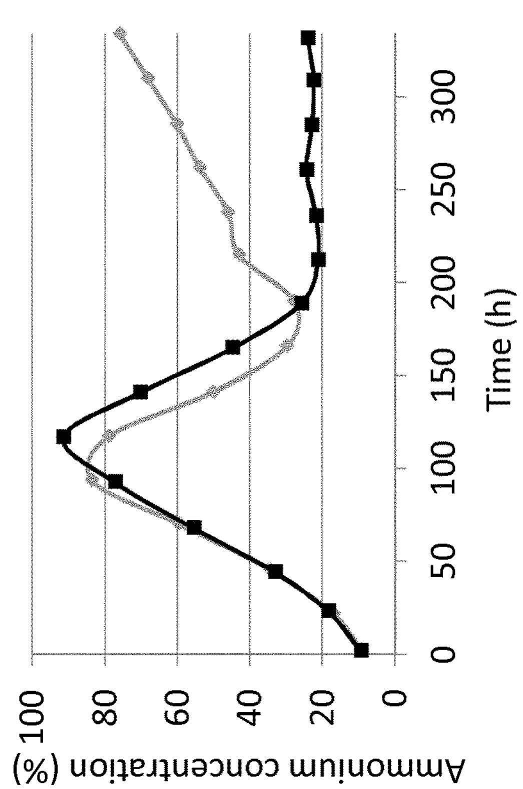
Figure 8E:
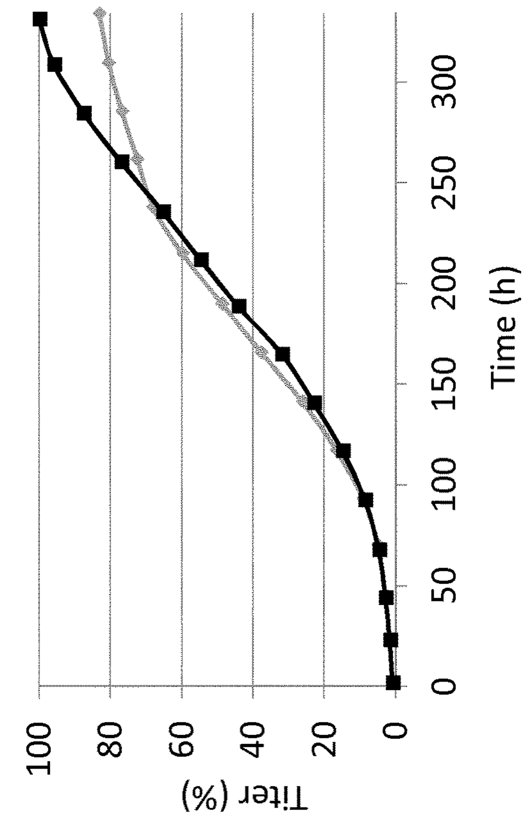
Figure 8F:
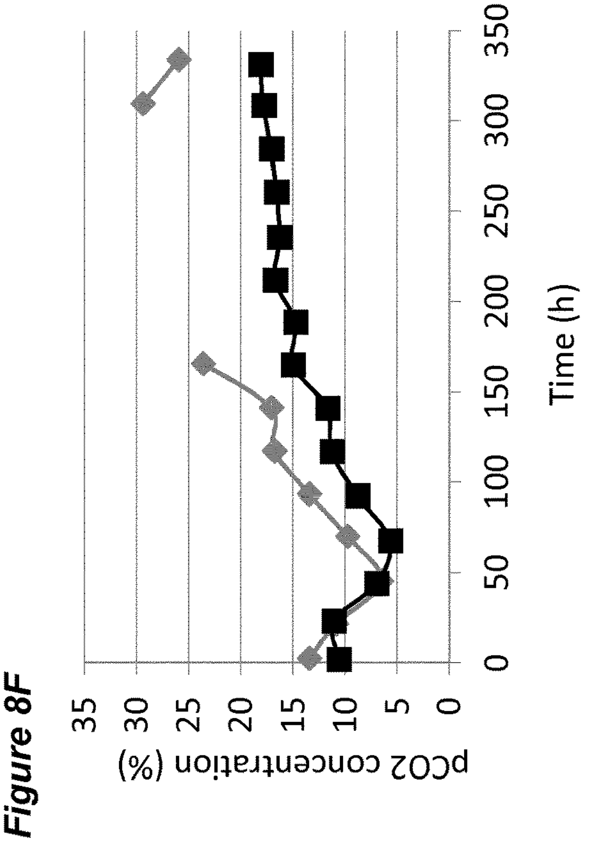
Figure 8G:
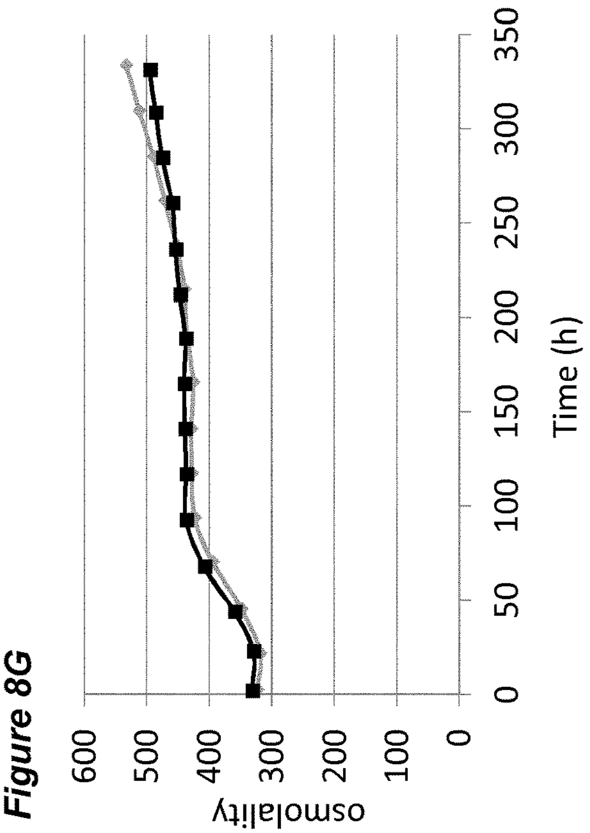
Figure 9A:
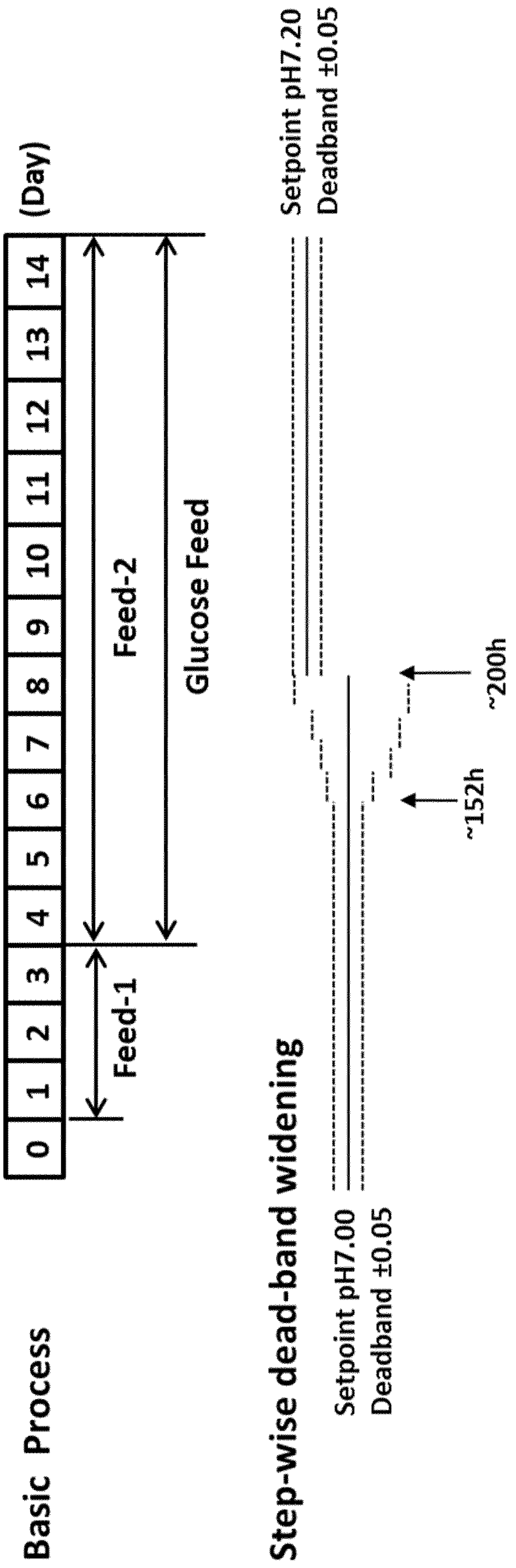

FIG. 8B shows that at the end of the 14 day process, cell viability in the process with the pH up-shift (ΔpH 0.20 units through stepwise pH-set-point increases between 156 and 192 hours) is higher than the cell viability in the process without a pH up-shift. FIG. 8C shows that in the process with the pH up-shift, lactate levels reach a high of about 70% after approximately 140 hours, before gradually dropping to about 58% at the end of the process. At the end of the process lower amounts of lactate are produced with the pH up-shift settings in comparison to the process without a pH up-shift. FIG. 8D shows that in the process with the pH up-shift ammonium levels reach a high of about 90% after approximately 116 hours, dropping rapidly to about 25% after about 188 hours and then being maintained between 21-24% until the end of the process. Lower amounts of ammonium are produced with the pH up-shift settings in comparison to the process without a pH up-shift. FIG. 8E shows that at the end of the process, product titer in the process with the pH up-shift is at least 15% higher than in the process without a pH up-shift. Figure shows that in the process with the pH up-shift the $pCO_2$ level increased gradually to approximately 17% at around 210 hours then was maintained at this level until the end of the process. In contrast, much higher $pCO_2$ levels were observed in the process without a pH up-shift, particularly between 160 and 280 hours. FIG. 8G shows that at the end of the process, culture osmolality in the process with the pH up-shift is lower than in the process without a pH up-shift.

Example-9: Incremental pH-Dead-Band Widening

Anti-Ang2NEGF cells were grown in shake flasks and passaged several times. The production fermentation run was started with an initial cell count of about $6.0\times10^5$ cells/mL, at 36.5° C. and a pH set-point of 7.00 with a dead-band of ±0.05 pH units. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 9A illustrates the pH set-point and dead-band settings and feed schedule for the culture process. The online pH set-point was initially maintained at 7.00±0.05 using carbon-dioxide gas injection or by addition of 1M sodium carbonate. At about 152 hours, the pH dead-band was widened to ±0.10 and maintained for 12 hours. At about 164 hour, the pH dead-band was widened again to ±0.15 and maintained for 12 hours. At about 176 hours, the pH dead-band was widened to ±0.20 and maintained for a further 12 hours. At about 188 hours, the pH dead-band was widened to ±0.25 and maintained for 12 hours. Finally, at about 200 hours, the pH set-point was increased to pH 7.20±0.05 and maintained at this value until the end of the production process. Process samples were taken from the cultures daily and analyzed for the required parameters.

FIGS. 9B-G illustrate the effects on cell viability, lactate concentration, ammonium concentration, product titer, $pCO_2$, and osmolality during the culture process having pH settings according to FIG. 9A (black squares), as compared to a culture process having pH settings according to FIG. 1 (grey diamonds).

Figure 9C:
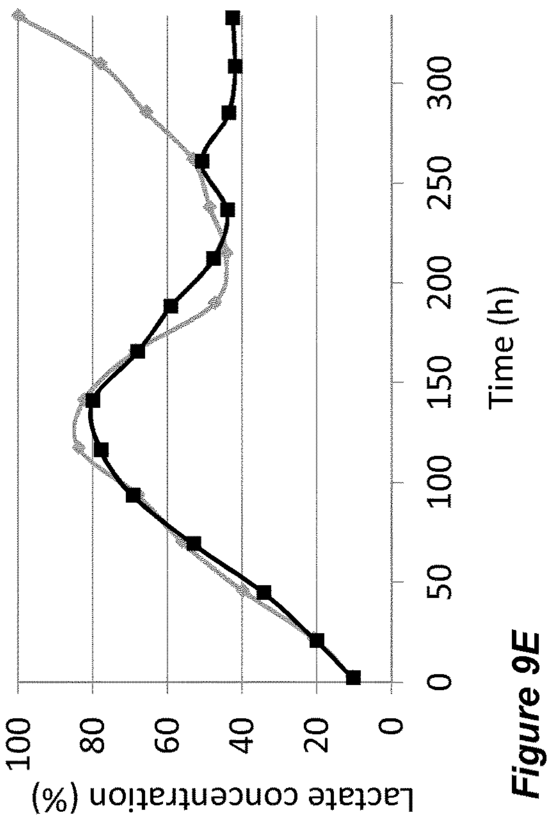
Figure 9E:
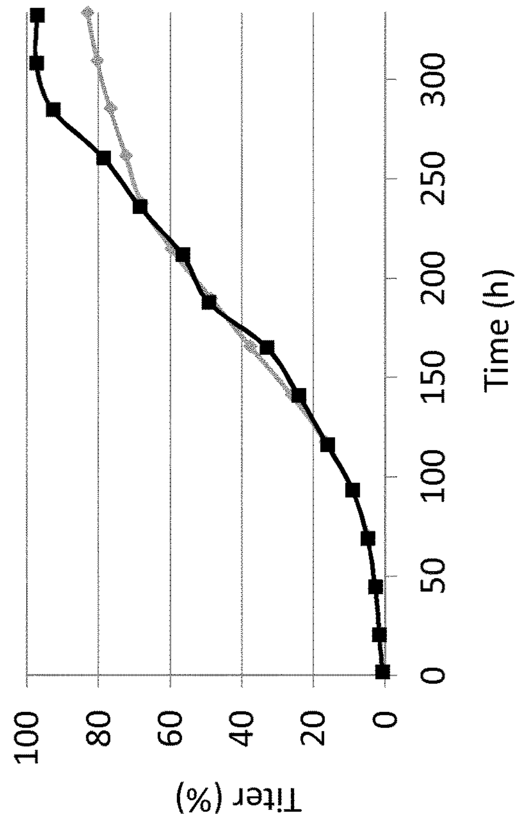
Figure 9B:
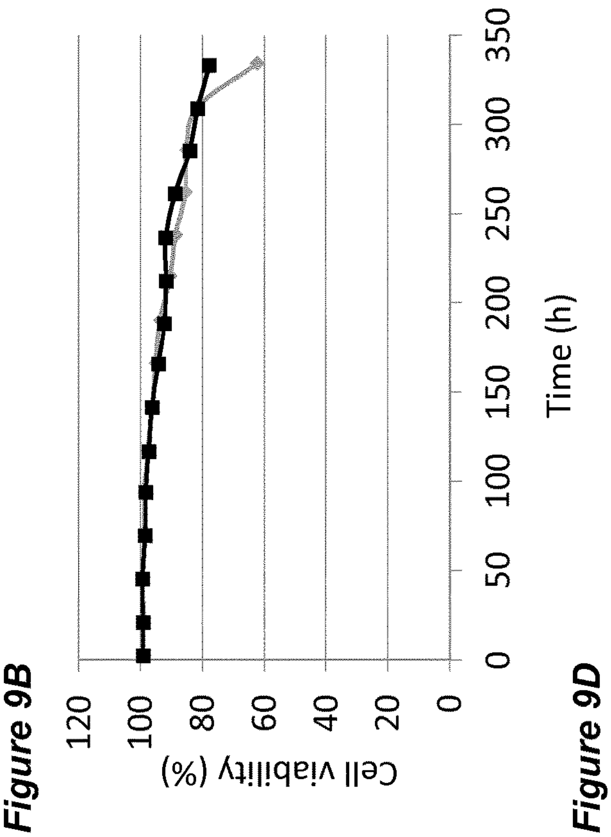
Figure 9D:
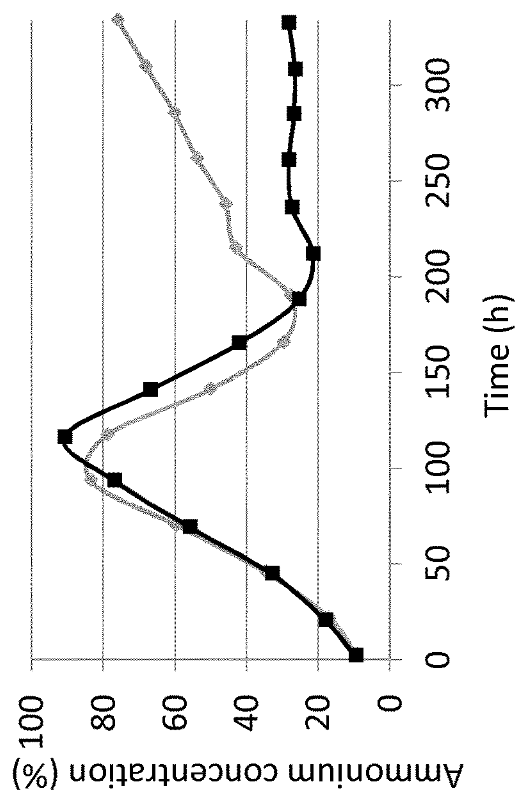
Figure 9G:
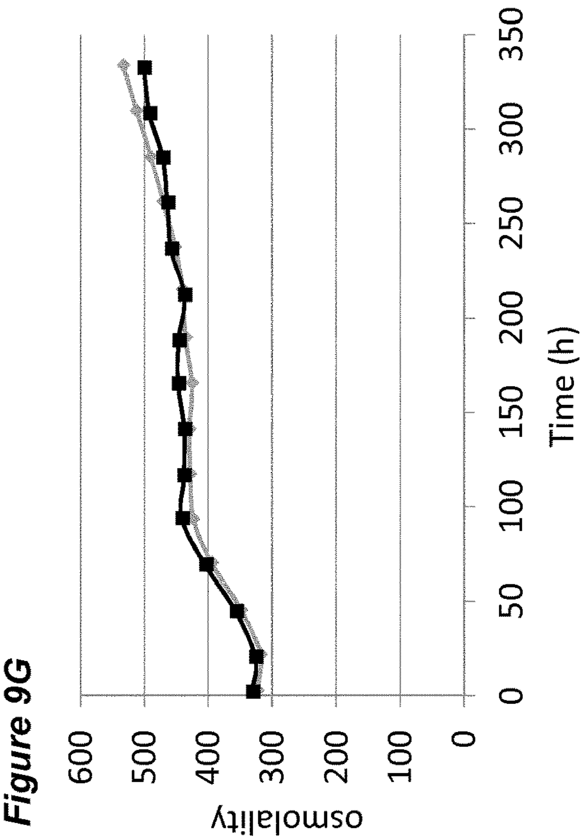
Figure 9F:
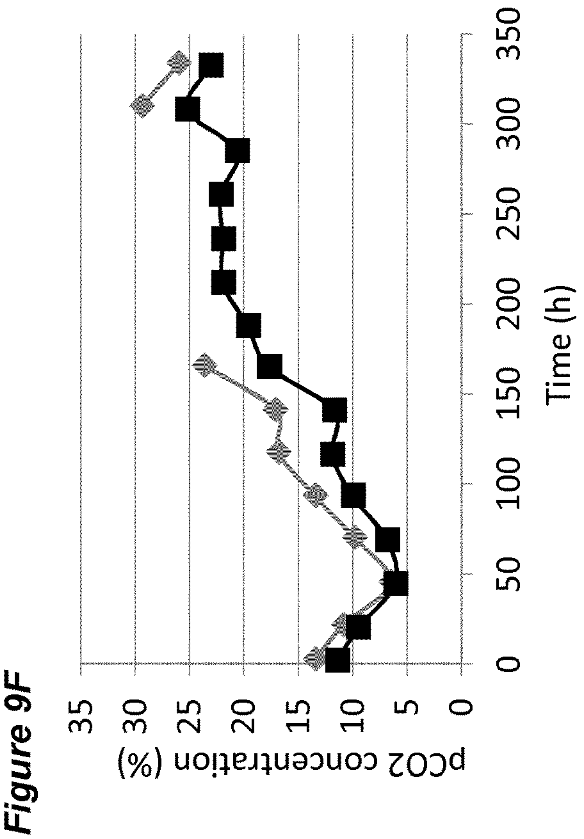

FIG. 9B shows that at the end of the 14 day process, cell viability in the process with the pH up-shift (ΔpH 0.20 units through stepwise widening of the pH dead-band between 152 and 200 hours) is higher than the cell viability in the process without a pH up-shift. FIG. 9C shows that in the process with the pH up-shift, lactate levels reach a high of about 80% after approximately 140 hours, gradually dropping to about 42% at the end of the process. Lower amounts of lactate are produced in the process with the pH up-shift settings in comparison to the process without a pH up-shift, particularly at the end of the process. FIG. 9D shows that in the process with the pH up-shift ammonium levels reach a high of about 90% after approximately 116 hours, before dropping rapidly to about 25% after about 190 hours and then being maintained between 21-28% until the end of the process. Lower amounts of ammonium are produced with in the process with the pH up-shift settings in comparison to the process without a pH up-shift. FIG. 9E shows that at the end of the 14 day process, product titer in the process with the pH up-shift is about 15% higher than in the process without a pH up-shift. FIG. 9F shows that in the process with the pH up-shift, the $pCO_2$ level increased gradually to approximately 22% at around 210 hours then was maintained between 22 and 25% until the end of the process. In contrast, much higher $pCO_2$ levels were observed in the process without a pH up-shift, particularly between 160 and 280 hours. FIG. 9G shows that at the end of the process, culture osmolality in the process with the pH up-shift is lower than in the process without a pH up-shift.

Example-10: Different pH Control Strategies

Anti-CSF-1R cells were grown in shake flasks and passaged several times. The production fermentation run was started with an initial cell count of about $6.0\times10^5$ cells/mL at 36.5° C., and a pH set-point of 7.00 with a dead-band of ±0.05 pH units. 0.25 L bioreactors were employed, at an initial culture volume of 0.2 L. Feed medium was prepared in solution and was continuously added to the culture on Day 1-3 at an amount ranging from about 2.0 to about 3.0 weight % of the initial culture weight per day. pH up-shift feed medium was prepared in solution and was continuously added to the culture on Day 4-14 at an amount ranging from about 0.5 to about 1.5 weight % of the initial culture weight per day. An additional glucose feed solution was prepared and continuously added to the culture during Day 4-14 to maintain glucose concentration at about ≥3 g/l.

FIG. 10A illustrates the pH set-point and dead-band settings and feed schedules for two different culture processes.

For production process #1, the online pH set-point was initially maintained at 7.00±0.05 using carbon-dioxide gas injection or by addition of 1M sodium carbonate. Starting from about 144 hours, the pH set-point was set to gradually increase from 7.00 to 7.20 within about 48 hours. At about 192 hours, the pH set-point reached pH 7.20±0.05 and was maintained at this value until the end of the production process.

For production process #2, the online pH set-point was initially maintained at 7.00±0.05 using carbon-dioxide gas injection or by addition of 1M sodium carbonate. At the time point of 48 hours, the pH set-point was lowered to 6.80±0.05 and maintained at this value until 240 hours. Starting from about 240 hours, the pH set-point was set to gradually increase from 6.80±0.05 to 7.00±0.05 within about 48 hours. At about 288 hour, the pH set-point reached pH 7.00±0.05 and was maintained at this value until the end of the production process.

Process samples were taken from the cultures daily and analyzed for the required parameters.

FIGS. 10B-F illustrate the effects on cell viability, lactate concentration, ammonium concentration, product titer, and osmolality during the culture process having pH settings according to FIG. 10A process #1 (black squares), as compared to a culture process having pH settings according to FIG. 10A process #2 (grey diamonds).

FIG. 10B illustrates the difference in cell viability during the two culture processes (process #1 black squares; process #2 grey diamonds). After 14 days, cell viability in process #1 (pH ramp ΔpH 0.20 units between 144 and 192 hours) is higher than in process #2. FIG. 10C shows that in process #1, lactate levels reach about 68% at the end of the 14 day production process. Lower amounts of lactate are produced in the process with the pH up-shift in accordance with the processes of the invention, in comparison to the process without a pH up-shift in accordance with the invention. In process #2 there is an increase in pH but the process does not involve a first culture stage comprising inoculating the cells at the first pH and culturing the cells at that first pH, followed by a second culture stage in which the cells are cultured at a second pH that is higher than the first pH. Unlike process #1, process #2 comprises a pH down-shift. FIG. 10D shows that in process #1, ammonium levels reach a high of about 90% after 115 hours, and drop to about 15% before increasing to about 80% at the end of the production process. Lower amounts of ammonium are produced with in the process with the pH up-shift in accordance with the invention, in comparison to the process without a pH up-shift in accordance with the invention. FIG. 10E shows that at the end of the 14 day production process, anti-CSF-1R product titer from process #1 is higher than for process #2. FIG. 10F shows that at the end of the process, culture osmolality in the process with the pH up-shift in accordance with the invention is lower than in the process without a pH up-shift in accordance within the invention

Example-11: Reduced Temperature

Anti-Ang2NEGF-expressing CHO KSV cells were grown in shake flasks and passaged several times. The production fermentation run was started with an initial cell count of about $6.0\times10^5$ cells/mL, at an initial temperature of 36.5° C. and a pH set-point of 7.00 with a dead-band of ±0.05 pH units.

A feed medium was prepared in solution and was continuously added to the culture on Day 3-6 at an amount ranging from about 2.0 to about 3.0 weight % of the initial culture weight per day.

A pH up-shift feed medium was prepared in solution and was continuously added to the culture on Day 7-14 at an amount ranging from about 0.5 to about 1.5 weight % of the initial culture weight per day. An additional glucose feed solution was prepared and continuously added to the culture during Day 7-14 to maintain glucose concentration at about ≥3 g/l.

FIG. 11A illustrates the temperature settings, pH set-point and dead-band settings, and feed schedules for two different culture processes.

For production Process A, the online pH set-point was maintained constant at 7.00±0.05 using carbon-dioxide gas injection or by addition of 1M sodium carbonate for the entire duration of the process. The temperature was maintained constant at 36.5° C. for the entire duration of the process.

For production Process B, the online pH set-point was maintained constant at 7.00±0.05 using carbon-dioxide gas injection or by addition of 1M sodium carbonate for the entire duration of the process. The temperature was initially maintained at 36.5° C. At about 144 hours, the temperature was lowered to 34.0° C., and was maintained at this value until the end of the production process.

Process samples were taken from the cultures daily and analyzed for the required parameters.

Viable cell density (VCD) was measured with Trypan Blue dye exclusion using a Cedex HiRes Analyzer (Material Number: 05650216001, Roche Diagnostics GmbH, Germany). The integral of viable cell density (IVCD) was calculated using the following equation:

$$IVCD = \int_0^t VCD(t)dt$$

where t=culture duration and VCD=Viable Cell Density.

At the end of main culture production process, cell culture fluid was collected through centrifugation. The supernatants were subjected to further small-scale purification with Protein-A.

Glycosylation pattern of the purified antibody was analyzed using RP-HPLC coupled with ESI-MS with 2AB-labeled N-glycans (Chen and Flynn, 2007).

FIGS. 11B-G illustrate the effects on cell viability, lactate concentration, ammonium concentration, product titer, $pCO_2$, and osmolality during the culture process having pH settings according to FIG. 11A process A (grey diamonds), as compared to a culture process having pH settings according to FIG. 11A process B (black squares).

FIG. 11B illustrates the difference in cell viability during the two culture processes (Process A grey diamonds; Process B black squares). After 14 days, cell viability in Process A (constant 36.5° C. temperature) is slightly lower than in Process B (temperature down-shift from 36.5° C. to 34.0° C. at 144 hours). FIG. 11C shows that in Process A lactate levels reach about 34% at the end of the 14 day production process, whereas lactate levels of 100% were produced in Process B at the same time-point. FIG. 11D shows that in Process A ammonium levels reach a high of about 97% after 115 hours, and drop to about 33% before increasing to about 72% at the end of the production process. In contrast, ammonium levels as high as about 85% were produced in process B at the same time-point. FIG. 11E shows that at the end of the 14 day process, product titer in Process A is about 20% higher than in Process B. FIG. 11F shows that in Process A the $pCO_2$ level increased to greater than 29% at around 200 hours then was maintained at this high level until the end of the process. In Process B the $pCO_2$ levels increased to greater than 29% at around 200 hours, was maintained at this high level until around 260 hours, then decreased to around 6% at the end of the process. FIG. 11G shows that at the end of the process, culture osmolality in Process A is slightly lower than in process B.

The temperature shift from 36.5° C. to about 34.0° C. changed the quality of anti-Ang2NEGF-CrossMab produced by the cells. For example the content of G0F antibody increased by about 3% and G1F structure showed some changes (FIG. 12). Issues related to changes in product quality caused by temperature shifts may be advantageously avoided in the methods of the invention by maintaining a substantially constant temperature.

The temperature shift from 36.5° C. to about 34.0° C. reduced the Integral Viable Cell Density (IVCD), which is an indicator of cellular performance and generally correlates with final product titer. Although reduction in culture temperature may improve final viability of cells it also causes issues of reduced IVCD and reduced product titer (Table 1). These issues may be advantageously avoided in the processes disclosed herein by maintaining the temperature at a substantially constant value.

TABLE 1

| | Final viability | IVCD ($10^5$ cells/ml/hour) |
|---|---|---|
| Process A (36.5° C.) | 73.6% | 21942.6 |
| Process B (36.5→ 34.0° C.) | 75.4% | 19081.2 |

TABLE 2

EXPERIMENTAL RESULTS SUMMARY

| No. | Description | Cell Viability at Day −14 (%) | Relative level of Lactate at Day −14 (%) | Relative level of Ammonium at Day −14 (%) | Relative Titer (% |
|---|---|---|---|---|---|
| Example 1 (Ferm in 2 L bioreactor) | pH constant at 7.00 ± 0.05 | 62.9 | 100 | 75.9 | 89.0 |
| Example 2 (Ferm in 2 L bioreactor) | Process with a pH-ramp | 78.6 | 73.4 | 18.1 | 100.0 |

TABLE 2-continued

| EXPERIMENTAL RESULTS SUMMARY | | | | | |
|---|---|---|---|---|---|
| No. | Description | Cell Viability at Day −14 (%) | Relative level of Lactate at Day −14 (%) | Relative level of Ammonium at Day −14 (%) | Relative Titer (% |
| Example 3 (Ferm in 2 L bioreactor) | Process with a pH-ramp | 78.9 | 68.2 | 22.6 | 97.7 |
| Example 4 (Ferm in 2 L bioreactor) | Process with a pH-ramp | 76.9 | 88.2 | 15.7 | 94.9 |
| Example 5 (Ferm in 2 L bioreactor) | Process with a pH-ramp | 77.9 | 80.9 | 43.2 | 91.0 |
| Example 6 (Control in 2 L bioreactor) | pH constant at 7.00 ± 0.05 | 74.3 | 78.4 | 100 | 91.4 |
| Example 6 (Ferm in 2 L bioreactor) | Process with an instant pH-shift | 74.2 | 38.2 | 18.9 | 100.0 |
| Example 7 (Control in 2 L bioreactor) | pH constant at 7.00 ± 0.05 | 82.1 | 100.0 | 100.0 | 86.5 |
| Example 7 (Ferm in 2 L bioreactor) | Process with a pH-shift through widening pH-deadband | 88.2 | 46.6 | 24.4 | 100.0 |
| Example 8 (Ferm in 2 L bioreactor) | Process with a stepwise pH-increase | 81.1 | 57.9 | 23.9 | 100.0 |
| Example 9 (Ferm in 2 L bioreactor) | Process with a stepwise pH-deadband widening | 77.9 | 42.5 | 28.2 | 97.1 |
| Example 10 (Ferm in 0.25 L bioreactor) | Process #1 with pH-ramp | 60.9 | 67.8 | 80.7 | 96.7 |
| Example 10 (Ferm in 0.25 L bioreactor) | Process #2 with specified pH-profile | 47.4 | 100.0 | 99.8 | 84.2 |
| Example 11 (Ferm in 2 L bioreactor) | Process A pH constant at 7.00 ± 0.05 temperature constant at 36.5° C. | 73.6 | 33.6 | 72.0 | 100 |
| Example 11 (Ferm in 2 L bioreactor) | Process B pH constant at 7.00 ± 0.05 temperature down-shift | 75.3 | 100.0 | 85.1 | 81.4 |

REFERENCES

A number of publications are cited above in order to more fully describe and disclose the invention and the state of the art to which the invention pertains. Full citations for these references are provided below. The entirety of each of these references is incorporated herein.

For standard molecular biology techniques, see Sambrook, J., Russel, D. W. *Molecular Cloning, A Laboratory Manual.* 3 ed. 2001, Cold Spring Harbor, N.Y.: Cold Spring Harbor Laboratory Press Aggarwal 2011 Nature Biotechnology, 29:1083-1089
Altamirano, et al. 2000 Biotechnol. Progr. 16: 69-75
Altamirano et al., 2001 Biotechnology and Bioengineering, 76(4):351-360
Altamirano, et al., 2004 J. Biotechnology 110(2): 171-179
Altamirano, C. et al. 2006 J. Biotechnol. 125: 547-556
Andersen and Goochee 1995 Biotechnol Bioeng 47(1): 96-105
Borys, et al., 1993 Biotechnology 11:720-724
Borys et al., 1994 Biotechnol Bioeng 43(6): 505-514
Chen and Flynn 2007 Analytical biochemistry 370.2: 147-161
Chen, K. et al. 2001 Biotechnol. Bioeng. 72: 55-61
Cherlet and Marc 1999. Cytotechnology 28: 213-227
deZengotita et al., 1998. Cytotechnology 28: 213-227
deZengotita et al., 2002 Biotechnol Bioeng. 77:369-380
Fenn et al., 2013 PLoS ONE 8(4): e61953
Fogolin et al. 2004 J. Biotechnol. 109:179-191
Gawlitzek et al. 2000 Biotechnol Bioeng 68(6): 637-646
Gomez et al. 2010 Biotechnology Progress 26(5):1438-1445
Goudar et al. 2007 Biotechnol. Bioeng. 96(6):1107-1117
Hassell et al. 1991 Appl. Biochem. Biotechnol. 30:29-41
Hayter et al. 1991 Appl Microbiol Biotechnol 34(5): 559-564
Hume and MacDonald 2012 Blood 119, 1810-1820
Irani et al. 1999 Biotechnol. Bioeng. 66,238-246
Kienast et al. 2013 Clinical Cancer Research 19(24): 6730-6740
Kim and Lee 2007a Appl. Microbiol. Biotechnol. 74:152-159
Kim and Lee 2002 J. Biotechnol. 95(3): 237-248
Kim and Lee 2007b Appl. Microbiol. Biotechnol. 76:659-665
Kim et al. 2012 Appl. Microbiol. Biotechnol. 93 (3): 917-930
Kimura and Miller 1997 Biotechnol Prog. 13:311-317
Lao and Toth 1997 Biotechnol. Prog. 13: 688-691
Leader et al. 2008. Nature Reviews Drug Discovery 7: 21-39
Li et al. 2006. Biotech Prog 22: 696-703
Lonza Biologics plc Slough UK. 2009. The GS Gene Expression System, Lonza Brochures, http://www.lonza.com/group/en/products services/custommanufactoring/mammalian/geneexpressions.html.
Maranga and Goochee 2006 Biotechnol Bioeng. 94:139-150
Michaels et al. 1995a Biotechnol Bioeng 47:407-419
Michaels 1995b Biotechnol Bioeng 47:420-430
Mostafa and Gu 2003 Biotechnol Prog 19.1:45-51
Oguchi et al. 2006 Cytotechnology 52: 199-207
Omasa et al. 2010 Pharm. Biotechnol. 11 (3): 233-240
Ozturk et al. 1992 Biotechnol. Bioeng., 39:418-431
Paredes et al. 1999 Cytotechnology 30: 85-93
Ries et al. 2014 Cancer Cell 25.6: 846-859

Schaefer et al. 2011 Proc. Natl. Acad. Sci. U.S.A. 108: 11187-11192
Schmelzer et al. 2000 Biotechnol. Bioeng. 67 (2):189-196
Schmelzer and Miller 2002 Biotechnol Prog. 18:346-353
Trummer, et al. 2006 Biotechnology and Bioengineering 94(6):1045-1052
Whitford 2006 Bioprocess International, 30-40, April 2006
Wlaschin and Hu 2007 J. Biotechnol. 131:168-176
Xie and Wang, 1993 Biotechnol Bioeng 43:1175-1189
Yang and Butler 2000 Biotechnol. Bioeng. 68: 370-380
Yeo et al., 2006 Biotechnol Lett. 28:1445-1452
Yoon et al. 2005 Biotechnol. Bioeng. 22: 345-356
Yuk et al. 2014 Biotechnology Progress30.2: 429-442
Zanghi et al. 1999 Biotechnol. Bioeng. 65 (2), 182-191
Zhang et al. 2004 J Chem Technol Biotechnol 79:171-181
Zhou et al. 1995 Biotechnology and bioengineering 46(6): 579-587
Zhou et al. 2011 J. Biotechnol. 153:27-34
Zhu et al. 2005 Biotechnol Prog. 21:70-77.
Zhu 2012 Biotechnol. Adv. 30 (5):1158-1170

PATENT CITATIONS

US20140051124, U.S. Pat. Nos. 8,470,552, 8,765,413, WO 2008/033517, WO 2011/070024, WO 2011/117329

The following statements relate to aspects of the present disclosure, and form part of the description 1. A fed-batch process for culturing mammalian cells, the process comprising
   a first culture stage, comprising inoculating mammalian cells into a culture medium at a first pH and culturing the cells at the first pH; and
   a second culture stage, comprising culturing the cells at a second pH that is higher than the first pH.
2. A fed-batch process for culturing mammalian cells comprising controlling the pH using pH set-points, the process comprising
   a first culture stage, comprising inoculating mammalian cells into a culture medium at a first pH and culturing the cells at the first pH wherein in the first culture stage the pH set-point is maintained at the first pH; and
   a second culture stage, comprising culturing the cells at a second pH that is higher than the first pH wherein in the second culture stage the set-point is maintained at the second pH;
   and wherein the second pH is at least 0.1 pH units higher than the first pH, and wherein the second culture stage has a duration of at least 6 hours.
3. The process according to any one of the preceding statements, wherein the second culture stage has a duration of at least 3 days.
4. The process according any one of the preceding statements, wherein the temperature of the process is maintained within ±0.5° C.
5. The process according to any one of the preceding statements, wherein optionally the first pH is a value in the range 6.5-7.5, and wherein
   a. the second pH is at least 0.1 pH units higher than the first pH;
   b. the second pH is about 0.1 to 0.5 pH units higher than the first pH; or
   c. the second pH is about 0.2 pH units higher than the first pH.
6. The process according to any one of the preceding statements, wherein
   a. the first pH is about 7.0; and
   b. the second pH is about (i) pH 7.1; (ii) pH 7.2; (iii) pH 7.3; (iv) pH 7.4 (v) pH 7.5, or (vi) 7.1-7.5.
   or wherein
   a. the first pH is 7.0±0.05; and
   b. the second pH is (i) pH 7.1±0.05; (ii) pH 7.2±0.05; (iii) pH 7.3±0.05; (iv) pH 7.4±0.05 (v) pH 7.5±0.05, or (vi) 7.1-7.5±0.05.
7. The process according to any one of the preceding statements comprising controlling the pH using a pH set-point, wherein
   in the first culture stage the set-point is set to the first pH, and
   in the second culture stage the set-point is set to the second pH.
8. The process according to statement 7, in which the set-point is increased from the first pH to the second pH either (a) gradually or (b) instantly.
9. The process according to statement 8, wherein the set-point is increased gradually from the first pH to the second pH, and wherein either (a) the set-point is increased continuously or (b) the set-point is increased in a series of discrete steps.
10. The process according to any one of the preceding statements, in which the pH is increased gradually from the first pH to the second pH over a period of about 24-72 hours.
11. The process according to any one of the preceding statements, comprising adding a pH up-shift feed medium to the culture medium.
12. The process according to any one of statements 7 to 11, wherein the set-point has a dead-band of ±0.05 pH units.
13. The process according to any one of the preceding statements, wherein the mammalian cells are CHO cells.
14. The process according to any one of the preceding statements, which is a process for producing a product, wherein the product is expressed by the mammalian cells, wherein optionally the mammalian cells are recombinant cells, and wherein the product is a recombinant protein.
15. The process according to statement 14, wherein the product is (a) an antibody; (b) vanucizumab; or (c) emactuzumab.
16. The process according to any one of statements 14 to 15, comprising the step of isolating the product, and optionally the step of preparing a composition comprising the product.
17. The product or composition produced by the process of statement 16.
18. The process according to any one of the preceding statements, wherein the inoculating of the mammalian cells into the culture medium is on Day 0, and wherein any one of Days 10-18 comprises a harvest step, which comprises terminating the process by harvesting the cells and/or the product.
19. The process according to any one of the preceding statements, comprising a harvest step, wherein the process is terminated by harvesting the cells and/or the product, and at the harvest step:
   a. cell viability is at least 20% higher than a control process;
   b. lactate levels are at least 20% lower than a control process;

c. ammonium levels are at least 40% lower than a control process; and/or d. product titer is at least 5% higher than a control process;

wherein the control process is the same as the process disclosed in the statement except the second culture stage comprises culturing the cells at the first pH.

20. A process for culturing mammalian cells, the process comprising a first culture stage, comprising culturing the cells at a first pH; and a second culture stage, comprising culturing the cells at a second pH, wherein the second pH is higher than the first pH, wherein the temperature of the process is maintained at a substantially constant value.

21. A process for culturing mammalian cells, which mammalian cells are capable of expressing an antibody, the process comprising a first culture stage, comprising inoculating mammalian cells into a culture medium at a first pH and culturing the cells at the first pH; and a second culture stage, comprising culturing the cells at a second pH that is higher than the first pH.

22. Use of a pH up-shift feed medium, or of an pH-increasing agent, for a. increasing product titer in a mammalian cell culture, wherein the product is expressed in the mammalian cells;

b. increasing cell viability in a mammalian cell culture;

c. extending longevity of a mammalian cell culture;

d. reducing lactate accumulation in a mammalian cell culture;

e. reducing ammonium accumulation in a mammalian cell culture;

f. improving $pCO_2$ profile in a mammalian cell culture;

g. reducing osmolality in a mammalian cell culture;

in a process for culturing mammalian cells as set out in any one of the preceding statements, wherein the pH up-shift feed medium, or pH-increasing agent is added to the mammalian cell culture to increase the pH from the first pH to the second pH.

The invention claimed is:

1. A fed-batch process for culturing recombinant mammalian cells to express an antibody, comprising controlling the pH using a pH set-point, the process comprising:

a first culture stage, comprising inoculating recombinant mammalian cells expressing an antibody into a culture medium at a first pH of 7.0 and culturing the cells at the first pH wherein in the first culture stage the pH set-point is maintained at the first pH; and a second culture stage, comprising culturing the cells for at least 6 hours at a second pH that is at least 0.1 pH units higher than the first pH;

wherein in the second culture stage the set-point is maintained at the second pH and wherein the second pH is (i) pH 7.1; (ii) pH 7.2: (iii) pH 7.3: (iv) pH 7.4: or (v) pH 7.5; wherein:

(a) the temperature of the process is maintained within +0.5° C.; or (b) the pH is increased gradually from the first pH to the second pH over a period of 24-72 hours; and wherein the process increases antibody yield compared to a fed-batch process that does not comprise the second culture stage at a higher second pH of at least 0.1 pH units.

2. The process according to claim 1, wherein the second culture stage has a duration of at least 3 days.

3. The process according to claim 1, wherein the set-point is increased from the first pH to the second pH either (a) gradually or (b) instantly.

4. The process according to claim 1, wherein the set-point is increased gradually from the first pH to the second pH, and wherein either (a) the set-point is increased continuously or (b) the set-point is increased in a series of discrete steps.

5. The process according to claim 1, wherein the set-point has a dead-band of ±0.05 pH units.

6. The process according to claim 1, wherein the recombinant mammalian cells are CHO cells.

7. The process according to claim 1, wherein the antibody is vanucizumab or emactuzumab.

8. The process according to claim 1, comprising the step of isolating the antibody, and optionally the step of preparing a composition comprising the antibody.

9. The process according to claim 1, further comprising adding a pH up-shift medium to the culture medium.

10. A fed-batch process for culturing recombinant mammalian cells to express an antibody, comprising controlling the pH using a pH set-point, the process comprising:

a first culture stage, comprising inoculating recombinant mammalian cells expressing an antibody into a culture medium at a first pH of about 6.9 to 7.1 and culturing the cells at the first pH wherein in the first culture stage the pH set-point is maintained at the first pH; and a second culture stage, comprising culturing the cells for at least 6 hours at a second pH that is at least 0.1 pH units higher than the first pH;

wherein in the second culture stage the set-point is maintained at the second pH and wherein the second pH is about (i) pH 7.1; (ii) pH 7.2; (iii) pH 7.3; (iv) pH 7.4; or (v) pH 7.5; wherein:

(a) the temperature of the process is maintained within +0.5° C.; or (b) the pH is increased gradually from the first pH to the second pH over a period of 24-72 hours, and wherein the process increases antibody yield compared to a fed-batch process that does not comprise the second culture stage at a higher second pH of at least 0.1 pH units.

* * * * *